United States Patent
Goto et al.

(10) Patent No.: US 8,367,707 B2
(45) Date of Patent: *Feb. 5, 2013

(54) PEST CONTROL AGENTS

(75) Inventors: Kimihiko Goto, Yokohama (JP); Ryo Horikoshi, Yokohama (JP); Mariko Tsuchida, Yokohama (JP); Kazuhiko Oyama, Yokohama (JP); Satoshi Omura, Tokyo-To (JP); Hiroshi Tomoda, Chofu (JP); Toshiaki Sunazuka, Funabashi (JP)

(73) Assignees: Meiji Seika Pharma Co., Ltd., Tokyo (JP); The Kitasato Institute, Tokyo-to (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/903,624

(22) Filed: Oct. 13, 2010

(65) Prior Publication Data

US 2011/0034404 A1 Feb. 10, 2011

Related U.S. Application Data

(60) Division of application No. 12/318,232, filed on Dec. 23, 2008, now Pat. No. 7,838,538, which is a continuation of application No. 11/443,299, filed on May 31, 2006, now Pat. No. 7,491,738.

(60) Provisional application No. 60/687,318, filed on Jun. 6, 2005.

(30) Foreign Application Priority Data

Jun. 1, 2005 (JP) ................................ 2005-161019

(51) Int. Cl.
*A01N 43/40* (2006.01)
*A61K 31/44* (2006.01)
*C07D 211/34* (2006.01)

(52) U.S. Cl. ..................................... 514/338; 546/238.1

(58) Field of Classification Search ........................ None
See application file for complete search history.

(56) References Cited

U.S. PATENT DOCUMENTS

| 2,075,359 | A | 3/1937 | Euclid et al. |
| 3,973,944 | A | 8/1976 | Erdmann et al. |
| 4,845,097 | A | 7/1989 | Matsumoto et al. |
| 5,885,963 | A | 3/1999 | Stockhoff et al. |
| 7,491,738 | B2 * | 2/2009 | Goto et al. ..................... 514/338 |

FOREIGN PATENT DOCUMENTS

| JP | 2-209874 | 8/1990 |
| JP | 04-360895 | 12/1992 |
| JP | 06-184158 | 7/1994 |
| JP | 07-126113 | 5/1995 |
| JP | 08-239385 | 9/1996 |
| JP | 08-259569 | 10/1996 |
| JP | 08-269062 | 10/1996 |
| JP | 08-269063 | 10/1996 |
| JP | 08-269064 | 10/1996 |
| JP | 08-269065 | 10/1996 |
| JP | 08-269066 | 10/1996 |
| JP | 08-291164 | 10/1996 |
| WO | 94/09147 | 4/1994 |
| WO | 2004/060065 | 7/2004 |

OTHER PUBLICATIONS

Satoshi Omura et al., "*Pyripyropenes, Highy Potent Inhibitors of Acyl-CoA: Cholesterol Acyltransferase Produced by Aspergillus fumigatus*", The Journal of Antibiotics, vol. 46, No. 7, pp. 1168-1169 (1993).

Toshiaki Sunazuka et al., "*Synthetic Study of γ-Pyrone Meroterpenoids, Pyripyropens*", vol. 56, No. 6, pp. 478-488 (1998).

Rika Obata et al., "*Chemical Modification and Structure-activity Relationships of Pyripyropenes*", The Journal of Antibiotics, vol. 50, No. 3, pp. 229-236 (1997).

Hui-Juan Wang et al., "*Aflavinines and Other Antiinsectan Metabolites from the Ascostromata of Eupenicillium crustaceum and Related Species*", Applied and Environmental Microbiology, vol. 61, No. 12, pp. 4429-4435 (1995).

Rika Obata et al., "*Chemical Modification and Structure-activity Relationships of Pyripyropenes*", The Journal of Antibiotics, vol. 49, No. 11, pp. 1133-11438 (1996).

Supplementary European Search Report (in English language) issued Sep. 25, 2009 in corresponding European Patent Application No. 06 75 6816.

European Search Report (in English language) issued Sep. 29, 2009 in corresponding European Patent Application No. 09 16 4961.

Hiroshi Tomoda et al., "*Pyripyropenes, Novel Inhibitors of Acyl-CoA: Cholesterol Acyltransferase Produced by Aspergillus fumigatus, I. Production, Isolation, and Biological Properties*" Journal of Antibiotics, Japan Antibiotics Research Association, Tokyo, Japan vol. 47, No. 2, Feb. 1, 1994, pp. 148-153 (XP009060945).

Japanese Office Action (with English translation) issued Nov. 8, 2011 in corresponding Japanese Patent Application No. 2007-041108.

Japanese Office Action (with English translation) issued Mar. 30, 2012 in corresponding Japanese Patent Application No. 2007-041108.

* cited by examiner

*Primary Examiner* — Jeffrey Murray

(74) *Attorney, Agent, or Firm* — Wenderoth, Lind & Ponack, L.L.P.

(57) ABSTRACT

Disclosed is a composition for use as a pest control agent, comprising a compound represented by formula (I) or an agriculturally and horticulturally acceptable salt thereof as active ingredient and an agriculturally and horticulturally acceptable carrier:

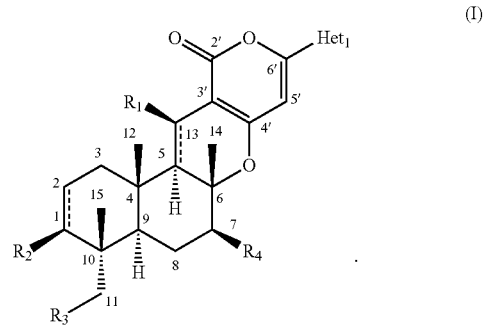

(I)

4 Claims, No Drawings

PEST CONTROL AGENTS

This is a divisional application of Ser. No. 12/318,232, filed Dec. 23, 2008 now U.S. Pat. No. 7,838,568 which is continuation of Ser. No. 11/443,299, filed May 31, 2006, now U.S. Pat. No. 7,491,738 which claims priority from provisional application No. 60/687,318, filed Jun. 6, 2005.

BACKGROUND OF THE INVENTION

1. Field of Invention

The present invention relates to a composition for use as a pest control agent comprising a pyripyropene derivative as active ingredient.

2. Background Art

Pyripyropene A has inhibitory activity against ACAT (acyl-CoA: cholesterol acyltransferase) and is expected to be applied, for example, to the treatment of diseases induced by cholesterol accumulation, as described in Japanese Patent No. 2993767 (Japanese Patent Laid-Open Publication No. 360895/1992) and *Journal of Antibiotics* (1993), 46(7), 1168-9.

Further, pyripyropene analogues and derivatives and ACAT inhibitory activity thereof are described in Journal of Society of Synthetic Organic Chemistry, Japan (1998), Vol. 56, No. 6, pp. 478-488, WO 94/09417, Japanese Patent Laid-Open Publication No. 184158/1994, Japanese Patent Laid-Open Publication No. 239385/1996, Japanese Patent Laid-Open Publication No. 259569/1996, Japanese Patent Laid-Open Publication No. 269062/1996, Japanese Patent Laid-Open Publication No. 269063/1996, Japanese Patent Laid-Open Publication No. 269064/1996, Japanese Patent Laid-Open Publication No. 269065/1996, Japanese Patent Laid-Open Publication No. 269066/1996, Japanese Patent Laid-Open Publication No. 291164/1996, and Journal of Antibiotics (1997), 50(3), 229-36.

Furthermore, *Applied and Environmental Microbiology* (1995), 61(12), 4429-35 describes that pyripyropene A has insecticidal activity against larvae of *Helicoverpa zea*. Furthermore, WO 2004/060065 describes that pyripyropene A has insecticidal activity against *Plutella xylostella* L larvae and *Tenebrio molitor* L. In these documents, however, there is no specific description on insecticidal activity of pyripyropene A against other pests.

Further, none of the above documents describes insecticidal activity of pyripyropene analogues and derivatives.

Up to now, many compounds having insecticidal activity have been reported and have been used as pest control agents. However, the presence of insect species, which are resistant to or can be hardly controlled by these compounds, has posed a problem. Accordingly, the development of a novel pest control agent having excellent insectidal activity has still been desired.

SUMMARY OF THE INVENTION

The present inventors have now found that pyripyropene derivatives represented by formula (I) have significant insecticidal activity.

The present inventors further found that pyripyropene A and its derivatives represented by formula (Ia) have significant insecticidal activity against hemipteran pests.

Furthermore, the present inventors have found novel pyripyropene derivatives represented by formula (Ib) having significant insecticidal activity.

The present invention has been made based on such finding.

Accordingly, an object of the present invention is to provide a composition useful as a pest control agent, that comprises a pyripyropene derivative having significant insecticidal activity as active ingredient and can reliably exhibit the contemplated effect and can be used safely. Another object of the present invention is to provide a hemipteran pest control agent that comprises pyripyropene A and its derivative as active ingredient and can reliably exhibit the contemplated effect and can be used safely. A further object of the present invention is to provide a novel pyripyropene derivative having significant insecticidal activity.

According to one aspect of the present invention, there is provided a composition for use as a pest control agent, comprising a compound represented by formula (I) or an agriculturally and horticulturally acceptable salt thereof as active ingredient and an agriculturally and horticulturally acceptable carrier:

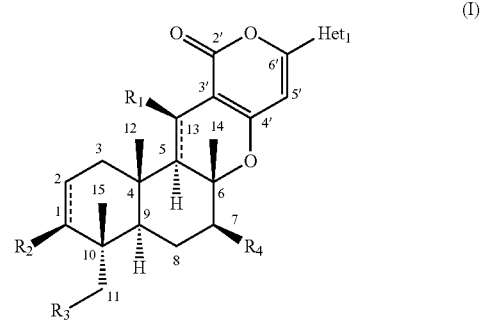

(I)

wherein
Het$_1$ represents optionally substituted 3-pyridyl,
R$_1$ represents hydroxyl,
  optionally substituted C$_{1-6}$ alkylcarbonyloxy,
  optionally substituted C$_{2-6}$ alkenylcarbonyloxy,
  optionally substituted C$_{2-6}$ alkynylcarbonyloxy,
  optionally substituted C$_{1-6}$ alkyloxy,
  optionally substituted C$_{2-6}$ alkenyloxy,
  optionally substituted C$_{2-6}$ alkynyloxy,
  optionally substituted benzyloxy, or
  oxo in the absence of a hydrogen atom at the 13-position, or
the bond between 5-position and 13-position represents a double bond in the absence of R$_1$ and a hydrogen atom at the 5-position,
R$_2$ represents hydroxyl,
  optionally substituted C$_{1-18}$ alkylcarbonyloxy,
  optionally substituted C$_{2-6}$ alkenylcarbonyloxy,
  optionally substituted C$_{2-6}$ alkynylcarbonyloxy,
  optionally substituted benzoyloxy, or
  optionally substituted C$_{1-6}$ alkylsulfonyloxy,
R$_3$ represents a hydrogen atom, hydroxyl,
  optionally substituted C$_{1-18}$ alkylcarbonyloxy,
  optionally substituted C$_{2-6}$ alkenylcarbonyloxy,
  optionally substituted C$_{2-6}$ alkynylcarbonyloxy,
  optionally substituted benzoyloxy,
  optionally substituted C$_{1-6}$ alkylsulfonyloxy,
  optionally substituted benzenesulfonyloxy, or
  optionally substituted five- or six-membered heterocyclic thiocarbonyloxy, or
R$_2$ and R$_3$ together represent —O—CR$_2'$R$_3'$—O— wherein R$_2'$ and R$_3'$, which may be the same or different, represent a hydrogen atom, C$_{1-6}$ alkyl, C$_{1-6}$ alkyloxy, $C_{2-6}$ alkenyl, optionally substituted phenyl, or optionally substituted benzyl, or $R_2'$ and $R_3'$ together represent oxo or $C_{2-6}$ alkylene, and $R_4$ represents a hydrogen atom,
hydroxyl,
optionally substituted $C_{1-18}$ alkylcarbonyloxy,
optionally substituted $C_{2-6}$ alkenylcarbonyloxy,
optionally substituted $C_{2-6}$ alkynylcarbonyloxy,
optionally substituted benzoyloxy,
optionally substituted $C_{1-6}$ alkylsulfonyloxy,
optionally substituted benzenesulfonyloxy,
optionally substituted benzyloxy,
optionally substituted $C_{1-6}$ alkyloxy,
optionally substituted $C_{2-6}$ alkenyloxy,
optionally substituted $C_{2-6}$ alkynyloxy,
$C_{1-6}$ alkyloxy-$C_{1-6}$ alkyloxy,
$C_{1-6}$ alkylthio-$C_{1-6}$ alkyloxy,
$C_{1-6}$ alkyloxy-$C_{1-6}$ alkyloxy-$C_{1-6}$ alkyloxy,
optionally substituted $C_{1-6}$ alkyloxycarbonyloxy,
optionally substituted $C_{1-6}$ alkylaminocarbonyloxy,
optionally substituted saturated or unsaturated five- or six-membered heterocyclic oxy,
optionally substituted saturated or unsaturated five- or six-membered heterocyclic carbonyloxy,
optionally substituted thieno[3,2-b]pyridylcarbonyloxy,
optionally substituted 1H-indolylcarbonyloxy,
optionally substituted saturated or unsaturated five- or six-membered heterocyclic thiocarbonyloxy, or
oxo in the absence of a hydrogen atom at the 7-position, provided that
a compound wherein
$Het_1$ represents 3-pyridyl,
$R_1$ represents hydroxyl, and
all of $R_2$, $R_3$, and $R_4$ represent acetyloxy,
is excluded.

Further, according to another aspect of the present invention, there is provided a composition for use as a a hemipteran pest control agent, comprising a compound represented by formula (Ia) or an agriculturally and horticulturally acceptable salt thereof as active ingredient and an agriculturally and horticulturally acceptable carrier:

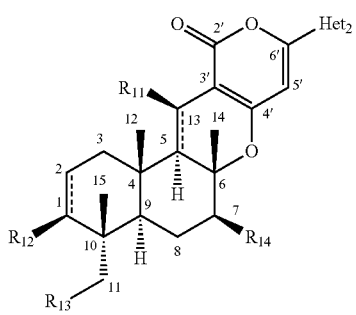

(Ia)

wherein
$Het_2$ represents optionally substituted 3-pyridyl,
$R_{11}$ represents hydroxyl,
optionally substituted $C_{1-6}$ alkylcarbonyloxy,
optionally substituted $C_{2-6}$ alkenylcarbonyloxy,
optionally substituted $C_{2-6}$ alkynylcarbonyloxy,
optionally substituted $C_{1-6}$ alkyloxy,
optionally substituted $C_{2-6}$ alkenyloxy,
optionally substituted $C_{2-6}$ alkynyloxy,
optionally substituted benzyloxy, or
oxo in the absence of a hydrogen atom at the 13-position, or
the bond between 5-position and 13-position represents a double bond in the absence of $R_{11}$ and a hydrogen atom at the 5-position, $R_{12}$ represents hydroxyl,
optionally substituted $C_{1-18}$ alkylcarbonyloxy,
optionally substituted $C_{2-6}$ alkenylcarbonyloxy,
optionally substituted $C_{2-6}$ alkynylcarbonyloxy,
optionally substituted benzoyloxy, or
optionally substituted $C_{1-6}$ alkylsulfonyloxy, $R_{13}$ represents a hydrogen atom,
hydroxyl,
optionally substituted $C_{1-18}$ alkylcarbonyloxy,
optionally substituted $C_{2-6}$ alkenylcarbonyloxy,
optionally substituted $C_{2-6}$ alkynylcarbonyloxy,
optionally substituted benzoyloxy,
optionally substituted $C_{1-6}$ alkylsulfonyloxy,
optionally substituted benzenesulfonyloxy, or
optionally substituted five- or six-membered heterocyclic thiocarbonyloxy, or $R_{12}$ and $R_{13}$ together represent —O—$CR_{12}'R_{13}'$—O— wherein $R_{12}'$ and $R_{13}'$, which may be the same or different, represent a hydrogen atom, $C_{1-6}$ alkyl, $C_{1-6}$ alkyloxy, $C_{2-6}$ alkenyl, optionally substituted phenyl, or optionally substituted benzyl, or $R_{12}'$ and $R_{13}'$ together represent oxo or $C_{2-6}$ alkylene, and $R_{14}$ represents a hydrogen atom,
hydroxyl,
optionally substituted $C_{1-18}$ alkylcarbonyloxy,
optionally substituted $C_{2-6}$ alkenylcarbonyloxy,
optionally substituted $C_{2-6}$ alkynylcarbonyloxy,
optionally substituted benzoyloxy,
optionally substituted $C_{1-6}$ alkylsulfonyloxy,
optionally substituted benzenesulfonyloxy,
optionally substituted benzyloxy,
optionally substituted $C_{1-6}$ alkyloxy,
optionally substituted $C_{2-6}$ alkenyloxy,
optionally substituted $C_{2-6}$ alkynyloxy,
$C_{1-6}$ alkyloxy-$C_{1-6}$ alkyloxy,
$C_{1-6}$ alkylthio-$C_{1-6}$ alkyloxy,
$C_{1-6}$ alkyloxy-$C_{1-6}$ alkyloxy-$C_{1-6}$ alkyloxy,
optionally substituted $C_{1-6}$ alkyloxycarbonyloxy,
optionally substituted $C_{1-6}$ alkylaminocarbonyloxy,
optionally substituted saturated or unsaturated five- or six-membered heterocyclic oxy,
optionally substituted saturated or unsaturated five- or six-membered heterocyclic carbonyloxy,
optionally substituted thieno[3,2-b]pyridylcarbonyloxy,
optionally substituted 1H-indolylcarbonyloxy,
optionally substituted saturated or unsaturated five- or six-membered heterocyclic thiocarbonyloxy, or
oxo in the absence of a hydrogen atom at the 7-position.

Further, the pyripyropene derivative according to the is present invention comprises a compound represented by formula (Ib) or an agriculturally and horticulturally acceptable salt thereof:

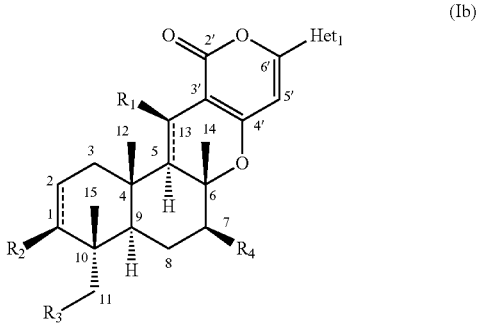

(Ib)

wherein
Het$_1$ represents 3-pyridyl,
R$_1$ represents hydroxyl,
R$_2$ and R$_3$ represent propionyloxy or optionally substituted cyclic
C$_{3-6}$ alkylcarbonyloxy, and
R$_4$ represents hydroxyl,
    optionally substituted cyclic C$_{3-6}$ alkylcarbonyloxy,
    optionally substituted benzoyloxy, or
    optionally substituted saturated or unsaturated five- or six-membered heterocyclic carbonyloxy.

The pyripyropene derivatives represented by formula (I) or formula (Ib) according to the present invention have excellent control effect against agricultural and horticultural pests, sanitary pests, parasites of animals, stored grain pests, clothing pests, and house pests and a compositions comprising the pyripyropene derivatives as active ingredient can be advantageously utilized as a novel pest control agent.

Further, it is surprising that, among the compounds represented by formula (Ia), pyripyropene A has excellent control effect against hemipteran pests. Accordingly, a composition according to the present invention comprising the compounds represented by formula (Ia) including pyripyropene A, can be advantageously utilized particularly a hemipteran pest control agent.

DETAILED DESCRIPTION OF THE INVENTION

The term "halogen" as used herein means fluorine, chlorine, bromine, or iodine, preferably fluorine, chlorine, or bromine.

The terms "alkyl," "alkenyl," and "alkynyl" as used herein as a group or a part of a group respectively mean alkyl, alkenyl, and alkynyl that the group is of a straight chain, branched chain, or cyclic type or a type of a combination thereof unless otherwise specified. Further, for example, "C$_{1-6}$" in "C$_{1-6}$ alkyl" as used herein as a group or a part of a group means that the number of carbon atoms in the alkyl group is 1 to 6. Further, in the case of cyclic alkyl, the number of carbon atoms is at least three.

The term "heterocyclic ring" as used herein means a heterocyclic ring containing one or more, preferably one to four, heteroatoms, which may be the same or different, selected from the group consisting of nitrogen, oxygen, and sulfur atoms. Further, the expression "optionally substituted" alkyl as used herein means that one or more hydrogen atoms on the alkyl group may be substituted by one or more substituents which may be the same or different. It will be apparent to a person having ordinary skill in the art that the maximum number of substituents may be determined depending upon the number of substitutable hydrogen atoms on the alkyl group. This is true of functional groups other than the alkyl group.

3-Pyridyl represented by Het$_1$ and Het$_2$ is optionally substituted, and substituents include halogen atoms, C$_{1-4}$ alkyl, C$_{1-4}$ alkyloxy, nitro, cyano, formyl, trifluoromethyl, trifluoromethoxy, trifluoromethylthio, trifluoromethylsulfinyl, trifluoromethylsulfonyl, acetyl, and acetyloxy. Preferred are halogen atoms and trifluoromethyl. A chlorine atom and trifluoromethyl are more preferred.

"C$_{1-6}$ alkylcarbonyloxy" represented by R$_1$ and R$_{11}$ is optionally substituted, and substituents include halogen atoms, cyano, phenyl, trifluoromethoxy, and trifluoromethylthio.

"C$_{1-18}$ alkylcarbonyloxy" represented by R$_2$, R$_3$ and R$_4$, and R$_{12}$, R$_{13}$ and R$_{14}$ is preferably C$_{1-6}$ alkylcarbonyloxy, more preferably propionyloxy or cyclic C$_{3-6}$ alkylcarbonyloxy. The C$_{1-18}$ alkylcarbonyloxy group is optionally substituted, and substituents include halogen atoms, cyano, cyclic C$_{3-6}$alkyl, phenyl, trifluoromethoxy, trifluoromethylthio, pyridyl, and pyridylthio. More preferred are halogen atoms, cyclic C$_{3-6}$ alkyl, and pyridyl.

"C$_{2-6}$ alkenylcarbonyloxy" represented by R$_1$, R$_2$, R$_3$ and R$_4$, and R$_{11}$, R$_{12}$, R$_{13}$ and R$_{14}$ is optionally substituted, and substituents include halogen atoms, cyano, phenyl, trifluoromethoxy, and trifluoromethylthio.

"C$_{2-6}$ alkynylcarbonyloxy" represented by R$_1$, R$_2$, R$_3$ and R$_4$, and R$_{11}$, R$_{12}$, R$_{13}$ and R$_{14}$ is optionally substituted, and substituents include halogen atoms, cyano, phenyl, trifluoromethoxy, and trifluoromethylthio.

"C$_{1-6}$ alkyloxy" represented by R$_1$ and R$_4$, and R$_{11}$ and R$_{14}$ is optionally substituted, and substituents include halogen atoms; cyano; phenyl; trifluoromethoxy; trifluoromethylthio; C$_{1-6}$ alkylcarbonyl optionally substituted by a halogen atom; and C$_{1-6}$ alkylcarbonyloxy optionally substituted by a halogen atom.

"C$_{2-6}$ alkenyloxy" represented by R$_1$ and R$_4$, and R$_{11}$ and R$_{14}$ is optionally substituted, and substituents include halogen atoms; cyano; phenyl; trifluoromethoxy; trifluoromethylthio; C$_{1-6}$ alkylcarbonyl optionally substituted by a halogen atom; and C$_{1-6}$ alkylcarbonyloxy optionally substituted by a halogen atom.

"C$_{2-6}$ alkynyloxy" represented by R$_1$ and R$_4$, and R$_{11}$ and R$_{14}$ is optionally substituted, and substituents include halogen atoms; cyano; phenyl; trifluoromethoxy; trifluoromethylthio; C$_{1-6}$ alkylcarbonyl optionally substituted by a halogen atom; and C$_{1-6}$ alkylcarbonyloxy optionally substituted by a halogen atom.

Phenyl in "benzyloxy" represented by R$_1$ and R$_4$, and R$_{11}$ and R$_{14}$ is optionally substituted, and substituents include halogen atoms; C$_{1-6}$ alkyloxy optionally substituted by a halogen atom; C$_{1-6}$ alkyl optionally substituted by a halogen atom; C$_{1-6}$ alkylcarbonyl optionally substituted by a halogen atom; C$_{1-6}$ alkylcarbonyloxy optionally substituted by a halogen atom; C$_{1-6}$ alkylcarbonylamino optionally substituted by a halogen atom; C$_{1-6}$ alkylaminocarbonyloxy optionally substituted by a halogen atom; C$_{1-6}$ alkylaminocarbonyl optionally substituted by a halogen atom; C$_{1-6}$ alkylsulfonyloxy optionally substituted by a halogen atom; C$_{1-6}$ alkylthio optionally substituted by a halogen atom; C$_{1-6}$ alkylsulfinyl optionally substituted by a halogen atom; C$_{1-6}$ alkylsulfonyl optionally substituted by a halogen atom; cyano; formyl; azide; guanidyl; group —C(=NH)—NH$_2$; and group —CH=N—O—CH$_3$.

Phenyl in "benzoyloxy" represented by R$_2$, R$_3$ and R$_4$, and R$_{12}$, R$_{13}$ and R$_{14}$ is optionally substituted, and substituents include halogen atoms; C$_{1-6}$ alkyloxy optionally substituted by a halogen atom; $C_{1-6}$ alkyl optionally substituted by a halogen atom; $C_{1-6}$ alkylcarbonyl optionally substituted by a halogen atom; $C_{1-6}$ alkylcarbonyloxy optionally substituted by a halogen atom; $C_{1-6}$ alkylcarbonylamino optionally substituted by a halogen atom; $C_{1-6}$ alkylaminocarbonyloxy optionally substituted by a halogen atom; $C_{1-6}$ alkylaminocarbonyl optionally substituted by a halogen atom; $C_{1-6}$ alkylsulfonyloxy optionally substituted by a halogen atom; $C_{1-6}$ alkylthio optionally substituted by a halogen atom; $C_{1-6}$ alkylsulfinyl optionally substituted by a halogen atom; $C_{1-6}$ alkylsulfonyl optionally substituted by a halogen atom; cyano; nitro; formyl; azide; guanidyl; group —C(=NH)—NH$_2$; and group —CH=N—O—CH$_3$. Preferred are halogen atoms, $C_{1-6}$ alkyl substituted by a halogen atom, cyano, and nitro.

Phenyl in "benzenesulfonyloxy" represented by $R_3$ and $R_4$, and $R_{13}$ and $R_{14}$ is optionally substituted, and substituents include halogen atoms; $C_{1-6}$ alkyloxy optionally substituted by a halogen atom; $C_{1-6}$ alkyl optionally substituted by a halogen atom; $C_{1-6}$ alkylcarbonyl optionally substituted by a halogen atom; $C_{1-6}$ alkylcarbonyloxy optionally substituted by a halogen atom; $C_{1-6}$ alkylcarbonylamino optionally substituted by a halogen atom; $C_{1-6}$ alkylaminocarbonyloxy optionally substituted by a halogen atom; $C_{1-6}$ alkylaminocarbonyl optionally substituted by a halogen atom; $C_{1-6}$ alkylsulfonyloxy optionally substituted by a halogen atom; $C_{1-6}$ alkylthio optionally substituted by a halogen atom; $C_{1-6}$ alkylsulfinyl optionally substituted by a halogen atom; $C_{1-6}$ alkylsulfonyl optionally substituted by a halogen atom; cyano; formyl; azide; guanidyl; group —C(=NH)—NH$_2$; and group —CH=N—O—CH$_3$.

"$C_{1-6}$ alkylsulfonyloxy" represented by $R_2$, $R_3$ and $R_4$, and $R_{12}$, $R_{13}$ and $R_{14}$ is optionally substituted, and substituents include halogen atoms, cyano, phenyl, trifluoromethoxy, and trifluoromethylthio.

"$C_{1-6}$ alkyloxycarbonyloxy" represented by $R_4$ and $R_{14}$ is optionally substituted, and substituents include halogen atoms, cyano, phenyl, trifluoromethoxy, and trifluoromethylthio.

"$C_{1-6}$ alkylaminocarbonyloxy" represented by $R_4$ and $R_{14}$ is optionally substituted, and substituents include halogen atoms, cyano, phenyl, trifluoromethoxy, and trifluoromethylthio.

"Phenyl" represented by $R_2$' and $R_3$', and $R_{12}$' and $R_{13}$' and phenyl in "benzyl" represented by $R_2$' and $R_3$', and $R_{12}$' and $R_{13}$' is optionally substituted, and substituents include halogen atoms, $C_{1-4}$ alkyl, $C_{1-4}$ alkyloxy, nitro, cyano, formyl, trifluoromethoxy, acetyl, and acetyloxy.

"Saturated or unsaturated five- or six-membered heterocyclic ring" in "saturated or unsaturated five- or six-membered heterocyclic thiocarbonyloxy" represented by $R_3$ and $R_{13}$, and "saturated or unsaturated five- or six-membered heterocyclic oxy," "saturated or unsaturated five- or six-membered heterocyclic carbonyloxy," and "saturated or unsaturated five- or six-membered heterocyclic thiocarbonyloxy" represented by $R_4$ and $R_{14}$, is preferably, saturated or unsaturated five- or six-membered heterocyclic ring containing one to three heteroatoms selected from the group consisting of nitrogen, oxygen, and sulfur atoms, more preferably, saturated or unsaturated five- or six-membered heterocyclic ring containing one or two heteroatoms selected from the group consisting of nitrogen, oxygen, and sulfur atoms, more preferably, saturated or unsaturated five- or six-membered heterocyclic ring containing one or two nitrogen atoms, saturated or unsaturated five- or six-membered heterocyclic ring containing one or two oxygen atoms, saturated or unsaturated five- or six-membered heterocyclic ring containing one or two sulfur atoms, saturated or unsaturated five- or six-membered heterocyclic ring containing one nitrogen atom and one oxygen atom, or saturated or unsaturated five- or six-membered heterocyclic ring containing one nitrogen atom and one sulfur atom.

More specifically, examples of the "saturated or unsaturated five- or six-membered heterocyclic ring" include thienyl, furyl, pyrrolyl, imidazolyl, pyrazolyl, isothiazoyl, isoxazolyl, thiazolyl, oxazolyl, pyridyl, pyrimidinyl, pyrazinyl, pyridazinyl, tetrahydropyranyl, piperidinyl, piperazinyl, morpholinyl, and mannosyl. Preferred are pyridyl, furanyl, thiazolyl, imidazolyl, tetrahydropyranyl, and mannosyl. More specific examples thereof include (2- or 3-)thienyl, (2- or 3-)furyl, (1-, 2- or 3-)pyrrolyl, (1-, 2-, 4- or 5-)imidazolyl, (1-, 3-, 4- or 5-)pyrazolyl, (3-, 4- or 5-)isothiazoyl, (3-, 4- or 5-)isoxazolyl, (2-, 4- or 5-)thiazolyl, (2-, 4- or 5-)oxazolyl, (2-, 3- or 4-)pyridyl or, (2-, 4-, 5- or 6-)pyrimidinyl, (2- or 3-)pyrazinyl, (3- or 4-)pyridazinyl, (2-, 3- or 4-)tetrahydropyranyl, (1-, 2-, 3- or 4-)piperidinyl, (1-, 2- or 3-)piperazinyl, and (2-, 3- or 4-)morpholinyl, preferably 3-pyridyl, 2-franyl, 5-thiazolyl, 1-imidazolyl, 5-imidazolyl, and 2-tetrahydropyranyl, more preferably 2-tetrahydropyranyl, 2-pyrazinyl, and 3-pyridyl, particularly preferably 3-pyridyl.

The heterocyclic ring in the "saturated or unsaturated five- or six-membered heterocyclic carbonyloxy" and "saturated or unsaturated five- or six-membered heterocyclic thiocarbonyloxy" and "thieno[3,2-b]pyridylcarbonyloxy" and "1H-indolylcarbonyloxy" represented by $R_4$ and $R_{14}$ are optionally substituted, and substituents include halogen atoms, $C_{1-4}$ alkyl, $C_{1-4}$ alkyloxy, $C_{1-4}$ alkylthio, nitro, cyano, formyl, trifluoromethoxy, trifluoromethyl, trifluoromethylthio, trifluoromethylsulfinyl, trifluoromethylsulfonyl, acetyl, acetyloxy, benzoyl, and $C_{1-4}$ alkyloxycarbonyl. Preferred are halogen atoms, $C_{1-4}$ alkyl, $C_{1-4}$ alkyloxy, and trifluoromethyl.

The heterocyclic ring in the "saturated or unsaturated five- or six-membered heterocyclic oxy" is optionally substituted, and substituents include hydroxyl, benzyloxy, a halogen atom, $C_{1-4}$ alkyl, $C_{1-4}$ alkyloxy, nitro, cyano, formyl, trifluoromethoxy, trifluoromethyl, trifluoromethylthio, trifluoromethylsulfinyl, trifluoromethylsulfonyl, acetyl, and acetyloxy. Preferred are hydroxyl and benzyloxy.

A Composition for Use as a Pest Control Agent, Comprising a Compound Represented by Formula (I)

According to a preferred embodiment of the present invention, in the compound represented by formula (I), preferably, Het$_1$ represents 3-pyridyl.

Further, according to a preferred embodiment of the present invention, in the compound represented by formula (I), represents hydroxyl, $C_{1-6}$ alkylcarbonyloxy, $C_{1-3}$ alkyloxy, or benzyloxy, or oxo in the absence of a hydrogen atom at the 13-position, or the bond between 5-position and 13-position represents a double bond in the absence of $R_1$ and a hydrogen atom at the 5-position. More preferably, $R_1$ represents hydroxyl or $C_{1-6}$ alkylcarbonyloxy, or the bond between 5-position and 13-position represents a double bond in the absence of $R_1$ and a hydrogen atom at the 5-position, still more preferably $R_1$ represents hydroxyl.

According to a preferred embodiment of the present invention, in the compound represented by formula (I), $R_2$ represents hydroxyl, optionally substituted $C_{1-18}$ alkylcarbonyloxy, optionally substituted benzoyloxy, or $C_{1-3}$ alkylsulfonyloxy, more preferably optionally substituted $C_{1-18}$ alkylcarbonyloxy, still more preferably optionally substituted $C_{1-6}$ alkylcarbonyloxy, still more preferably straight chain or branched chain $C_{1-6}$ alkylcarbonyloxy (particularly propionyloxy) or optionally substituted cyclic $C_{3-6}$ alkylcarbonyloxy.

In a preferred embodiment of the present invention, in the compound represented by formula (I), $R_3$ represents a hydrogen atom, hydroxyl, optionally substituted $C_{1-18}$ alkylcarbonyloxy, optionally substituted benzoyloxy, $C_{1-6}$ alkylsulfonyloxy, optionally substituted benzenesulfonyloxy, or saturated or unsaturated five- or six-membered heterocyclic thiocarbonyloxy, more preferably optionally substituted $C_{1-6}$ alkylcarbonyloxy or $C_{1-6}$ alkylsulfonyloxy, still more preferably optionally substituted $C_{1-6}$ alkylcarbonyloxy, still more preferably straight chain or branched chain $C_{2-4}$ alkylcarbonyloxy (particularly propionyloxy) or optionally substituted cyclic $C_{3-6}$ alkylcarbonyloxy.

According to a preferred embodiment of the present invention, in the compound represented by formula (I), $R_2$ and $R_3$ together represent —O—$CR_2'R_3'$—O—, wherein $R_2'$ and $R_3'$, which may be the same or different, represent a hydrogen atom, $C_{1-6}$ alkyl, $C_{1-3}$ alkyloxy, $C_{2-3}$ alkenyl, benzyl, or optionally substituted phenyl, or $R_2'$ and $R_3'$ together represent oxo or $C_{2-6}$ alkylene. More preferably, $R_2$ and $R_3$ together represent —O—$CR_2'R_3'$—O—, wherein $R_2'$ and $R_3'$, which may be the same or different, represent a hydrogen atom, $C_{1-6}$ alkyl, or optionally substituted phenyl, or $R_2'$ and $R_3'$ together represent oxo or $C_{2-6}$ alkylene.

According to a preferred embodiment of the present invention, in the compound represented by formula (I), $R_4$ represents a hydrogen atom, hydroxyl, optionally substituted $C_{1-18}$ alkylcarbonyloxy, $C_{2-6}$ alkenylcarbonyloxy, $C_{2-6}$ alkynyl carbonyloxy, $C_{1-6}$ alkylsulfonyloxy, benzenesulfonyloxy, benzyloxy, $C_{1-3}$ alkyloxy, $C_{1-3}$ alkyloxy-$C_{1-3}$ alkyloxy, $C_{1-3}$ alkylthio-$C_{1-3}$ alkyloxy, $C_{1-3}$ alkyloxy-$C_{1-3}$ alkyloxy-$C_{1-3}$ alkyloxy, optionally substituted $C_{1-3}$ alkyloxycarbonyloxy, optionally substituted $C_{1-6}$ alkylaminocarbonyloxy, optionally substituted benzoyloxy, saturated or unsaturated five- or six-membered heterocyclic oxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, or saturated or unsaturated five- or six-membered heterocyclic thiocarbonyloxy, or oxo in the absence of a hydrogen atom at the 7-position. More preferably, $R_4$ represents hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, or saturated or unsaturated five- or six-membered heterocyclic thiocarbonyloxy, or oxo in the absence of a hydrogen atom at the 7-position. Still more preferably, $R_4$ represents hydroxyl, optionally substituted $C_{1-6}$ alkylcarbonyloxy, saturated or unsaturated five- or six-membered heterocyclic oxy, optionally substituted benzoyloxy, optionally substituted saturated or unsaturated five- or six-membered heterocyclic carbonyloxy, or saturated or unsaturated five- or six-membered heterocyclic thiocarbonyloxy. Still more preferably, $R_4$ represents hydroxyl, straight chain or branched chain $C_{2-4}$ alkylcarbonyloxy (particularly propionyloxy), optionally substituted cyclic $C_{3-6}$ alkylcarbonyloxy, or optionally substituted saturated or unsaturated five- or six-membered heterocyclic carbonyloxy.

According to another preferred embodiment of the present invention, in the compound represented by formula (I), $Het_1$ represents 3-pyridyl, $R_1$ represents hydroxyl or $C_{1-6}$ alkylcarbonyloxy, or the bond between 5-position and 13-position represents a double bond in the absence of $R_1$ and a hydrogen atom at the 5-position, $R_2$ represents optionally substituted $C_{1-6}$ alkylcarbonyloxy, $R_3$ represents optionally substituted $C_{1-6}$ alkylcarbonyloxy or $C_{1-6}$ alkylsulfonyloxy, or $R_2$ and $R_3$ together represent —O—$CR_2'R_3'$—O— wherein $R_2'$ and $R_3'$, which may be the same or different, represent a hydrogen atom, $C_{1-6}$ alkyl, or optionally substituted phenyl, or $R_2'$ and $R_3'$ together represent oxo or $C_{2-6}$ alkylene, and $R_4$ represents hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, saturated or unsaturated five- or six-membered heterocyclic thiocarbonyloxy, or oxo in the absence of a hydrogen atom at the 7-position.

According to another preferred embodiment of the present invention, in the compound represented by formula (I), $Het_1$ represents 3-pyridyl, $R_1$ represents hydroxyl, $R_2$ represents optionally substituted $C_{1-6}$ alkylcarbonyloxy, and $R_3$ represents optionally substituted $C_{1-6}$ alkylcarbonyloxy or $C_{1-6}$ alkylsulfonyloxy, and $R_4$ represents hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, saturated or unsaturated five- or six-membered heterocyclic thiocarbonyloxy, or oxo in the absence of a hydrogen atom at the 7-position.

According to another preferred embodiment of the present invention, in the compound represented by formula (I), $Het_1$ represents 3-pyridyl, $R_1$ represents hydroxyl, $R_2$ represents optionally substituted $C_{1-6}$ alkylcarbonyloxy, $R_3$ represents optionally substituted $C_{1-6}$ alkylcarbonyloxy or $C_{1-6}$ alkylsulfonyloxy, and $R_4$ represents hydroxyl, optionally substituted $C_{1-6}$ alkylcarbonyloxy, optionally substituted benzoyloxy, saturated or unsaturated five- or six-membered heterocyclic oxy, optionally substituted saturated or unsaturated five- or six-membered heterocyclic carbonyloxy, or saturated or unsaturated five- or six-membered heterocyclic thiocarbonyloxy.

According to another preferred embodiment of the present invention, in the compound represented by formula (I), $Het_1$ represents 3-pyridyl, $R_1$ represents hydroxyl, and $R_2$ and $R_3$ represent optionally substituted cyclic $C_{3-6}$ alkylcarbonyloxy.

According to another preferred embodiment of the present invention, in the compound represented by formula (I), $Het_1$ represents 3-pyridyl, $R_1$ represents hydroxyl or
  optionally substituted $C_{1-6}$ alkylcarbonyloxy or
  the bond between 5-position and 13-position represents a double bond in the absence of $R_1$ and a hydrogen atom at the 5-position, $R_2$ represents optionally substituted $C_{1-18}$ alkylcarbonyloxy or
  optionally substituted benzoyloxy, $R_3$ represents optionally substituted $C_{1-18}$ alkylcarbonyloxy or
  optionally substituted $C_{1-6}$ alkylsulfonyloxy, and $R_4$ represents hydroxyl,
  optionally substituted $C_{1-18}$ alkylcarbonyloxy,
  optionally substituted $C_{2-6}$ alkenylcarbonyloxy,
  optionally substituted benzoyloxy,
  optionally substituted $C_{1-6}$ alkylaminocarbonyloxy, optionally substituted saturated or unsaturated five- or six-membered heterocyclic oxy,
optionally substituted saturated or unsaturated five- or six-membered heterocyclic carbonyloxy,
optionally substituted thieno[3,2-b]pyridylcarbonyloxy
optionally substituted 1H-indolylcarbonyloxy, or
oxo in the absence of a hydrogen atom at the 7-position.

According to another preferred embodiment of the present invention, in the compound represented by formula (I), $Het_1$ represents 3-pyridyl,
$R_1$ represents hydroxyl or
optionally substituted $C_{1-6}$ alkylcarbonyloxy, or
the bond between 5-position and 13-position represents a double bond in the absence of R1 and a hydrogen atom at the 5-position,
$R_2$ represents optionally substituted $C_{1-18}$ alkylcarbonyloxy,
$R_3$ represents optionally substituted $C_{1-18}$ alkylcarbonyloxy or
optionally substituted $C_{1-6}$ alkylsulfonyloxy, and
$R_4$ represents hydroxyl,
optionally substituted $C_{1-18}$ alkylcarbonyloxy,
optionally substituted $C_{2-6}$ alkenylcarbonyloxy,
optionally substituted benzoyloxy,
optionally substituted $C_{1-6}$ alkylaminocarbonyloxy,
optionally substituted saturated or unsaturated five- or six-membered heterocyclic oxy,
optionally substituted saturated or unsaturated five- or six-membered heterocyclic carbonyloxy, or
oxo in the absence of a hydrogen atom at the 7-position.

According to another preferred embodiment of the present invention, in the compound represented by formula (I), $Het_1$ represents 3-pyridyl,
$R_1$ represents hydroxyl or
optionally substituted $C_{1-6}$ alkylcarbonyloxy, or
the bond between 5-position and 13-position represents a double bond in the absence of $R_1$ and a hydrogen atom at the 5-position,
$R_2$ represents optionally substituted $C_{1-18}$ alkylcarbonyloxy,
$R_3$ represents optionally substituted $C_{1-18}$ alkylcarbonyloxy,
$R_4$ represents hydroxyl,
optionally substituted $C_{1-18}$ alkylcarbonyloxy,
optionally substituted benzoyloxy,
optionally substituted saturated or unsaturated five- or six-membered heterocyclic oxy, or
optionally substituted saturated or unsaturated five- or six-membered heterocyclic carbonyloxy.

According to another preferred embodiment of the present invention, in the compound represented by formula (I), $Het_1$ represents 3-pyridyl, $R_1$ represents hydroxyl, $R_2$ represents $C_{1-6}$ alkylcarbonyloxy, and $R_3$ and/or $R_4$ represent $C_{2-4}$ alkylcarbonyloxy.

Further, an agriculturally and horticulturally acceptable salt of the compound represented by formula (I) include the same as that of the compound represented by formula (Ib) described below.

A Composition for Use as a Hemipteran Pest Control Agent, Comprising a Compound Represented by Formula (Ia)

According to a preferred embodiment of the present invention, in the compound represented by formula (Ia), preferably, $Het_2$ represents 3-pyridyl.

Further, according to a preferred embodiment of the present invention, in the compound represented by formula (Ia), $R_{11}$ represents hydroxyl, $C_{1-6}$ alkylcarbonyloxy, $C_{1-3}$ alkyloxy, or benzyloxy, or oxo in the absence of a hydrogen atom at the 13-position, or the bond between 5-position and 13-position represents a double bond in the absence of $R_{11}$ and a hydrogen atom at the 5-position. More preferably, $R_{11}$ represents hydroxyl or $C_{1-6}$ alkylcarbonyloxy, or the bond between 5-position and 13-position represents a double bond in the absence of $R_{11}$ and a hydrogen atom at the 5-position, still more preferably $R_{11}$ represents hydroxyl.

According to a preferred embodiment of the present invention, in the compound represented by formula (Ia), $R_{12}$ represents hydroxyl, optionally substituted $C_{1-18}$ alkylcarbonyloxy, optionally substituted benzoyloxy, or $C_{1-3}$ alkylsulfonyloxy, more preferably optionally substituted $C_{1-18}$ alkylcarbonyloxy, still more preferably optionally substituted $C_{1-6}$ alkylcarbonyloxy, still more preferably straight chain or branched chain $C_{1-6}$ alkylcarbonyloxy (particularly propionyloxy) or optionally substituted cyclic $C_{3-6}$ alkylcarbonyloxy.

In a preferred embodiment of the present invention, in the compound represented by formula (Ia), $R_{13}$ represents a hydrogen atom, hydroxyl, optionally substituted $C_{1-18}$ alkylcarbonyloxy, optionally substituted benzoyloxy, $C_{1-6}$ alkylsulfonyloxy, optionally substituted benzenesulfonyloxy, or saturated or unsaturated five- or six-membered heterocyclic thiocarbonyloxy, more preferably optionally substituted $C_{1-6}$ alkylcarbonyloxy or $C_{1-6}$ alkylsulfonyloxy, still more preferably optionally substituted $C_{1-6}$ alkylcarbonyloxy, still more preferably straight chain or branched chain $C_{2-4}$ alkylcarbonyloxy (particularly propionyloxy) or optionally substituted cyclic $C_{3-6}$ alkylcarbonyloxy.

According to a preferred embodiment of the present invention, in the compound represented by formula (Ia), $R_{12}$ and $R_{13}$ together represent —O—$CR_{12}'R_{13}'$—O—, wherein $R_{12}'$ and $R_{13}'$, which may be the same or different, represent a hydrogen atom, $C_{1-6}$ alkyl, $C_{1-3}$ alkyloxy, $C_{2-3}$ alkenyl, benzyl, or optionally substituted phenyl, or $R_{12}'$ and $R_{13}'$ together represent oxo or $C_{2-6}$ alkylene. More preferably, $R_{12}$ and $R_{13}$ together represent —O—$CR_{12}'R_{13}'$—O—, wherein $R_{12}'$ and $R_{13}'$, which may be the same or different, represent a hydrogen atom, $C_{1-6}$ alkyl, or optionally substituted phenyl, or $R_{12}'$ and $R_{13}'$ together represent oxo or $C_{2-6}$ alkylene.

According to a preferred embodiment of the present invention, in the compound represented by formula (Ia), $R_{14}$ represents a hydrogen atom, hydroxyl, optionally substituted $C_{1-16}$ alkylcarbonyloxy, $C_{2-6}$ alkenylcarbonyloxy, $C_{2-6}$ alkynyl carbonyloxy, $C_{1-6}$ alkylsulfonyloxy, benzenesulfonyloxy, benzyloxy, $C_{1-3}$ alkyloxy, $C_{1-3}$ alkyloxy-$C_{1-3}$ alkyloxy, $C_{1-3}$ alkylthio-$C_{1-3}$ alkyloxy, $C_{1-3}$ alkyloxy-$C_{1-3}$ alkyloxy-$C_{1-3}$ alkyloxy, optionally substituted $C_{1-3}$ alkyloxycarbonyloxy, optionally substituted $C_{1-6}$ alkylaminocarbonyloxy, optionally substituted benzoyloxy, saturated or unsaturated five- or six-membered heterocyclic oxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, or saturated or unsaturated five- or six-membered heterocyclic thiocarbonyloxy, or oxo in the absence of a hydrogen atom at the 7-position. More preferably, $R_{14}$ represents hydroxyl, optionally substituted $C_{1-6}$ alkylcarbonyloxy, optionally substituted benzoyloxy, saturated or unsaturated five- or six-membered heterocyclic oxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, or saturated or unsaturated five- or six-membered heterocyclic thiocarbonyloxy, or oxo in the absence of a hydrogen atom at the 7-position. Still more preferably, $R_{14}$ represents hydroxyl, optionally substituted $C_{1-6}$ alkylcarbonyloxy, saturated or unsaturated five- or six-membered heterocyclic oxy, optionally substituted benzoyloxy, optionally substituted saturated or unsaturated five- or six-membered heterocyclic carbonyloxy, or saturated or unsaturated five- or six-membered heterocyclic thiocarbonyloxy. Still more preferably, $R_{14}$ represents straight chain or branched chain $C_{2-4}$ alkylcarbonyloxy (particularly propionyloxy), optionally substituted cyclic $C_{3-6}$ alkylcarbonyloxy, or optionally substituted saturated or unsaturated five- or six-membered heterocyclic carbonyloxy.

According to another preferred embodiment of the present invention, in the compound represented by formula (Ia), $Het_2$ represents 3-pyridyl, $R_{11}$ represents hydroxyl or $C_{1-6}$ alkylcarbonyloxy, or the bond between 5-position and 13-position represents a double bond in the absence of $R_{11}$ and a hydrogen atom at the 5-position, $R_{12}$ represents optionally substituted $C_{1-6}$ alkylcarbonyloxy, $R_{13}$ represents optionally substituted $C_{1-6}$ alkylcarbonyloxy or $C_{1-6}$ alkylsulfonyloxy, or $R_{12}$ and $R_{13}$ together represent —O—$CR_{12}'R_{13}'$—O— wherein $R_{12}'$ and $R_{13}'$, which may be the same or different, represent a hydrogen atom, $C_{1-6}$ alkyl, or optionally substituted phenyl, or $R_{12}'$ and $R_{13}'$ together represent oxo or $C_{2-6}$ alkylene, and $R_{14}$ represents hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, saturated or unsaturated five- or six-membered heterocyclic thiocarbonyloxy, or oxo in the absence of a hydrogen atom at the 7-position.

According to another preferred embodiment of the present invention, in the compound represented by formula (Ia), $Het_2$ represents 3-pyridyl, $R_{11}$ represents hydroxyl, $R_{12}$ represents optionally substituted $C_{1-6}$ alkylcarbonyloxy, and $R_{13}$ represents optionally substituted $C_{1-6}$ alkylcarbonyloxy or $C_{1-6}$ alkylsulfonyloxy, and $R_{14}$ represents hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, saturated or unsaturated five- or six-membered heterocyclic thiocarbonyloxy, or oxo in the absence of a hydrogen atom at the 7-position.

According to another preferred embodiment of the present invention, in the compound represented by formula (Ia), $Het_2$ represents 3-pyridyl, $R_{11}$ represents hydroxyl, $R_{12}$ represents optionally substituted $C_{1-6}$ alkylcarbonyloxy, $R_{13}$ represents optionally substituted $C_{1-6}$ alkylcarbonyloxy or $C_{1-6}$ alkylsulfonyloxy, and $R_{14}$ represents hydroxyl, optionally substituted $C_{1-6}$ alkylcarbonyloxy, optionally substituted benzoyloxy, saturated or unsaturated five- or six-membered heterocyclic oxy, optionally substituted saturated or unsaturated five- or six-membered heterocyclic carbonyloxy, or saturated or unsaturated five- or six-membered heterocyclic thiocarbonyloxy.

According to another preferred embodiment of the present invention, in the compound represented by formula (Ia), $Het_2$ represents 3-pyridyl, $R_{11}$ represents hydroxyl, and $R_{12}$ and $R_{13}$ represent optionally substituted cyclic $C_{3-6}$ alkylcarbonyloxy.

According to another preferred embodiment of the present invention, in the compound represented by formula (Ia),
$Het_2$ represents 3-pyridyl,
$R_{11}$ represents hydroxyl or
optionally substituted $C_{1-6}$ alkylcarbonyloxy, or
the bond between 5-position and 13-position represents a double bond in the absence of $R_{11}$ and a hydrogen atom at the 5-position,
$R_{12}$ represents optionally substituted $C_{1-18}$ alkylcarbonyloxy or
optionally substituted benzoyloxy,
$R_{13}$ represents optionally substituted $C_{1-18}$ alkylcarbonyloxy or
optionally substituted $C_{1-6}$ alkylsulfonyloxy, and
$R_{14}$ represents hydroxyl,
optionally substituted $C_{1-18}$ alkylcarbonyloxy,
optionally substituted $C_{2-6}$ alkenylcarbonyloxy,
optionally substituted benzoyloxy,
optionally substituted $C_{1-6}$ alkylaminocarbonyloxy,
optionally substituted saturated or unsaturated five- or six-membered heterocyclic oxy,
optionally substituted saturated or unsaturated five- or six-membered heterocyclic carbonyloxy,
optionally substituted thieno[3,2-b]pyridylcarbonyloxy,
optionally substituted 1H-indolylcarbonyloxy, or
oxo in the absence of a hydrogen atom at the 7-position.

According to another preferred embodiment of the present invention, in the compound represented by formula (Ia),
$Het_2$ represents 3-pyridyl,
$R_{11}$ represents hydroxyl or
optionally substituted $C_{1-6}$ alkylcarbonyloxy, or
the bond between 5-position and 13-position represents a double bond in the absence of $R_{11}$ and a hydrogen atom at the 5-position,
$R_{12}$ represents optionally substituted $C_{1-18}$ alkylcarbonyloxy,
$R_{13}$ represents optionally substituted $C_{1-18}$ alkylcarbonyloxy or
optionally substituted $C_{1-6}$ alkylsulfonyloxy, and
$R_{14}$ represents hydroxyl,
optionally substituted $C_{1-18}$ alkylcarbonyloxy,
optionally substituted $C_{2-6}$ alkenylcarbonyloxy,
optionally substituted benzoyloxy,
optionally substituted $C_{1-6}$ alkylaminocarbonyloxy,
optionally substituted saturated or unsaturated five- or six-membered heterocyclic oxy,
optionally substituted saturated or unsaturated five- or six-membered heterocyclic carbonyloxy, or
oxo in the absence of a hydrogen atom at the 7-position.

According to another preferred embodiment of the present invention, in the compound represented by formula (Ia),
$Het_2$ represents 3-pyridyl,
$R_{11}$ represents hydroxyl or
optionally substituted $C_{1-6}$ alkylcarbonyloxy, or
the bond between 5-position and 13-position represents a double bond in the absence of $R_{11}$ and a hydrogen atom at the 5-position,
$R_{12}$ represents optionally substituted $C_{1-18}$ alkylcarbonyloxy,
$R_{13}$ represents optionally substituted $C_{1-18}$ alkylcarbonyloxy,
$R_{14}$ represents hydroxyl,
optionally substituted $C_{1-18}$ alkylcarbonyloxy,
optionally substituted benzoyloxy,
optionally substituted saturated or unsaturated five- or six-membered heterocyclic oxy, or optionally substituted saturated or unsaturated five- or six-membered heterocyclic carbonyloxy.

According to another preferred embodiment of the present invention, in the compound represented by formula (Ia), $Het_2$ represents 3-pyridyl, $R_{11}$ represents hydroxyl, $R_{12}$ represents $C_{1-6}$ alkylcarbonyloxy, and $R_{13}$ and/or $R_{14}$ represent $C_{2-4}$ alkylcarbonyloxy.

Further, an agriculturally and horticulturally acceptable salt of the compound represented by formula (Ia) include the same as that of the compound represented by formula (Ib) described below.

Compounds of Formula (Ib) or its Agriculturally and Horticulturally Acceptable Salts Compounds of formula (Ib) are novel pyripyropene derivatives that are comprised as a part in the compound represented by formula (I). In particular, they have significant insecticidal activity.

According to an embodiment of the present invention, there is provided the compounds of formula (Ib), excluding a compound wherein $Het_1$ represents 3-pyridyl, $R_1$ represents hydroxyl, and $R_2$ and $R_3$ represent propionyloxy, and $R_4$ represents hydroxyl.

According to another preferred embodiment of the present invention, in the compound represented by formula (Ib), $R_2$ and $R_3$ represent optionally substituted cyclic $C_{3-6}$ alkylcarbonyloxy, $R_4$ represents hydroxyl, optionally substituted cyclic $C_{3-6}$ alkylcarbonyloxy, or optionally substituted benzoyloxy. Alternatively, $R_2$ and $R_3$ represent propionyloxy, $R_4$ represents optionally substituted cyclic $C_{3-6}$ alkylcarbonyloxy, or optionally substituted saturated or unsaturated five- or six-membered heterocyclic carbonyloxy.

According to another preferred embodiment of the present invention, in the compounds represented by formula (Ib), $R_2$ and $R_3$ represent optionally substituted cyclic $C_{3-6}$ alkylcarbonyloxy, $R_4$ represents hydroxyl, optionally substituted cyclic $C_{3-6}$ alkylcarbonyloxy, or optionally substituted benzoyloxy.

According to another preferred embodiment of the present invention, in the compounds represented by formula (Ib), $R_2$ and $R_3$ represent propionyloxy, $R_4$ represents optionally substituted cyclic $C_{3-6}$ alkylcarbonyloxy or optionally substituted saturated or unsaturated five- or six-membered heterocyclic carbonyloxy.

According to still another preferred embodiment of the present invention, there is provided a pest control agent comprising a compound represented by formula (Ib) or an agriculturally and horticulturally acceptable salt thereof as an active ingredient.

Agriculturally and horticulturally acceptable salts in the compounds of formula (Ib) include, for example, acid addition salts such as hydrochlorides, nitrates, sulfates, phosphates, or acetates.

Specific examples of the compounds represented by formula (I), (Ia), or (Ib) include compounds shown in Tables 1 to 14 below. In the following tables, H(=) means that the bond between 5-position and 13-position represents a double bond in the absence of $R_1$ and a hydrogen atom at the 5-position

TABLE 1

| Compound No. | $R_1$ | $R_2$ | $R_3$ | $R_4$ | $Het_1$ |
|---|---|---|---|---|---|
| 1 | OH | $OCOCH_3$ | $OCOCH_3$ | $OCOCH_2CH_3$ | 3-pyridyl |
| 2 | OH | $OCOCH_3$ | $OCOCH_3$ | $OCOCH_2CF_3$ | 3-pyridyl |
| 3 | OH | $OCOCH_3$ | $OCOCH_3$ | $OCOCH_2OCH_3$ | 3-pyridyl |
| 4 | OH | $OCOCH_3$ | $OCOCH_3$ | $OCOCH_2OCOCH_3$ | 3-pyridyl |
| 5 | OH | $OCOCH_3$ | $OCOCH_3$ | $OCOCH_2CH_2CN$ | 3-pyridyl |
| 6 | OH | $OCOCH_3$ | $OCOCH_3$ | $OCO(CH_2)_2CH_3$ | 3-pyridyl |
| 7 | OH | $OCOCH_3$ | $OCOCH_3$ | $OCO(CH_2)_3CH_3$ | 3-pyridyl |
| 8 | OH | $OCOCH_3$ | $OCOCH_3$ | $OCO(CH_2)_4CH_3$ | 3-pyridyl |
| 9 | OH | $OCOCH_3$ | $OCOCH_3$ | $OCO(CH_2)_5CH_3$ | 3-pyridyl |
| 10 | OH | $OCOCH_3$ | $OCOCH_3$ | $OCO(CH_2)_6CH_3$ | 3-pyridyl |
| 11 | OH | $OCOCH_3$ | $OCOCH_3$ | $OCO(CH_2)_{16}CH_3$ | 3-pyridyl |
| 12 | OH | $OCOCH_3$ | $OCOCH_3$ | $OCOCH(CH_3)_2$ | 3-pyridyl |
| 13 | OH | $OCOCH_3$ | $OCOCH_3$ | $OCOC(CH_3)_3$ | 3-pyridyl |
| 14 | OH | $OCOCH_3$ | $OCOCH_3$ | $OCOCH_2CH(CH_3)_2$ | 3-pyridyl |
| 15 | OH | $OCOCH_3$ | $OCOCH_3$ | $OCO(CH_2)_2CH(CH_3)_2$ | 3-pyridyl |
| 16 | OH | $OCOCH_3$ | $OCOCH_3$ | OCO-trans-$CH=CHCH_2CH_3$ | 3-pyridyl |
| 17 | OH | $OCOCH_3$ | $OCOCH_3$ | $OCOCH_2C\equiv CCH_3$ | 3-pyridyl |
| 18 | OH | $OCOCH_3$ | $OCOCH_3$ | $OCOC\equiv CCH_2CH_3$ | 3-pyridyl |
| 19 | OH | $OCOCH_3$ | $OCOCH_3$ | $OCO(CH_2)_2C\equiv CH$ | 3-pyridyl |
| 20 | OH | $OCOCH_3$ | $OCOCH_3$ | $OCO(CH_2)_2CH=CH_2$ | 3-pyridyl |

TABLE 2

| Compound No. | $R_1$ | $R_2$ | $R_3$ | $R_4$ | $Het_1$ |
|---|---|---|---|---|---|
| 21 | OH | $OCOCH_3$ | $OCOCH_3$ | $OCOCH_2C_6H_5$ | 3-pyridyl |
| 22 | OH | $OCOCH_3$ | $OCOCH_3$ | $OCO(CH_2)_2C_6H_5$ | 3-pyridyl |
| 23 | OH | $OCOCH_3$ | $OCOCH_3$ | $OCOC_6H_5$ | 3-pyridyl |
| 24 | OH | $OCOCH_3$ | $OCOCH_3$ | OCO-(4-Br—$C_6H_4$) | 3-pyridyl |
| 25 | OH | $OCOCH_3$ | $OCOCH_3$ | OCO-(4-$N_3$—$C_6H_4$) | 3-pyridyl |
| 26 | OH | $OCOCH_3$ | $OCOCH_3$ | OCO-(4-$OCF_3$—$C_6H_4$) | 3-pyridyl |
| 27 | OH | $OCOCH_3$ | $OCOCH_3$ | OCO-(4-$SO_2CF_3$—$C_6H_4$) | 3-pyridyl |
| 28 | OH | $OCOCH_3$ | $OCOCH_3$ | OCO-(3-pyridyl) | 3-pyridyl |
| 29 | OH | $OCOCH_3$ | $OCOCH_3$ | OCO-(2-Cl-3-pyridyl) | 3-pyridyl |
| 30 | OH | $OCOCH_3$ | $OCOCH_3$ | OCO-(2-franyl) | 3-pyridyl |
| 31 | OH | $OCOCH_3$ | $OCOCH_3$ | OCO-(2-thiazolyl) | 3-pyridyl |

TABLE 2-continued

| Compound No. | $R_1$ | $R_2$ | $R_3$ | $R_4$ | $Het_1$ |
|---|---|---|---|---|---|
| 32 | OH | $OCOCH_3$ | $OCOCH_3$ | OCO-(2-Cl-5-thiazolyl) | 3-pyridyl |
| 33 | OH | $OCOCH_3$ | $OCOCH_3$ | OCO-(5-imidazolyl) | 3-pyridyl |
| 34 | OH | $OCOCH_3$ | $OCOCH_3$ | OCS-(1-imidazolyl) | 3-pyridyl |
| 35 | OH | $OCOCH_3$ | $OCOCH_3$ | $OCOOCH_2C_6H_5$ | 3-pyridyl |
| 36 | OH | $OCOCH_3$ | $OCOCH_3$ | $OSO_2CH_3$ | 3-pyridyl |
| 37 | OH | $OCOCH_3$ | $OCOCH_3$ | $OSO_2C_6H_5$ | 3-pyridyl |
| 38 | OH | $OCOCH_3$ | $OCOCH_3$ | $OCONHCH_2CH_3$ | 3-pyridyl |
| 39 | OH | $OCOCH_3$ | $OCOCH_3$ | $OCONH(CH_2)_2CH_3$ | 3-pyridyl |
| 40 | OH | $OCOCH_3$ | $OCOCH_3$ | $OCONHCH_2C_6H_5$ | 3-pyridyl |

TABLE 3

| Compound No. | $R_1$ | $R_2$ | $R_3$ | $R_4$ | $Het_1$ |
|---|---|---|---|---|---|
| 41 | OH | $OCOCH_3$ | $OCOCH_3$ | $OCH_2C_6H_5$ | 3-pyridyl |
| 42 | OH | $OCOCH_3$ | $OCOCH_3$ | $OCH_2SCH_3$ | 3-pyridyl |
| 43 | OH | $OCOCH_3$ | $OCOCH_3$ | $OCH_2OCH_3$ | 3-pyridyl |
| 44 | OH | $OCOCH_3$ | $OCOCH_3$ | $OCH_2OCH_2CH_2OCH_3$ | 3-pyridyl |
| 45 | OH | $OCOCH_3$ | $OCOCH_3$ | O-(2-tetrahydropyranyl) | 3-pyridyl |
| 46 | OH | $OCOCH_3$ | $OCOCH_3$ | O-(tetra-O-benzyl-mannosyl) | 3-pyridyl |
| 47 | OH | $OCOCH_3$ | $OCOCH_3$ | H | 3-pyridyl |
| 48 | OH | $OCOCH_3$ | $OCOCH_3$ | $OCO$-c-$C_3H_5$ | 3-pyridyl |
| 49 | OH | $OCOCH_3$ | $OCOCH_3$ | OH | 3-pyridyl |
| 50 | OH | $OCOCH_3$ | $OCOCH_3$ | =O | 3-pyridyl |
| 51 | OH | $OCOCH_3$ | $OCOCH2CH3$ | $OCOCH_3$ | 3-pyridyl |
| 52 | OH | $OCOCH_3$ | $OCOCH2CH3$ | $OCOCH_2CH_3$ | 3-pyridyl |
| 53 | OH | $OCOCH_3$ | $OCOCH_2CH_3$ | H | 3-pyridyl |
| 54 | OH | $OCOCH_3$ | $OCO(CH_2)_2CH_3$ | $OCOCH_3$ | 3-pyridyl |
| 55 | OH | $OCOCH_3$ | $OCO(CH_2)_2CH_3$ | OH | 3-pyridyl |
| 56 | OH | $OCOCH_3$ | $OCO(CH_2)_3CH_3$ | $OCOCH_3$ | 3-pyridyl |
| 57 | OH | $OCOCH_3$ | $OCOCH(CH_3)_2$ | $OCOCH_3$ | 3-pyridyl |
| 58 | OH | $OCOCH_3$ | $OCOC_6H_5$ | $OCOCH_3$ | 3-pyridyl |
| 59 | OH | $OCOCH_3$ | $OCOC_6H_5$ | OH | 3-pyridyl |
| 60 | OH | $OCOCH_3$ | OCS-(1-imidazolyl) | $OCOCH_3$ | 3-pyridyl |

TABLE 4

| Compound No. | $R_1$ | $R_2$ | $R_3$ | $R_4$ | $Het_1$ |
|---|---|---|---|---|---|
| 61 | OH | $OCOCH_3$ | $OSO_2CH_3$ | $OCOCH_3$ | 3-pyridyl |
| 62 | OH | $OCOCH_3$ | $OSO_2CH_3$ | $OCO(CH_2)_3CH_3$ | 3-pyridyl |
| 63 | OH | $OCOCH_3$ | $OSO_2C_6H_5$ | $OCOCH_3$ | 3-pyridyl |
| 64 | OH | $OCOCH_3$ | $OSO_2CH_2CH_3$ | $OCOCH_3$ | 3-pyridyl |
| 65 | OH | $OCOCH_3$ | $OSO_2CH_2CH_2CH_3$ | $OCOCH_3$ | 3-pyridyl |
| 66 | OH | $OCOCH_3$ | $OSO_2CH_2CH_3$ | OH | 3-pyridyl |
| 67 | OH | $OCOCH_3$ | $OSO_2CH_2CH_2CH_3$ | OH | 3-pyridyl |
| 68 | OH | $OCOCH_3$ | OH | OH | 3-pyridyl |
| 69 | OH | $OCOCH_3$ | OH | $OCOCH_3$ | 3-pyridyl |
| 70 | OH | $OCOCH_3$ | H | H | 3-pyridyl |
| 71 | OH | $OCOCH_3$ | H | $OCOCH_2CH_3$ | 3-pyridyl |
| 72 | OH | $OCOCH_2CH_3$ | $OCOCH_3$ | $OCOCH_3$ | 3-pyridyl |
| 73 | OH | $OCOCH_2CH_3$ | $OCOCH_2CH_3$ | OH | 3-pyridyl |
| 74 | OH | $OCOCH_2CH_3$ | $OCOCH_2CH_3$ | $OCOCH_3$ | 3-pyridyl |
| 75 | OH | $OCOCH_2CH_3$ | $OCOCH_3$ | $OCOCH_2CH_3$ | 3-pyridyl |
| 76 | OH | $OCOCH_2CH_3$ | $OCOCH_2CH_3$ | $OCOCH_2CH_3$ | 3-pyridyl |
| 77 | OH | $OCOCH_2CH_3$ | $OCOCH_2CH_3$ | $OCOC_6H_5$ | 3-pyridyl |
| 78 | OH | $OCOCH_2CH_3$ | $OCOCH_2CH_3$ | H | 3-pyridyl |
| 79 | OH | $OCOCH_2CH_3$ | H | H | 3-pyridyl |
| 80 | OH | $OCO(CH_2)_2CH_3$ | $OCOCH_3$ | $OCOCH_3$ | 3-pyridyl |

TABLE 5

| Compound No. | $R_1$ | $R_2$ | $R_3$ | $R_4$ | $Het_1$ |
|---|---|---|---|---|---|
| 81 | OH | $OCO(CH_2)_2CH_3$ | $OCO(CH_2)_2CH_3$ | OH | 3-pyridyl |
| 82 | OH | $OCO(CH_2)_2CH_3$ | $OCO(CH_2)_2CH_3$ | $OCO(CH_2)_2CH_3$ | 3-pyridyl |
| 83 | OH | $OCO(CH_2)_2CH_3$ | $OCO(CH_2)_2CH_3$ | $OCOCH_3$ | 3-pyridyl |

TABLE 5-continued

| Compound No. | R$_1$ | R$_2$ | R$_3$ | R$_4$ | Het$_1$ |
|---|---|---|---|---|---|
| 84 | OH | OCO(CH$_2$)$_3$CH$_3$ | OCOCH$_3$ | OCOCH$_3$ | 3-pyridyl |
| 85 | OH | OCO(CH$_2$)$_3$CH$_3$ | OCO(CH$_2$)$_3$CH$_3$ | OCO(CH$_2$)$_3$CH$_3$ | 3-pyridyl |
| 86 | OH | OCO(CH$_2$)$_3$CH$_3$ | OSO$_2$CH$_3$ | OCO(CH$_2$)$_3$CH$_3$ | 3-pyridyl |
| 87 | OH | OCO(CH$_2$)$_3$CH$_3$ | OSO$_2$CH$_3$ | OH | 3-pyridyl |
| 88 | OH | OCO(CH$_2$)$_{16}$CH$_3$ | OCO(CH$_2$)$_{16}$CH$_3$ | OCO(CH$_2$)$_{16}$CH$_3$ | 3-pyridyl |
| 89 | OH | OCOCH(CH$_3$)$_2$ | OCOCH$_3$ | OCOCH$_3$ | 3-pyridyl |
| 90 | OH | OCOCH(CH$_3$)$_2$ | OCOCH(CH$_3$)$_2$ | OCOCH(CH$_3$)$_2$ | 3-pyridyl |
| 91 | OH | OCOC(CH$_3$)$_3$ | OCOC(CH$_3$)$_3$ | OCOC(CH$_3$)$_3$ | 3-pyridyl |
| 92 | OH | OCOC$_6$H$_5$ | OCOCH$_3$ | OCOCH$_3$ | 3-pyridyl |
| 93 | OH | OCOC$_6$H$_5$ | OSO$_2$CH$_3$ | OH | 3-pyridyl |
| 94 | OH | OCOC$_6$H$_5$ | OSO$_2$CH$_3$ | OCOCH$_3$ | 3-pyridyl |
| 95 | OH | OCOC$_6$H$_5$ | OSO$_2$CH$_3$ | OCO(CH$_2$)$_3$CH$_3$ | 3-pyridyl |
| 96 | OH | OCO-(4-Br—C$_6$H$_4$) | OCO-(4-Br—C$_6$H$_4$) | OCO-(4-Br—C$_6$H$_4$) | 3-pyridyl |
| 97 | OH | OCO-(4-N$_3$—C$_6$H$_4$) | OSO$_2$CH$_3$ | OCOCH$_3$ | 3-pyridyl |
| 98 | OH | OSO$_2$CH$_3$ | OSO$_2$CH$_3$ | OH | 3-pyridyl |
| 99 | OH | OSO$_2$CH$_3$ | OSO$_2$CH$_3$ | OSO$_2$CH$_3$ | 3-pyridyl |
| 100 | OH | OSO$_2$CH$_3$ | OSO$_2$CH$_3$ | OCOCH$_3$ | 3-pyridyl |

TABLE 6

| Compound No. | R$_1$ | R$_2$ | R$_3$ | R$_4$ | Het$_1$ |
|---|---|---|---|---|---|
| 101 | OH | OSO$_2$CH$_3$ | OH | OH | 3-pyridyl |
| 102 | OH | OH | OH | OH | 3-pyridyl |
| 103 | OH | OH | OH | OCOCH$_3$ | 3-pyridyl |
| 104 | OH | OH | OH | OCO(CH$_2$)$_3$CH$_3$ | 3-pyridyl |
| 105 | OH | OH | OH | OCH$_2$OCH$_2$CH$_2$OCH$_3$ | 3-pyridyl |
| 106 | OH | OH | OCOCH$_3$ | OH | 3-pyridyl |
| 107 | OH | OH | OCOCH$_2$CH$_3$ | OH | 3-pyridyl |
| 108 | OH | OH | OCO(CH$_2$)$_2$CH$_3$ | OH | 3-pyridyl |
| 109 | OH | OH | OCO(CH$_2$)$_3$CH$_3$ | OH | 3-pyridyl |
| 110 | OH | OH | OCOCH(CH$_3$)$_2$ | OH | 3-pyridyl |
| 111 | OH | OH | OSO$_2$CH$_3$ | OH | 3-pyridyl |
| 112 | OH | OH | OSO$_2$CH$_2$CH$_3$ | OH | 3-pyridyl |
| 113 | OH | OH | OSO$_2$CH$_2$CH$_2$CH$_3$ | OH | 3-pyridyl |
| 114 | OH | OH | OSO$_2$CH(CH$_3$)$_2$ | OH | 3-pyridyl |
| 115 | OH | OH | OSO$_2$C$_6$H$_5$ | OH | 3-pyridyl |
| 116 | OH | OH | OSO$_2$-(4-CH$_3$—C$_6$H$_4$) | OH | 3-pyridyl |
| 117 | OH | OH | OCO-(4-Br—C$_6$H$_4$) | OH | 3-pyridyl |
| 118 | OH | OH | OCO(CH$_2$)$_3$CH$_3$ | OCO(CH$_2$)$_3$CH$_3$ | 3-pyridyl |
| 119 | OH | OH | OSO$_2$CH$_3$ | OSO$_2$CH$_3$ | 3-pyridyl |
| 120 | OH | OH | OSO$_2$CH$_3$ | OCOCH$_3$ | 3-pyridyl |

TABLE 7

| Compound No. | R$_1$ | R$_2$ | R$_3$ | R$_4$ | Het$_1$ |
|---|---|---|---|---|---|
| 121 | OH | OH | OSO$_2$CH$_3$ | OCOCH$_3$ | 3-pyridyl |
| 122 | OH | OH | OSO$_2$CH$_3$ | OCO(CH$_2$)$_3$CH$_3$ | 3-pyridyl |
| 123 | OH | OH | OSO$_2$C$_6$H$_5$ | OCOCH$_3$ | 3-pyridyl |
| 124 | OH | OH | OSO$_2$C$_6$H$_5$ | OSO$_2$C$_6$H$_5$ | 3-pyridyl |
| 125 | OH | —O—CH(CH$_3$)—O— | | OCO(CH$_2$)$_3$CH$_3$ | 3-pyridyl |
| 126 | OH | —O—CH(C$_2$H$_5$)—O— | | OH | 3-pyridyl |
| 127 | OH | —O—CH(C$_2$H$_5$)—O— | | OCO(CH$_2$)$_3$CH$_3$ | 3-pyridyl |
| 128 | OH | —O—CH(CH=CH$_2$)—O— | | OH | 3-pyridyl |
| 129 | OH | —O—CH(CH=CH$_2$)—O— | | OCO(CH$_2$)$_3$CH$_3$ | 3-pyridyl |
| 130 | OH | —O—CH(CH(CH$_3$)$_2$)—O— | | OH | 3-pyridyl |
| 131 | OH | —O—CH(CH(CH$_3$)$_2$)—O— | | OCO(CH$_2$)$_3$CH$_3$ | 3-pyridyl |
| 132 | OH | —O—CH(OCH$_3$)—O— | | OH | 3-pyridyl |
| 133 | OH | —O—CH(C(CH$_3$)$_3$)—O— | | OCO(CH$_2$)$_3$CH$_3$ | 3-pyridyl |
| 134 | OH | —O—CH(CH$_2$C$_6$H$_5$)—O— | | OH | 3-pyridyl |
| 135 | OH | —O—C(CH$_3$)$_2$—O— | | OH | 3-pyridyl |
| 136 | OH | —O—C(CH$_3$)$_2$—O— | | OCOCH$_3$ | 3-pyridyl |
| 137 | OH | —O—C(CH$_3$)$_2$—O— | | OCO(CH$_2$)$_3$CH$_3$ | 3-pyridyl |
| 138 | OH | —O—C(CH$_3$)(C$_6$H$_5$)—O— | | OH | 3-pyridyl |
| 139 | OH | —O—C(CH$_3$)(C$_6$H$_5$)—O— | | OCO(CH$_2$)$_3$CH$_3$ | 3-pyridyl |
| 140 | OH | —O—CH(C$_6$H$_5$)—O— | | OH | 3-pyridyl |

TABLE 8

| Compound No. | R$_1$ | R$_2$ | R$_3$ | R$_4$ | Het$_1$ |
|---|---|---|---|---|---|
| 141 | OH | | —O—CH(C$_6$H$_5$)—O— | OCOCH$_3$ | 3-pyridyl |
| 142 | OH | | —O—CH(OCH$_3$)—O— | OCO(CH$_2$)$_3$CH$_3$ | 3-pyridyl |
| 143 | OH | | —O—CH(C$_6$H$_5$)—O— | OCO(CH$_2$)$_3$CH$_3$ | 3-pyridyl |
| 144 | OH | | —O—CH(3-CH$_3$—C$_6$H$_4$)—O— | OH | 3-pyridyl |
| 145 | OH | | —O—CH(3-CH$_3$—C$_6$H$_4$)—O— | OCO(CH$_2$)$_3$CH$_3$ | 3-pyridyl |
| 146 | OH | | —O—CH(2-CH$_3$—C$_6$H$_4$)—O— | OH | 3-pyridyl |
| 147 | OH | | —O—CH(4-CH$_3$—C$_6$H$_4$)—O— | OCO(CH$_2$)$_3$CH$_3$ | 3-pyridyl |
| 148 | OH | | —O—CH(3-F—C$_6$H$_4$)—O— | OH | 3-pyridyl |
| 149 | OH | | —O—CH(2-F—C$_6$H$_4$)—O— | OCO(CH$_2$)$_3$CH$_3$ | 3-pyridyl |
| 150 | OH | | —O—CH(4-F—C$_6$H$_4$)—O— | OCO(CH$_2$)$_3$CH$_3$ | 3-pyridyl |
| 151 | OH | | —O—CH(4-NO$_2$—C$_6$H$_4$)—O— | OH | 3-pyridyl |
| 152 | OH | | —O—CH(4-NO$_2$—C$_6$H$_4$)—O— | OCO(CH$_2$)$_3$CH$_3$ | 3-pyridyl |
| 153 | OH | | —O—CH(4-OCH$_3$—C$_6$H$_4$)—O— | OH | 3-pyridyl |
| 154 | OH | | —O—CH(4-OCH$_3$—C$_6$H$_4$)—O— | OCO(CH$_2$)$_3$CH$_3$ | 3-pyridyl |
| 155 | OH | | —O—C(spiro-c-C$_5$H$_8$)—O— | OH | 3-pyridyl |
| 156 | OH | | —O—C(spiro-c-C$_5$H$_8$)—O— | OCO(CH$_2$)$_3$CH$_3$ | 3-pyridyl |
| 157 | OH | | —O—C(spiro-c-C$_6$H$_{10}$)—O— | OH | 3-pyridyl |
| 158 | OH | | —O—C(spiro-c-C$_6$H$_{10}$)—O— | OCO(CH$_2$)$_3$CH$_3$ | 3-pyridyl |
| 159 | OH | | —O—CO—O— | OH | 3-pyridyl |
| 160 | OH | | —O—CO—O— | OCO-1-imidazolyl | 3-pyridyl |

TABLE 9

| Compound No. | R$_1$ | R$_2$ | R$_3$ | R$_4$ | Het$_1$ |
|---|---|---|---|---|---|
| 161 | OH | | —O—CO—O— | OCO(CH$_2$)$_3$CH$_3$ | 3-pyridyl |
| 162 | OCOCH$_3$ | OCOCH$_3$ | OCOCH$_3$ | OCOCH$_3$ | 3-pyridyl |
| 163 | OCOCH$_3$ | OCOCH$_3$ | OCOCH$_3$ | OH | 3-pyridyl |
| 164 | OCOCH$_3$ | OCOCH$_3$ | OCO(CH$_2$)$_2$CH$_3$ | OCOCH$_3$ | 3-pyridyl |
| 165 | OCOCH$_3$ | OH | OH | OCOCH$_3$ | 3-pyridyl |
| 166 | OCOCH$_3$ | OCOCH$_2$CH$_3$ | OCOCH$_2$CH$_3$ | OCOCH$_2$CH$_3$ | 3-pyridyl |
| 167 | OCOCH$_2$CH$_3$ | OCOCH$_2$CH$_3$ | OCOCH$_2$CH$_3$ | OCOCH$_2$CH$_3$ | 3-pyridyl |
| 168 | OCOCH$_2$CH$_3$ | OCOCH$_3$ | OCOCH$_3$ | OCOCH$_3$ | 3-pyridyl |
| 169 | OCO(CH$_2$)$_3$CH$_3$ | OCOCH$_3$ | OCOCH$_3$ | OCOCH$_3$ | 3-pyridyl |
| 170 | OCO(CH$_2$)$_3$CH$_3$ | OCOCH$_3$ | OCOCH$_3$ | OCO(CH$_2$)$_3$CH$_3$ | 3-pyridyl |
| 171 | OCO(CH$_2$)$_2$CH$_3$ | OCOCH$_3$ | OCOCH$_3$ | OCOCH$_3$ | 3-pyridyl |
| 172 | OCH$_3$ | OCOCH$_3$ | OCOCH$_3$ | OCOCH$_3$ | 3-pyridyl |
| 173 | H(=) | OSO$_2$CH$_3$ | OSO$_2$CH$_3$ | OH | 3-pyridyl |
| 174 | H(=) | OCOC$_6$H$_5$ | OSO$_2$CH$_3$ | OCOCH$_3$ | 3-pyridyl |
| 175 | H(=) | OH | OH | OCOCH$_3$ | 3-pyridyl |
| 176 | H(=) | OCOCH$_3$ | OCOCH$_3$ | =O | 3-pyridyl |
| 177 | H(=) | | —O—CH(C$_6$H$_5$)—O— | OCOCH$_3$ | 3-pyridyl |
| 178 | H(=) | | —O—CH(CH(CH$_3$)$_2$)—O— | OH | 3-pyridyl |
| 179 | H(=) | | —O—CH(4-NO$_2$—C$_6$H$_4$)—O— | OH | 3-pyridyl |
| 180 | H(=) | OCOCH$_3$ | OCOCH$_3$ | OCOCH$_3$ | 3-pyridyl |

TABLE 10

| Compound No. | R$_1$ | R$_2$ | R$_3$ | R$_4$ | Het$_1$ |
|---|---|---|---|---|---|
| 181 | H(=) | OH | OH | OH | 3-pyridyl |
| 182 | H(=) | OCOCH$_3$ | OCOCH$_3$ | OH | 3-pyridyl |
| 183 | H(=) | OCOCH$_3$ | OCOCH$_3$ | OCH$_2$SCH$_3$ | 3-pyridyl |
| 184 | H(=) | OCOCH$_3$ | OCOCH$_3$ | OCH$_2$OCH$_3$ | 3-pyridyl |
| 185 | H(=) | OCOCH$_3$ | OCOCH$_3$ | OCO(CH$_2$)$_3$CH$_3$ | 3-pyridyl |
| 186 | H(=) | OCOCH$_3$ | OCOCH$_3$ | OCO(CH$_2$)$_2$Ph | 3-pyridyl |
| 187 | H(=) | OCOCH$_3$ | OSO$_2$CH$_3$ | OCOCH$_3$ | 3-pyridyl |
| 188 | H(=) | OCOCH$_2$CH$_3$ | OCOCH$_2$CH$_3$ | OCOCH$_2$CH$_3$ | 3-pyridyl |
| 189 | H(=) | OCOCH$_2$CH$_3$ | OCOCH$_2$CH$_3$ | OH | 3-pyridyl |
| 190 | H(=) | OH | OSO$_2$CH$_3$ | OH | 3-pyridyl |
| 191 | H(=) | OH | OH | OCO(CH$_2$)$_3$CH$_3$ | 3-pyridyl |
| 192 | H(=) | | —O—C(CH$_3$)$_2$—O— | OH | 3-pyridyl |
| 193 | H(=) | | —O—C(CH$_3$)$_2$—O— | OCO(CH$_2$)$_3$CH$_3$ | 3-pyridyl |
| 194 | H(=) | | —O—CH(C$_6$H$_5$)—O— | OH | 3-pyridyl |
| 195 | H(=) | | —O—CH(C$_6$H$_5$)—O— | OCO(CH$_2$)$_3$CH$_3$ | 3-pyridyl |
| 196 | H(=) | | —O—CH(4-OCH$_3$—C$_6$H$_4$)—O— | OH | 3-pyridyl |
| 197 | H(=) | | —O—CH(C$_2$H$_5$)—O— | OH | 3-pyridyl |
| 198 | H(=) | | —O—CH(C(CH$_3$)$_3$)—O— | OH | 3-pyridyl |
| 199 | H(=) | | —O—CH(CH$_2$C$_6$H$_5$)—O— | OH | 3-pyridyl |
| 200 | =O | OH | OH | OH | 3-pyridyl |

TABLE 11

| Compound No. | R₁ | R₂ | R₃ | R₄ | Het₁ |
|---|---|---|---|---|---|
| 201 | =O | OCOCH₃ | OCOCH₃ | =O | 3-pyridyl |
| 202 | =O | OCOCH₃ | OCOCH₃ | OH | 3-pyridyl |
| 203 | =O | OCOCH₃ | OCOCH₃ | OCOCH₃ | 3-pyridyl |
| 204 | =O | OCOCH₂CH₃ | OCOCH₂CH₃ | OCOCH₂CH₃ | 3-pyridyl |
| 205 | OH | OCOCH₂CH₃ | OCOCH₂CH₃ | OCO-(3-pyridyl) | 3-pyridyl |
| 206 | OH | OCOCH₂CH₃ | OCOCH₂CH₃ | OCOCH(CH₃)₂ | 3-pyridyl |
| 207 | OH | OCOCH₂CH₃ | OCOCH₂CH₃ | OCOC(CH₃)₃ | 3-pyridyl |
| 208 | OH | OCOCH₂CH₃ | OCOCH₂CH₃ | OCO-(4-CF₃—C₆H₄) | 3-pyridyl |
| 209 | OH | OCOCH₂CH₃ | OCOCH₂CH₃ | OCO-(1-imidazolyl) | 3-pyridyl |
| 210 | OH | OCOCH₂CH₃ | OCOCH₂CH₃ | OCONH(CH₂)₂CH₃ | 3-pyridyl |
| 211 | OH | OCOCH₂CH₃ | OCOCH₂CH₃ | O-(2-tetrahydropyranyl) | 3-pyridyl |
| 212 | OH | OCOCH₂CH₃ | OCOCH₂CH₃ | OCO-(6-Cl-3-pyridyl) | 3-pyridyl |
| 213 | OH | OCOCH₂CH₃ | OCOCH₂CH₃ | OCO-c-C₃H₅ | 3-pyridyl |
| 214 | OH | OCOCH₂CH₃ | OCOCH₂CH₃ | OCO-c-C₄H₇ | 3-pyridyl |
| 215 | OH | OCOCH₂CH₃ | OCOCH₂CH₃ | OCOCH=CH | 3-pyridyl |
| 216 | OH | OCOCH₂CH₃ | OCOCH₂CH₃ | OCO-(4-pyridyl) | 3-pyridyl |
| 217 | OH | OCOCH₂CH₃ | OCOCH₂CH₃ | OCO-(2-pyridyl) | 3-pyridyl |
| 218 | OH | OCO-c-C₃H₅ | OCO-c-C₃H₅ | OCO-c-C₃H₅ | 3-pyridyl |
| 219 | OH | OCO-c-C₄H₇ | OCO-c-C₄H₇ | OCO-c-C₄H₇ | 3-pyridyl |
| 220 | OH | OCOC₆H₅ | OCOC₆H₅ | OCOC₆H₅ | 3-pyridyl |

TABLE 12

| Compound No. | R₁ | R₂ | R₃ | R₄ | Het₁ |
|---|---|---|---|---|---|
| 221 | OH | OCOCH₂CH₃ | OCOCH₂CH₃ | OCO-(6-CF₃-3-pyridyl) | 3-pyridyl |
| 222 | OH | OCOCH₂CH₃ | OCOCH₂CH₃ | OCO-(4-CF₃-3-pyridyl) | 3-pyridyl |
| 223 | OH | OCOCH₂CF₃ | OCOCH₂CF₃ | OCOCH₂CF₃ | 3-pyridyl |
| 224 | OH | OCOCH₂CH₃ | OCOCH₂CH₃ | OCOCH₂CF₃ | 3-pyridyl |
| 225 | =O | OCOCH₂CH₃ | OCOCH₂CH₃ | OCOCH₂CH₃ | 6-Cl-3-pyridyl |
| 226 | OH | OCOCH₂CH₃ | OCOCH₂CH₃ | OCOCH₂CH₃ | 6-Cl-3-pyridyl |
| 227 | OH | OCOCH₂CH₃ | OCOCH₂CH₃ | OCO-(3-F-4-pyridyl) | 3-pyridyl |
| 228 | OH | OCOCH₂CH₃ | OCOCH₂CH₃ | OCO-(3-Cl-4-pyridyl) | 3-pyridyl |
| 229 | OH | OCOCH₂CH₃ | OCOCH₂CH₃ | OCO-(3-CH₃-2-pyridyl) | 3-pyridyl |
| 230 | OH | OCOCH₂CH₃ | OCOCH₂CH₃ | OCO-(3-COC₆H₅-2-pyridyl) | 3-pyridyl |
| 231 | OH | OCOCH₂CH₃ | OCOCH₂CH₃ | OCO-(3-OCH₂CH₂CH₃-2-pyridyl) | 3-pyridyl |
| 232 | OH | OCOCH₂CH₃ | OCOCH₂CH₃ | OCO-(6-F-3-pyridyl) | 3-pyridyl |
| 233 | OH | OCO-c-C₅H₉ | OCO-c-C₅H₉ | OCO-c-C₅H₉ | 3-pyridyl |
| 234 | OH | OCO-c-C₆H₁₁ | OCO-c-C₆H₁₁ | OCO-c-C₆H₁₁ | 3-pyridyl |
| 235 | OH | OCOCH₂CN | OCOCH₂CN | OCOCH₂CN | 3-pyridyl |
| 236 | OCOCH₂-c-C₃H₅ | OCOCH₂-c-C₃H₅ | OCOCH₂-c-C₃H₅ | OCOCH₂-c-C₃H₅ | 3-pyridyl |
| 237 | OH | OCOCH₂-c-C₃H₅ | OCOCH₂-c-C₃H₅ | OCOCH₂-c-C₃H₅ | 3-pyridyl |
| 238 | OH | OCO-(1-CH₃-2,2-diF-c-C₃H₂) | OCO-(1-CH₃-2,2-diF-c-C₃H₂) | OCO-(1-CH₃-2,2-diF-c-C₃H₂) | 3-pyridyl |
| 239 | OH | OCOCH₂CH₃ | OCOCH₂CH₃ | OCO-(4-CH₃-3-pyridyl) | 3-pyridyl |
| 240 | OH | OCOCH₂CH₃ | OCOCH₂CH₃ | OCO-(4-Cl-3-pyridyl) | 3-pyridyl |

TABLE 13

| Compound No. | R₁ | R₂ | R₃ | R₄ | Het₁ |
|---|---|---|---|---|---|
| 241 | OH | OCOCH₂CH₃ | OCOCH₂CH₃ | OCO-(4-COOCH₃-3-pyridyl) | 3-pyridyl |
| 242 | OH | OCOCH₂CH₃ | OCOCH₂CH₃ | OCO-[5-(CF₃)-thieno[3,2-b]pyridin-6-yl] | 3-pyridyl |
| 243 | OH | OCOCH₂CH₃ | OCOCH₂CH₃ | OCO-(2-CN—C₆H₄) | 3-pyridyl |
| 244 | OH | OCOCH₂CH₃ | OCOCH₂CH₃ | OCO-(2-CF₃—C₆H₄) | 3-pyridyl |
| 245 | OH | OCOCH₂CH₃ | OCOCH₂CH₃ | OCO-(2-F—C₆H₄) | 3-pyridyl |
| 246 | OH | OCOCH₂CH₃ | OCOCH₂CH₃ | OCO-(2-NO₂—C₆H₄) | 3-pyridyl |
| 247 | OH | OCOCH₂CH₃ | OCOCH₂CH₃ | OCO-(2-Cl-3-pyridyl) | 3-pyridyl |

TABLE 13-continued

| Compound No. | $R_1$ | $R_2$ | $R_3$ | $R_4$ | $Het_1$ |
|---|---|---|---|---|---|
| 248 | OH | OCOCH$_2$CH$_3$ | OCOCH$_2$CH$_3$ | OCO(2-Cl-6-CH$_3$-3-pyridyl) | 3-pyridyl |
| 249 | OH | OCOCH$_2$CH$_3$ | OCOCH$_2$CH$_3$ | OCH$_2$OCH$_3$ | 3-pyridyl |
| 250 | OH | OCO-(2,2-diF-c-C$_3$H$_3$) | OCO-(2,2-diF-c-C$_3$H$_3$) | OCO-(2,2-diF-c-C$_3$H$_3$) | 3-pyridyl |
| 251 | OH | OCOCH$_2$CH$_3$ | OCOCH$_2$CH$_3$ | OCO-(3-SC(CH$_3$)$_3$-2-pyridyl) | 3-pyridyl |
| 252 | OH | OCOCH$_2$CH$_3$ | OCOCH$_2$CH$_3$ | OCO-(3,5-diF-2-pyridyl) | 3-pyridyl |
| 253 | OH | OCOCH$_2$CH$_3$ | OCOCH$_2$CH$_3$ | OCO-2-pyrazinyl | 3-pyridyl |
| 254 | OH | OCOCH$_2$CH$_3$ | OCOCH$_2$CH$_3$ | OCO-4-thiazolyl | 3-pyridyl |
| 255 | OH | OCOCH$_2$CH$_3$ | OCOCH$_2$CH$_3$ | OCO-(3-Cl-2-thienyl) | 3-pyridyl |
| 256 | OH | OCOCH$_2$CH$_3$ | OCOCH$_2$CH$_3$ | OCO-(6-CH$_3$-3-pyridyl) | 3-pyridyl |
| 257 | OH | OCOCH$_2$CH$_3$ | OCOCH$_2$CH$_3$ | OCO-(6-Cl-2-pyridyl) | 3-pyridyl |
| 258 | OH | OCOCH$_2$CH$_3$ | OCOCH$_2$CH$_3$ | OCO-(6-F-2-pyridyl) | 3-pyridyl |
| 259 | OH | OCOCH$_2$CH$_3$ | OCOCH$_2$CH$_3$ | OCO-(1-CH$_3$-1H-indolyl) | 3-pyridyl |
| 260 | OH | OCOCH$_2$CH$_3$ | OCOCH$_2$CH$_3$ | OCO-(3-Cl-2-pyridyl) | 3-pyridyl |

TABLE 14

| Compound No. | $R_1$ | $R_2$ | $R_3$ | $R_4$ | $Het_1$ |
|---|---|---|---|---|---|
| 261 | OH | OCO-c-C$_3$H$_5$ | OCO-c-C$_3$H$_5$ | OH | 3-pyridyl |
| 262 | OH | OCOCH$_2$CH$_3$ | OCOCH$_2$CH$_3$ | OCO-(2-F-3-pyridyl) | 3-pyridyl |
| 263 | OH | OCOCH$_2$CH$_3$ | OCOCH$_2$CH$_3$ | OCO-(4-CN—C$_6$H$_4$) | 3-pyridyl |
| 264 | OH | OCOCH2CH$_3$ | OCOCH$_2$CH$_3$ | OCO-(3-CN—C$_6$H$_4$) | 3-pyridyl |
| 265 | OH | OCOCH$_2$CH$_3$ | OCOCH$_2$CH$_3$ | OCO-(3-CF$_3$—C$_6$H$_4$) | 3-pyridyl |
| 266 | OH | OCOCH$_2$CH$_3$ | OCOCH$_2$CH$_3$ | OCOCH$_2$(2-pyridyl) | 3-pyridyl |
| 267 | OH | OCOCH$_2$CH$_3$ | OCOCH$_2$CH$_3$ | OCOCH$_2$(3-pyridyl) | 3-pyridyl |
| 268 | OH | OCOCH$_2$CH$_3$ | OCOCH$_2$CH$_3$ | OCOCH$_2$S(4-pyridyl) | 3-pyridyl |
| 269 | OH | OCO-c-C$_3$H$_5$ | OCO-c-C$_3$H$_5$ | OCO-(2-CN—C$_6$H$_4$) | 3-pyridyl |
| 270 | OH | OCO-c-C$_3$H$_5$ | OCO-c-C$_3$H$_5$ | OCO(4-CF$_3$-3-pyridyl) | 3-pyridyl |
| 271 | OH | OCO-c-C$_3$H$_5$ | OCO-c-C$_3$H$_5$ | OCO(3-Cl-2-pyridyl) | 3-pyridyl |
| 272 | OH | —O—CH(C$_6$H$_5$)—O— | | =O | 3-pyridyl |
| 273 | OH | —O—CH(4-OCH$_3$—C$_6$H$_4$)—O— | | =O | 3-pyridyl |
| 274 | OCO(CH$_2$)$_3$CH$_3$ | —O—CO—O— | | OCO(CH$_2$)$_3$CH3 | 3-pyridyl |
| 275 | OCOCH$_3$ | —O—CH(C$_6$H$_5$)—O— | | OCOCH$_3$ | 3-pyridyl |
| 276 | =O | —O—CH(4-OCH$_3$—C$_6$H$_4$)—O— | | OH | 3-pyridyl |

Production Process

The composition according to the present invention can be prepared by mixing the compound represented by formula (I), (Ia), or (Ib) as active ingredient with an agriculturally and horticulturally acceptable carrier. The compound represented by formula (I), (Ia), or (Ib) according to the present invention can be produced according to the following procedure.

Among the compounds according to the present invention, the compounds represented by formula (II) can be synthesized by the method described in Japanese Patent Laid-Open Publication No. 259569/1996, Japanese Patent Laid-Open Publication No. 269062/1996, Japanese Patent Laid-Open Publication No. 269065/1996, or *Journal of Antibiotics* (1997), 50(3), pp. 229-36. When pyripyropene A is used as a starting material, pyripyropene A, produced by the method described in Journal of Society of Synthetic Organic Chemistry, Japan (1998), Vol. 56, No. 6, pp. 478-488 or WO 94/09417, may be used as the starting material.

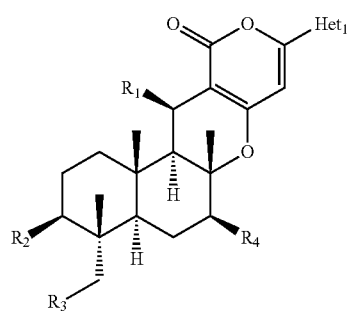

(II)

wherein $R_1$ represents hydroxyl, optionally substituted $C_{1-6}$ alkylcarbonyloxy, optionally substituted $C_{2-6}$ alkenylcarbonyloxy, optionally substituted $C_{2-6}$ alkynyl carbonyloxy, optionally substituted $C_{1-6}$ alkyloxy, optionally substituted $C_{2-6}$ alkenyloxy, optionally substituted $C_{2-6}$ alkynyloxy, optionally substituted benzyloxy, or oxo in the absence of a hydrogen atom at the 13-position, and $R_2$, $R_3$ and $R_4$ are as defined in formula (I).

Further, among the compounds according to the present invention, the compounds represented by formula (III) can be synthesized by the method described in Japanese Patent Laid-Open Publication No. 269063/1996, or Japanese Patent Laid-Open Publication No. 269066/1996.

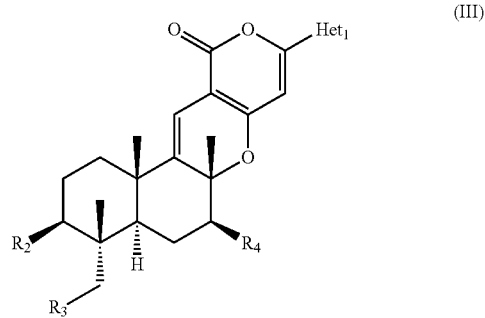

(III)

wherein $R_2$, $R_3$ and $R_4$ are as defined in formula (I).

Use

Insect species against which pyripyropene derivatives of formula (I) or (Ib) according to the present invention have control effect include: lepidopteran pests, for example, *Spodoptera litura, Mamestra brassicae, Pseudaletia separata*, green caterpillar, *Plutella xylostella, Spodoptera exigua, Chilo suppressalis, Cnaphalocrocis medinalis*, Tortricidae, Carposinidae, Lyonetiidae, Lymantriidae, pests belonging to the genus *Agrotis* spp., pests belonging to the genus *Helicoverpa* spp., and pests belonging to the genus *Heliothis* spp.; hemipteran pests, for example, Aphidoidea including Aphididae, Adelgidae and Phylloxeridae such as *Myzus persicae, Aphis gossypii, Aphis fabae, Aphis maidis* (corn-leaf aphid), *Acyrthosiphon pisum, Aulacorthum solani, Aphis craccivora, Macrosiphum euphorbiae, Macrosiphum avenae, Metopolophium dirhodum, Rhopalosiphum padi, Schizaphis graminum, Brevicoryne brassicae, Lipaphis erysimi, Aphis citricola*, Rosy apple aphid, *Eriosoma lanigerum, Toxoptera aurantii*, and *Toxoptera citricidus*; Deltocephalidae such as *Nephotettix cincticeps*, Delphacidae such as *Laodelphax striatellus, Nilaparvata lugens*, and *Sogatella furcifera*; Pentatomidae such as *Eysarcoris ventralis, Nezara viridula*, and *Trigonotylus coelestialium*; Aleyrodidae such as *Bemisia argentifolii, Bemisia tabaci*, and *Trialeurodes vaporariorum*; Diaspididae, Margarodidae, Ortheziidae, Aclerdiae, Dactylopiidae, Kerridae, Pseudococcidae, Coccidae, Eriococcidae, Asterolecaniidae, Beesonidae, Lecanodiaspididae, or Cerococcidae, such as *Pseudococcus comstocki* and *Planococcus citri Rissoz*; Coleoptera pests, for example, *Lissorhoptrus oryzophilus, Callosobruchuys chienensis, Tenebrio molitor, Diabrotica virgifera virgifera, Diabrotica undecimpunctata howardi, Anomala cuprea, Anomala rufocuprea, Phyllotreta striolata, Aulacophora femoralis, Leptinotarsa decemlineata, Oulema oryzae*, Carposinidae, and Cerambycidae; Acari, for example, *Tetranychus urticae, Tetranychus kanzawai*, and *Panonychus citri*; Hymenopteran pests, for example, Tenthredinidae; Orthopteran pests, for example, Acrididae; Dipteran pests, for example, Muscidae and Agromyzidae; Thysanopteran pests, for example, *Thrips palmi* and *Frankliniella occidentalis*; Plant Parasitic Nematodes, for example, *Meloidogyne hapla, Pratylenchus* spp., *Aphelenchoides besseyi* and *Bursaphelenchus xylophilus*;

and parasites of animals, for example, Siphonaptera, Anoplura, mites such as *Boophilus microplus, Haemaphysalis longicornis, Rhipicephalus sanguineus*, and *Scarcoptes scabiei*. Preferred are hemipteran pests.

The compound represented by formula (Ia) accordingly to the present invention has significant control effect against hemipteran pests. Preferred hemipteran pests are selected from Aphidoidea such as Aphididae, Adelgidae, and Phylloxeridae, particularly preferably Aphididae; Coccoidea such as Diaspididae, Margarodidae, Ortheziidae, Aclerdiae, Dactylopiidae, Kerridae, Pseudococcidae, Coccidae, Eriococcidae, Asterolecaniidae, Beesonidae, Lecanodiaspididae, and Cerococcidae; and Aleyrodidae. More preferred are *Myzus persicae, Aphis gossypii, Aphis fabae, Aphis maidis* (corn-leaf aphid), *Acyrthosiphon pisum, Aulacorthum solani, Aphis craccivora, Macrosiphum euphorbiae, Macrosiphum avenae, Metopolophium dirhodum, Rhopalosiphum padi, Schizaphis graminum, Brevicoryne brassicae, Lipaphis erysimi, Aphis citricola*, Rosy apple aphid, *Eriosoma lanigerum, Toxoptera aurantii, Toxoptera citricidus*, and *Pseudococcus comstocki*.

The composition according to the present invention can be prescribed in any suitable formulation, such as emulsifiable concentrates, liquid formulations, suspension, wettable powder, flowables, dust, granules, tablets, oil solutions, aerosols, or smoking agents by using suitable agriculturally and horticulturally acceptable carriers. Accordingly, the carrier include solid carriers, liquid carriers, gaseous carriers, surfactants, dispersants and/or other adjuvants for formulations, and the like.

Solid carriers usable herein include, for example, talc, bentonite, clay, kaolin, diatomaceous earth, vermiculite, white carbon, and calcium carbonate.

Examples of liquid carriers include: alcohols, such as methanol, n-hexanol, and ethylene glycol; ketones, such as acetone, methyl ethyl ketone, and cyclohexanone; aliphatic hydrocarbons, such as n-hexane, kerosine, and kerosene; aromatic hydrocarbons, such as toluene, xylene, and methylnaphthalene; ethers, such as diethyl ether, dioxane, and tetrahydrofuran; esters, such as ethyl acetate; nitriles, such as acetonitrile and isobutyronitrile; acid amides, such as dimethylformamide and dimethylacetamide; vegetable oils, such as soy bean oil and cotton seed oil; dimethylsulfoxide; and water.

Gaseous carriers include, for example, LPG, air, nitrogen, carbon dioxide, and dimethyl ether.

Surfactants or dispersants usable, for example, for emulsifying, dispersing, or spreading include, for example, alkylsulfonic esters, alkyl(aryl)sulfonic acid salts, polyoxyalkylene alkyl(aryl) ethers, polyhydric alcohol esters, and lignin sulfonic acid salts.

Adjuvants usable for improving the properties of formulations include, for example, carboxymethylcellulose, gum arabic, polyethylene glycol, and calcium stearate.

The above carriers, surfactants, dispersants, and adjuvant may be used either solely or in combination according to need.

The content of the active ingredient in the formulation is not particularly limited. In general, however, the content of the active ingredient is 1 to 75% by weight for emulsifiable concentrates, 0.3 to 25% by weight for dust, 1 to 90% by weight for wettable powder, and 0.5 to 10% by weight for granules.

The compound represented by formula (I), (Ia), (Ib), or an agriculturally and horticulturally acceptable salt thereof and the above formulations comprising the same may be applied as such or after dilution to plants or soil. Therefore, according to another aspect of the present invention, there is provided a method for controlling a pest, comprising applying an effective amount of a compound represented by formula (I) or an agriculturally and horticulturally acceptable salt thereof to a plant or soil. According to still another aspect of the present invention, there is provided a method for controlling a hemipteran pest, comprising applying an effective amount of a compound represented by formula (Ia) or an agriculturally and horticulturally acceptable salt thereof to a plant or soil. According to a further aspect of the present invention, there is provided a method for controlling a pest, comprising applying an effective amount of a compound represented by formula (Ib) or an agriculturally and horticulturally acceptable salt thereof to a plant or soil. Preferred methods usable for applying the compound or formulation to plants or soil include spreading treatment, soil treatment, surface treatment, and fumigation treatment.

Spreading treatments include, for example, spreading, spraying, misting, atomizing, granule application, and submerged application. Soil treatments include, for example, soil affusion and soil mixing. Examples of surface treatments include, for example, coating, dust coating, and covering. Fumigation treatments include, for example, covering of soil with a polyethylene film after soil injection. Accordingly, the control method according to the present invention comprises a method in which the compound represented by formula (I), (Ia), or (Ib) or a formulation comprising the same is applied by fumigation in a sealed space.

The composition according to the present invention may be used as a mixture or in a combination with, for example, other insecticides, fungicides, miticides, herbicides, plant growth-regulating agents, or fertilizers. Agents which may be mixed or used in combination include those described, for example, in The Pesticide Manual, 13th edition, published by The British Crop Protection Council; and SHIBUYA INDEX, the 10th edition, 2005, published by SHIBUYA INDEX RESEARCH GROUP. More specifically, insecticides usable herein include, for example, organophosphate ester compounds such as acephate, dichlorvos, EPN, fenitrothion, fenamifos, prothiofos, profenofos, pyraclofos, chlorpyrifos-methyl, and diazinon; carbamate compounds such as methomyl, thiodicarb, aldicarb, oxamyl, propoxur, carbaryl, fenobucarb, ethiofencarb, fenothiocarb, pirimicarb, carbofuran, and benfuracarb; nereistoxin derivatives such as cartap and thiocyclam; organochlorine compounds such as dicofol and tetradifon; pyrethroid compounds such as permethrin, tefluthrin, cypermethrin, deltamethrin, cyhalothrin, fenvalerate, fluvalinate, ethofenprox, and silafluofen; benzoylurea compounds such as diflubenzuron, teflubenzuron, flufenoxuron, and chlorfluazuron; juvenile hormone-like compounds such as methoprene; and molting hormone-like compounds such as chromafenozide. Other compounds usable herein include buprofezin, hexythiazox, amitraz, chlordimeform, pyridaben, fenpyroximate, pyrimidifen, tebufenpyrad, fluacrypyrim, acequinocyl, cyflumetofen, flubendiamide, ethiprole, fipronil, ethoxazole, imidacloprid, chlothianidin, pymetrozine, bifenazate, spirodiclofen, spiromesifen, flonicamid, chlorfenapyr, pyriproxyfene, indoxacarb, pyridalyl, or spinosad, avermectin, milbemycin, organometallic compounds, dinitro compounds, organosulfur compounds, urea compounds, triazine compounds, hydrazine compounds.

The composition according to the present invention may also be used as a mixture or in a combination with microbial pesticides such as BT formulations and entomopathogenic viral agents.

Fungicides usable herein include, for example, strobilurin compounds such as azoxystrobin, kresoxym-methyl, and trifloxystrobin; anilinopyrimidine compounds such as mepanipyrim, pyrimethanil, and cyprodinil; azole compounds such as triadimefon, bitertanol, triflumizole, etaconazole, propiconazole, penconazole, flusilazole, myclobutanil, cyproconazole, tebuconazole, hexaconazole, prochloraz, and simeconazole; quinoxaline compounds such as quinomethionate; dithiocarbamate compounds such as maneb, zineb, mancozeb, polycarbamate, and propineb; phenylcarbamate compounds such as diethofencarb; organochlorine compounds such as chlorothalonil and quintozene; benzimidazole compounds such as benomyl, thiophanate-methyl, and carbendazole; phenylamide compounds such as metalaxyl, oxadixyl, ofurace, benalaxyl, furalaxyl, and cyprofuram; sulfenic acid compounds such as dichlofluanid; copper compounds such as copper hydroxide and oxine-copper; isoxazole compounds such as hydroxyisoxazole; organophosphorus compounds such as fosetyl-aluminium and tolclofos-methyl; N-halogenothioalkyl compounds such as captan, captafol, and folpet; dicarboxyimide compounds such as procymidone, iprodione, and vinchlozolin; benzanilide compounds such as flutolanil and mepronil; morpholine compounds such as fenpropimorph and dimethomorph; organotin compounds such as fenthin hydroxide, and fenthin acetate; and cyanopyrrole compounds such as fludioxonil and fenpiclonil. Other compounds usable herein include fthalide, fluazinam, cymoxanil, triforine, pyrifenox, fenarimol, fenpropidin, pencycuron, cyazofamid, iprovalicarb, and benthiavalicarb-isopropyl and the like.

According to another aspect of the present invention, there is provided use of a compound represented by formula (I) or an agriculturally and horticulturally acceptable salt thereof as a pest control agent. According to still another aspect of the present invention, there is provided use of a compound represented by formula (Ia) or an agriculturally and horticulturally acceptable salt thereof as a hemipteran pest control agent. According to still another aspect of the present invention, there is provided use of a compound represented by formula (Ib) or an agriculturally and horticulturally acceptable salt thereof as a pest control agent.

EXAMPLES

The present invention is further illustrated by the following Examples that are not intended as a limitation of the invention. The compound Nos. correspond to the compound Nos. in Tables 1 to 14.

Example 1

Synthesis of Compound 73

Compound 76 (890 mg) synthesized by the method described in Japanese Patent Laid-Open Publication No. 259569/1996 was dissolved in an 80% aqueous methanol solution. Next, 1,8-diazabicyclo[5.4.0]-undeca-7-ene (216 mg) was added to the solution, and the mixture was stirred at room temperature for 1.5 hr. The reaction mixture was added with acetic acid to quench the reaction, and the solvent was removed by evaporation under the reduced pressure. Water was added to the precipitated crystal, followed by extraction with chloroform. The chloroform layer was washed with saturated brine, was dried over anhydrous magnesium sulfate, and the solvent was removed by evaporation under the reduced pressure to give a crude product of compound 73. The crude product was purified by chromatography on silica gel (Mega Bond Elut (Varian), acetone:hexane=1:1) to give compound 73 (451 mg).

Mass spectrometric data (FAB$^+$): 570(M+H)$^+$

Example 2

Synthesis of Compound 218

Compound 102 (30 mg) synthesized by the method described in Japanese Patent Laid-Open Publication No. 259569/1996 and cyclopropanecarboxylic acid (112 mg) were dissolved in anhydrous N,N-dimethylformamide (2 ml), and 1-ethyl-3-(3-dimethylaminopropyl)-carbodiimide hydrochloride (76 mg) and 4-(dimethylamino)pyridine (32 mg) were added to the solution. The reaction solution was stirred at room temperature for 68 hr and was then poured into water, followed by extraction with ethyl acetate. The ethyl acetate layer was washed with saturated brine and was dried over anhydrous magnesium sulfate, and the solvent was removed by evaporation under the reduced pressure to give a crude product of compound 218. The crude product was purified by preparative thin-layer chromatography (Merck Silica Gel 60 $F_{254}$ 0.5 mm, acetone:hexane=1:1) to give compound 218 (33 mg).

Mass spectrometric data ($FAB^+$): 662$(M+H)^+$

Example 3

Synthesis of Compound 261

Compound 218 (1.07 g) prepared in Example 2 was dissolved in an 80% aqueous methanol solution. 1,8-Diazabicyclo[5.4.0]-undeca-7-ene (271 mg) was added to the solution, and the mixture was stirred at room temperature for 24.5 hr. The reaction mixture was added with acetic acid to quench the reaction, and the solvent was removed by evaporation under the reduced pressure. Water was added to the precipitated crystal, followed by extraction with chloroform. The chloroform layer was washed with saturated brine and was dried over anhydrous magnesium sulfate, and the solvent was removed by evaporation under the reduced pressure to give a crude product of compound 261. The crude product was purified by chromatography on silica gel (Mega Bond Elut (Varian), acetone:hexane=1:1) to give compound 261 (233 mg).

Mass spectrometric data ($ESI^+$): 594$(M+H)^+$

Example 4

Synthesis of Compound 222

Compound 73 (30 mg) prepared in Example 1 and 4-(trifluoromethyl)nicotinic acid (30 mg) was dissolved in anhydrous N,N-dimethylformamide (3 ml). Next, 1-ethyl-3-(3-dimethylaminopropyl)-carbodiimide hydrochloride (15 mg) and 4-(dimethylamino)pyridine (4 mg) were added to the solution, and the reaction solution was stirred at room temperature for 15 hr and was then poured into water, followed by extraction with ethyl acetate. The ethyl acetate layer was washed with saturated brine and was dried over anhydrous magnesium sulfate, and the solvent was removed by evaporation under the reduced pressure to give a crude produce of compound 222. The crude product was purified by preparative thin-layer chromatography (Merck Silica Gel 60 $F_{254}$ 0.5 mm, acetone:hexane=1:1) to give compound 222 (19 mg).

Mass spectrometric data ($FAB^+$): 743$(M+H)^+$

Example 5

Synthesis of Compound 269

Compound 261 (20 mg) prepared in Example 3 and 2-cyanobenzoic acid (30 mg) were dissolved in anhydrous N,N-dimethylformamide (1 ml), and 1-ethyl-3-(3-dimethylaminopropyl)-carbodiimide hydrochloride (26 mg) and 4-(dimethylamino)pyridine (4 mg) were added to the solution. The reaction solution was stirred at room temperature for 12 hr, and the reaction solution was added to water, followed by extraction with ethyl acetate. The ethyl acetate layer was washed with saturated brine and was dried over anhydrous magnesium sulfate. The solvent was removed by evaporation under the reduced pressure to give a crude product of compound 269. The crude product was purified by preparative thin-layer chromatography (Merck Silica Gel 60 $F_{254}$ 0.5 mm, acetone:hexane=1:1) to give compound 269 (18 mg).

Mass spectrometric data ($ESI^+$): 723 $(M+H)^+$

Example 6

Synthesis of Compound 225

1,7,11-Trideacetyl-13-oxo-6"-chloropyripyropene A (10 mg) described in Journal of Antibiotics (1997), 50 (3), 229-36 was dissolved in anhydrous N,N-dimethylformamide (1 ml). Triethylamine (24 mg) and 4-(dimethylamino)pyridine (0.5 mg) were added to the solution, and the mixture was stirred at room temperature for 30 min. Thereafter, propionic acid anhydride (8 mg) was added. The reaction solution was stirred at the same temperature for 4 hr. The reaction solution was added to water, and the mixture was extracted with ethyl acetate. The ethyl acetate layer was washed with saturated brine and was dried over anhydrous magnesium sulfate, and the solvent was then removed by evaporation under the reduced pressure to give a crude product of compound 225. The crude product was purified by preparative thin-layer chromatography (Merck Silica Gel 60 $F_{254}$ 0.5 mm, acetone: hexane=1:1) to give compound 225 (5.6 mg).

Mass spectrometric data ($ESI^+$): 658 $(M+H)^+$

Example 7

Synthesis of Compound 226

Compound 225 (10 mg) prepared in Example 6 was dissolved in methanol (1 ml). Cerium(III) chloride heptahydrate (57 mg) and sodium borohydride (6 mg) were added to the solution. The mixture was stirred at 0° C. for 7 hr, and water was added to the reaction solution, followed by extraction with ethyl acetate. The ethyl acetate layer was washed with saturated brine and was dried over anhydrous magnesium sulfate, and the solvent was removed by evaporation under the reduced pressure to give a crude product of compound 226. The crude product was purified by preparative thin-layer chromatography (Merck Silica Gel 60 $F_{254}$ 0.5 mm, acetone: hexane=1:1) to give compound 226 (8.5 mg).

Mass spectrometric data ($ESI^+$): 660 $(M+H)^+$

Example 8

Synthesis of Compound 273

1,7,11-Trideacetyl-1,11-o-p-methoxybenzylidene pyripyropene A (10 mg) described in Japanese Patent Laid-Open Publication No. 269065/1996 was dissolved in anhydrous dichloromethane (0.5 ml), and pyridinium dichromate (PDC) (39 mg) was added to the solution. The reaction solution was stirred at room temperature for 4 hr, and the reaction solution was added to water. The dichloromethane layer was washed with saturated brine, and was dried over anhydrous sodium sulfate, and the solvent was then removed by evaporation under the reduced pressure to give a crude product of compound 273. The crude product was purified by preparative thin-layer chromatography (Merck Silica Gel 60 $F_{254}$ 0.5 mm, chloroform:methanol=12.5:1) to give compound 273 (4.4 mg).

Mass spectrometric data (ESI[+]): 574 (M+H)[+]

Example 9

Synthesis of Compound 274

1,11-o-Cyclic carbonate1,7,11-trideacetyl-pyripyropene A (4 mg) described in Japanese Patent Laid-Open Publication No. 269065/1996 was dissolved in anhydrous dichloromethane (1 ml). Triethylamine (5 μl) and 4-(dimethylamino)pyridine (1 mg) were added to the solution. The reaction solution was stirred at room temperature for 30 min, and valeric acid anhydride (5 μl) was added thereto. Next, the reaction solution was stirred at room temperature for 3 hr. The reaction solution was added to water, and the dichloromethane layer was washed with saturated brine and was dried over anhydrous sodium sulfate. The solvent was then removed by evaporation under the reduced pressure to give a crude product of compound 274. The crude product was purified by preparative thin-layer chromatography (Merck Silica Gel 60 $F_{254}$ 0.5 mm, chloroform:methanol=25:1) to give compound 274 (0.1 mg).

Mass spectrometric data (ESI[+]): 652 (M+H)[+]

Example 10

Compounds shown in Tables 15 to 17 were synthesized using starting materials, reaction reagents 1 and 2 and solvents described in these tables. Further, the $^1$H-NMR data about some of the compounds in Tables 15 to 17 was described in Tables 18 to 29. In addition, CDCl₃ was used as the solvent for the $^1$H-NMR measurement. Tetramethylsilane was used as a standard substance for the $^1$H-NMR measurement.

TABLE 15

| Compound No. | Starting material (Compound No.) | Amount | Reaction reagent 1 | Amount | Reaction reagent 2 | Solvent | Yield | Mass spectrometric data Measuring Method | Data |
|---|---|---|---|---|---|---|---|---|---|
| 74 | 73 | 30 mg | acetic anhydride | 32.7 mg | Et₃N 64.0 mg, DMAP 12.8 mg | DMF | 13.6 mg | FAB | 612 (M + H)[+] |
| 77 | 73 | 30 mg | benzoic acid | 84.8 mg | EDCI 49.2 mg, DMAP 46.4 mg | DMF | 36.4 mg | FAB | 674 (M + H)[+] |
| 91 | 102 | 30 mg | pivalic anhydride | 220 mg | Et₃N 60.0 mg, DMAP 8.0 mg | DMF | 27.7 mg | FAB | 710 (M + H)[+] |
| 205 | 73 | 30 mg | nicotinic acid | 12.9 mg | EDCI 15.1 mg, DMAP 6.4 mg | DMF | 27.1 mg | FAB | 675 (M + H)[+] |
| 206 | 73 | 30 mg | isobutyric anhydride | 50.0 mg | Et₃N 64.0 mg, DMAP 12.8 mg | DMF | 11.4 mg | FAB | 640 (M + H)[+] |
| 207 | 73 | 30 mg | pivalic anhydride | 58.9 mg | Et₃N 64.0 mg, DMAP 12.8 mg | DMF | 23.4 mg | FAB | 654 (M + H)[+] |
| 208 | 73 | 30 mg | 4-(trifluoromethyl)benzoic anhydride | 114 mg | Et₃N 64.0 mg, DMAP 12.8 mg | DMF | 32.2 mg | FAB | 742 (M + H)[+] |
| 209 | 73 | 40 mg | 1,1-carbonyl diimidazole | 34.0 mg | — | toluene | 5.1 mg | FAB | 664 (M + H)[+] |
| 210 | 73 | 30 mg | propyl isocyanate | 26.9 mg | Et₃N 64.0 mg, DMAP 12.8 mg | DMF | 3.2 mg | FAB | 655 (M + H)[+] |
| 211 | 73 | 30 mg | 3,4-dihydro-2H-pyran | 155 mg | pyridine hydrochloride | CH₂Cl₂ | 22.7 mg | FAB | 654 (M + H)[+] |
| 212 | 73 | 30 mg | 6-chloro nicotinic acid | 16.5 mg | EDCI 15.2 mg, DMAP 6.4 mg | DMF | 39.8 mg | FAB | 709 (M + H)[+] |
| 213 | 73 | 30 mg | cyclopropane carboxylic acid | 27 mg | EDCI 15.2 mg, DMAP 6.4 mg | DMF | 18.2 mg | FAB | 638 (M + H)[+] |
| 214 | 73 | 30 mg | cyclobutane carboxylic acid | 31 mg | EDCI 15.2 mg, DMAP 6.4 mg | DMF | 14.9 mg | FAB | 652 (M + H)[+] |
| 215 | 73 | 30 mg | acrylic acid | 22.5 mg | EDCI 15.2 mg, DMAP 6.4 mg | DMF | 5.6 mg | FAB | 624 (M + H)[+] |
| 216 | 73 | 30 mg | isonicotinic acid | 12.9 mg | EDCI 15.2 mg, DMAP 6.4 mg | DMF | 8.2 mg | FAB | 675 (M + H)[+] |
| 217 | 73 | 30 mg | picolinic acid | 12.9 mg | EDCI 15.2 mg, DMAP 6.4 mg | DMF | 40.6 mg | FAB | 675 (M + H)[+] |
| 219 | 102 | 30 mg | cyclobutane carboxylic acid | 131 mg | EDCI 76 mg, DMAP 32 mg | DMF | 38.9 mg | FAB | 704 (M + H)[+] |
| 220 | 102 | 30 mg | benzoic acid | 160 mg | EDCI 126 mg, DMAP 80 mg | DMF | 37.9 mg | FAB | 770 (M + H)[+] |
| 221 | 73 | 30 mg | 6-(trifluoromethyl)nicotinic acid | 30 mg | EDCI 15.2 mg, DMAP 6.4 mg | DMF | 35.4 mg | FAB | 743 (M + H)[+] |
| 223 | 102 | 30 mg | 3,3,3-trifluoropropionic acid | 168 mg | EDCI 126 mg, DMAP 80 mg | DMF | 10.4 mg | FAB | 788 (M + H)[+] |
| 224 | 73 | 30 mg | 3,3,3-trifluoropropionic acid | 20 mg | EDCI 15.2 mg, DMAP 6.4 mg | DMF | 8.0 mg | FAB | 680 (M + H)[+] |

TABLE 16

| Compound No. | Starting material (Compound No.) | Amount | Reaction reagent 1 |
|---|---|---|---|
| 227 | 73 | 20 mg | 3-fluoro-isonicotinic acid |
| 228 | 73 | 20 mg | 3-chloro-isonicotinic acid |
| 229 | 73 | 20 mg | 3-methylpicolinic acid |
| 230 | 73 | 20 mg | 3-benzoyl-2-pyridine carboxylic acid |
| 231 | 73 | 20 mg | 3-n-propoxy picolinic acid |
| 232 | 73 | 20 mg | 6-fluoro nicotinic acid |
| 233 | 102 | 20 mg | cyclopentane carboxylic acid |
| 234 | 102 | 20 mg | cyclohexane carboxylic acid |
| 235 | 102 | 20 mg | cyano acetic acid |
| 236 | 102 | 20 mg | cyclopropyl acetic acid |
| 237 | 102 | 20 mg | cyclopropylacetic acid |
| 238 | 102 | 20 mg | 2,2-difluoro-1-methylcyclopropanecarboxylic acid |
| 239 | 73 | 20 mg | 4-methylnicotinic acid |
| 240 | 73 | 20 mg | 4-chloro nicotinic acid |
| 241 | 73 | 20 mg | (4-methoxy carbonyl) nicotinic acid |
| 242 | 73 | 20 mg | 5-(trifluoromethyl)thieno[3,2-b]pyridine-6-carboxylic acid |
| 243 | 73 | 20 mg | 2-cyano benzoic acid |
| 244 | 73 | 20 mg | 2-(trifluoromethyl)benzoic acid |
| 245 | 73 | 20 mg | 2-fluoro benzoic acid |
| 246 | 73 | 20 mg | 2-nitro benzoic acid |
| 247 | 73 | 20 mg | 2-chloro nicotinic acid |

| Compound No. | Amount | Reaction reagent 2 | Solvent | Yield | Mass spectrometric data Measuring Method | Data |
|---|---|---|---|---|---|---|
| 227 | 15 mg | EDCI 14 mg, DMAP 4 mg | DMF | 5.4 mg | FAB | 693 (M + H)$^+$ |
| 228 | 17 mg | EDCI 14 mg, DMAP 4 mg | DMF | 7.8 mg | FAB | 709 (M + H)$^+$ |
| 229 | 14 mg | EDCI 28 mg, DMAP 8 mg | DMF | 16.7 mg | FAB | 689 (M + H)$^+$ |
| 230 | 48 mg | EDCI 28 mg, DMAP 8 mg | DMF | 16.4 mg | FAB | 779 (M + H)$^+$ |
| 231 | 38 mg | EDCI 28 mg, DMAP 8 mg | DMF | 17.3 mg | FAB | 733 (M + H)$^+$ |
| 232 | 30 mg | EDCI 28 mg, DMAP 8 mg | DMF | 5.3 mg | FAB | 693 (M + H)$^+$ |
| 233 | 99 mg | EDCI 84 mg, DMAP 5 mg | DMF | 28.3 mg | FAB | 746 (M + H)$^+$ |
| 234 | 112 mg | EDCI 84 mg, DMAP 5 mg | DMF | 21.5 mg | FAB | 788 (M + H)$^+$ |
| 235 | 74 mg | EDCI 84 mg, DMAP 5 mg | DMF | 3.3 mg | FAB | 659 (M + H)$^+$ |
| 236 | 87 mg | EDCI 84 mg, DMAP 5 mg | DMF | 16.7 mg | FAB | 786 (M + H)$^+$ |
| 237 | 87 mg | EDCI 84 mg, DMAP 5 mg | DMF | 8.2 mg | FAB | 704 (M + H)$^+$ |
| 238 | 118 mg | EDCI 84 mg, DMAP 5 mg | DMF | 6.1 mg | FAB | 812 (M + H)$^+$ |
| 239 | 36 mg | EDCI 28 mg, DMAP 8 mg | DMF | 16.1 mg | FAB | 689 (M + H)$^+$ |
| 240 | 33 mg | EDCI 28 mg, DMAP 8 mg | DMF | 13.8 mg | FAB | 709 (M + H)$^+$ |
| 241 | 38 mg | EDCI 28 mg, DMAP 8 mg | DMF | 18.8 mg | FAB | 733 (M + H)$^+$ |
| 242 | 38 mg | EDCI 28 mg, DMAP 8 mg | DMF | 20.3 mg | FAB | 799 (M + H)$^+$ |
| 243 | 31 mg | EDCI 28 mg, DMAP 8 mg | DMF | 6.6 mg | FAB | 699 (M + H)$^+$ |
| 244 | 40 mg | EDCI 28 mg, DMAP 8 mg | DMF | 10.2 mg | FAB | 742 (M + H)$^+$ |
| 245 | 29 mg | EDCI 28 mg, DMAP 8 mg | DMF | 16.1 mg | FAB | 692 (M + H)$^+$ |
| 246 | 35 mg | EDCI 28 mg, DMAP 8 mg | DMF | 9.8 mg | FAB | 719 (M + H)$^+$ |
| 247 | 33 mg | EDCI 28 mg, DMAP 8 mg | DMF | 13.1 mg | FAB | 709 (M + H)$^+$ |

TABLE 17

| Compound No. | Starting material (Compound No.) | Amount | Reaction reagent 1 | Amount |
|---|---|---|---|---|
| 248 | 73 | 20 mg | 2-chloro-6-methylnicotinic acid | 36 mg |
| 249 | 73 | 20 mg | methoxymethylbromide | 31 mg |
| 250 | 102 | 20 mg | 2,2-difluorocyclopropane carboxylic acid | 106 mg |
| 251 | 73 | 20 mg | 3-tert-buthylthio-2-carboxy piridine | 44 mg |
| 252 | 73 | 20 mg | 3,5-difluoropyridine-2-carboxylic acid | 33 mg |
| 253 | 73 | 20 mg | pyrazine carboxylic acid | 26 mg |
| 254 | 73 | 20 mg | 4-thiazole carboxylic acid | 27 mg |
| 255 | 73 | 20 mg | 3-chloro thiophene-2-carboxylic acid | 34 mg |
| 256 | 73 | 20 mg | 6-methylnicotinic acid | 29 mg |
| 257 | 73 | 20 mg | 6-chloro pyridine-2-carboxylic acid | 33 mg |
| 258 | 73 | 20 mg | 6-fluoro pyridine-2-carboxylic acid | 30 mg |
| 259 | 73 | 20 mg | 1-methyl indole-2-carboxylic acid | 37 mg |
| 260 | 73 | 20 mg | 3-chloropyridine-2-carboxylic acid | 33 mg |
| 262 | 73 | 20 mg | 2-fluoro nicotinic acid | 30 mg |
| 263 | 73 | 20 mg | 4-cyano benzoic acid | 31 mg |
| 264 | 73 | 20 mg | 3-cyano benzoic acid | 31 mg |
| 265 | 73 | 20 mg | 3-(trifluoromethyl)benzoic acid | 40 mg |
| 266 | 73 | 20 mg | 2-pyridylacetic acid | 36 mg |
| 267 | 73 | 20 mg | 3-pyridylacetic acid | 36 mg |
| 268 | 73 | 20 mg | (4-pyridylthio) acetic acid | 36 mg |

TABLE 17-continued

| | | | | |
|---|---|---|---|---|
| 270 | 261 | 20 mg | 4-(trifluoromethyl)nicotinic acid | 39 mg |
| 271 | 261 | 20 mg | 3-chloropyridine-2-carboxylic acid | 32 mg |

| | | | | Mass spectrometric data | |
|---|---|---|---|---|---|
| Compound No. | Reaction reagent 2 | Solvent | Yield | Measuring Method | Data |
| 248 | EDCI 28 mg, DMAP 8 mg | DMF | 17.2 mg | FAB | 723 (M + H)+ |
| 249 | [(CH3)2CH]2NEt 18 mg | DMF | 1.2 mg | ESI | 614 (M + H)+ |
| 250 | EDCI 84 mg, DMAP 5 mg | DMF | 23.2 mg | ESI | 770 (M + H)+ |
| 251 | EDCI 28 mg, DMAP 8 mg | DMF | 7.6 mg | ESI | 763 (M + H)+ |
| 252 | EDCI 28 mg, DMAP 8 mg | DMF | 10.9 mg | ESI | 711 (M + H)+ |
| 253 | EDCI 28 mg, DMAP 8 mg | DMF | 10.9 mg | ESI | 676 (M + H)+ |
| 254 | EDCI 28 mg, DMAP 8 mg | DMF | 18.5 mg | ESI | 681 (M + H)+ |
| 255 | EDCI 28 mg, DMAP 8 mg | DMF | 15.8 mg | ESI | 714 (M + H)+ |
| 256 | EDCI 28 mg, DMAP 8 mg | DMF | 15.1 mg | ESI | 689 (M + H)+ |
| 257 | EDCI 28 mg, DMAP 8 mg | DMF | 12.7 mg | ESI | 709 (M + H)+ |
| 258 | EDCI 28 mg, DMAP 8 mg | DMF | 14.4 mg | ESI | 693 (M + H)+ |
| 259 | EDCI 28 mg, DMAP 8 mg | DMF | 18.8 mg | ESI | 727 (M + H)+ |
| 260 | EDCI 28 mg, DMAP 8 mg | DMF | 14.6 mg | ESI | 709 (M + H)+ |
| 262 | EDCI 28 mg, DMAP 8 mg | DMF | 9.9 mg | ESI | 693 (M + H)+ |
| 263 | EDCI 28 mg, DMAP 8 mg | DMF | 14.0 mg | ESI | 699 (M + H)+ |
| 264 | EDCI 28 mg, DMAP 8 mg | DMF | 16.9 mg | ESI | 699 (M + H)+ |
| 265 | EDCI 28 mg, DMAP 8 mg | DMF | 14.3 mg | ESI | 742 (M + H)+ |
| 266 | EDCI 28 mg, DMAP 8 mg | DMF | 11.7 mg | ESI | 689 (M + H)+ |
| 267 | EDCI 28 mg, DMAP 8 mg | DMF | 8.6 mg | ESI | 689 (M + H)+ |
| 268 | EDCI 28 mg, DMAP 4 mg | DMF | 16.5 mg | ESI | 721 (M + H)+ |
| 270 | EDCI 26 mg, DMAP 4 mg | DMF | 8.3 mg | ESI | 767 (M + H)+ |
| 271 | EDCI 26 mg, DMAP 4 mg | DMF | 14.5 mg | ESI | 733 (M + H)+ |

TABLE 18

| Compound No. | $^1$H-NMR δ (ppm) |
|---|---|
| 73 | 0.91 (3H, s), 1.13 (3H, t, J = 5.1 Hz), 1.14 (3H, t, J = 5.1 Hz), 1.26 (1H, s), 1.32-1.40 (1H, m), 1.42 (3H, s), 1.45 (1H, d, J = 2.7 Hz), 1.49-1.51 (2H, m), 1.66 (3H, s), 1.81-1.91 (2H, m), 2.13-2.18 (1H, m), 2.24-2.37 (4H, m), 2.90 (1H, m), 3.79 (3H, m), 4.80 (1H, dd, J = 3.5, 7.6 Hz), 4.99-5.00 (1H, m), 6.52 (1H, s), 7.42 (1H, dd, J = 3.5, 5.4 Hz), 8.11 (1H, dt, J = 1.4, 5.4 Hz), 8.70 (1H, d, J = 2.4 Hz), 9.00 (1H, s) |
| 77 | 0.92 (3H, s), 1.14 (3H, t, J = 7.6 Hz), 1.20 (3H, t, J = 7.6 Hz), 1.26 (1H, s), 1.37-1.46 (1H, m), 1.51 (3H, s), 1.62 (1H, d, J = 3.8 Hz), 1.68-1.82 (2H, m), 1.87 (3H, s), 1.91-2.00 (2H, m), 2.18-2.23 (1H, m), 2.33 (2H, q, J = 7.6 Hz), 2.43 (2H, dq, J = 1.4, 7.6 Hz), 2.97 (1H, m), 3.70 (1H, d, J = 11.9 Hz), 3.84 (1H, d, J = 11.9 Hz), 4.83 (1H, dd, J = 5.1, 11.1 Hz), 5.05 (1H, m, J = 4.3 Hz), 5.27 (1H, dd, J = 4.6, 11.1 Hz), 6.45 (1H, s), 7.39-7.66 (4H, m), 8.05-8.13 (3H, m), 8.70 (1H, d, J = 4.6 Hz), 9.00 (1H, s) |
| 74 | 0.90 (3H, s), 1.12 (3H, t, J = 7.8 Hz), 1.13 (3H, t, J = 7.8 Hz), 1.19 (1H, s), 1.25-1.34 (1H, m), 1.44 (3H, s), 1.53-1.63 (3H, m), 1.69 (3H, s), 1.73-1.90 (2H, m), 2.10 (1H, m), 2.16 (3H, s), 2.33 (2H, dq, J = 2.4, 7.6 Hz), 2.36 (2H, dq, J = 3.2, 7.6 Hz), 2.87 (1H, m), 3.72 (2H, m), 4.81 (1H, dd, J = 4.6, 11.6 Hz), 4.97-5.00 (2H, m), 6.46 (1H, s), 7.40 (1H, dd, J = 4.6, 8.1 Hz), 8.10 (1H, m), 8.69 (1H, d, J = 4.9 Hz), 9.00 (1H, s) |
| 205 | 0.92 (3H, s), 1.14 (3H, t, J = 7.6 Hz), 1.20 (3H, t, J = 7.6 Hz), 1.26 (1H, s), 1.42-1.50 (1H, m), 1.59 (3H, s), 1.61-1.83 (3H, m), 1.85 (3H, s), 1.83-2.00 (2H, m), 2.18-2.23 (1H, m), 2.33 (2H, q, J = 7.6 Hz), 2.43 (2H, q, J = 7.6 Hz), 2.94 (1H, m), 3.72 (1H, d, J = 11.9 Hz), 3.82 (1H, d, J = 12.7 Hz), 4.83 (1H, dd, J = 4.9, 11.3 Hz), 5.03-5.06 (1H, m), 5.27 (1H, dd, J = 4.9, 11.3 Hz), 6.42 (1H, s), 7.38 (1H, dd, J = 4.9, 8.1 Hz), 7.45 (1H, dd, J = 4.9, 8.1 Hz), 8.07 (1H, dt, J = 2.2, 8.1 Hz), 8.36 (1H, dt, J = 1.9, 8.1 Hz), 8.67 (1H, dd, J = 1.9, 5.1 Hz), 8.83 (1H, dd, J = 1.9, 4.9 Hz), 8.97 (1H, d, J = 1.9 Hz), 9.30 (1H, d, J = 1.9 Hz) |
| 206 | 0.90 (3H, s), 1.13 (6H, t, J = 7.6 Hz), 1.19 (1H, s), 1.24 (3H, d, J = 4.6 Hz), 1.26 (3H, d, J = 4.6 Hz), 1.33-1.38 (1H, m), 1.45 (3H, s), 1.54 (1H, d, J = 3.8 Hz), 1.60-1.64 (2H, m), 1.67 (3H, s), 1.75-1.90 (2H, m), 2.15-2.19 (1H, m), 2.32 (2H, q, J = 7.6 Hz), 2.38 (2H, q, J = 7.6 Hz), 2.65 (1H, quint, J = 7.6 Hz), 2.88 (1H, d, J = 1.6 Hz), 3.68 (1H, d, J = 12.4 Hz), 3.83 (1H, d, J = 11.9 Hz), 4.80 (1H, dd, J = 4.9, 11.3 Hz), 5.00 (2H, m), |

TABLE 18-continued

| Compound No. | $^1$H-NMR δ (ppm) |
|---|---|
| | 6.38 (1H, s), 7.40 (1H, dd, J = 4.6, 8.1 Hz), 8.09 (1H, dt, J = 1.9, 8.1 Hz), 8.69 (1H, dd, J = 1.6, 4.6 Hz), 9.00 (1H, d, J = 1.6 Hz) |

TABLE 19

| 化合物番号 | $^1$H-NMR δ (ppm) |
|---|---|
| 208 | 0.92 (3H, s), 1.14 (3H, t, J = 7.6 Hz), 1.21 (3H, t, J = 7.6 Hz), 1.26 (1H, s), 1.39-1.47 (1H, m), 1.50 (3H, s), 1.61 (1H, m), 1.68-1.83 (2H, m), 1.86 (3H, s), 1.91-2.05 (2H, m), 2.18-2.23 (1H, m), 2.33 (2H, q, J = 7.6 Hz), 2.43 (2H, dq, J = 1.4, 7.6 Hz), 2.95 (1H, d, J = 2.4 Hz), 3.72 (1H, d, J = 11.9 Hz), 3.82 (1H, d, J = 11.9 Hz), 4.83 (1H, dd, J = 5.1, 11.1 Hz), 5.03-5.06 (1H, m), 5.26 (1H, dd, J = 4.9, 11.1 Hz), 6.40 (1H, s), 7.38 (1H, dd, J = 4.9, 8.4 Hz), 7.76 (2H, d, J = 8.4 Hz), 8.06 (1H, dt, J = 2.2, 8.1 Hz), 8.22 (2H, d, J = 8.4 Hz), 8.66 (1H, dd, J = 1.6, 4.9 Hz), 8.96 (1H, d, J = 2.2 Hz) |
| 211 | 0.90 (3H, s), 1.14 (3H, t, J = 7.6 Hz), 1.15 (3H, t, J = 7.6 Hz), 1.26 (1H, s), 1.29-1.38 (1H, m), 1.41 (3H, s), 1.43-1.71 (5H, m), 1.59 (3H, s), 1.75-1.89 (6H, m), 2.12-2.17 (1H, m), 2.26-2.38 (4H, m), 2.86 (1H, m), 3.45-4.00 (5H, m), 4.82 (1H, dd, J = 5.4, 10.8 Hz), 4.97-5.03 (2H, m), 6.41 (1H, s), 7.40 (1H, dd, J = 4.9, 7.8 Hz), 8.07-8.13 (1H, m), 8.67-8.70 (1H, m), 9.01 (1H, d, J = 2.4 Hz) |
| 212 | 0.92 (3H, s), 1.14 (3H, t, J = 7.6 Hz), 1.20 (3H, t, J = 7.6 Hz), 1.26 (1H, s), 1.38-1.46 (1H, m), 1.50 (3H, s), 1.61 (1H, m), 1.66-1.78 (2H, m), 1.84 (3H, s), 1.87-1.99 (2H, m), 2.12-2.23 (1H, m), 2.31 (2H, q, J = 7.6 Hz), 2.41 (2H, q, J = 7.6 Hz), 2.95 (1H, m), 3.73 (1H, d, J = 11.9 Hz), 3.81 (1H, d, J = 11.9 Hz), 4.83 (1H, dd, J = 4.9, 11.3 Hz), 5.04 (1H, m), 5.25 (1H, dd, J = 4.9, 11.3 Hz), 6.40 (1H, s), 7.38 (1H, dd, J = 4.6, 7.8 Hz), 7.478 (1H, d, J = 8.1 Hz), .06 (1H, dt, J = 1.6, 7.8 Hz), 8.30 (1H, dd, J = 2.4, 8.1 Hz), 8.67 (1H, dd, J = 1.4, 4.6 Hz), 8.97 (1H, d, J = 2.4 Hz), 9.06 (1H, d, J = 2.7 Hz) |
| 213 | 0.90 (3H, s), 0.93 (2H, d, J = 2.7 Hz), 0.96 (2H, d, J = 2.7 Hz), 1.03-1.19 (6H, m), 1.26 (1H, s), 1.32-1.39 (1H, m), 1.45 (3H, s), 1.52 (1H, d, J = 3.8 Hz), 1.61-1.69 (3H, m), 1.71 (3H, s), 1.73-1.94 (2H, m), 2.14-2.19 (1H, m), 2.24-2.40 (4H, m), 2.95 |

TABLE 19-continued

| 化合物番号 | ¹H-NMR δ (ppm) |
|---|---|
| | (1H, m), 3.68 (1H, d, J = 11.9 Hz), 3.81 (1H, d, J = 11.9 Hz), 4.79 (1H, dd, J = 5.4, 11.3 Hz), 4.96-5.00 (2H, m), 6.45 (1H, s), 7.40 (1H, dd, J = 4.6, 8.1 Hz), 8.10 (1H, dt, J = 1.9, 8.1 Hz), 8.68 (1H, m), 9.01 (1H, m) |
| 214 | 0.90 (3H, s), 1.13 (3H, t, J = 7.6 Hz), 1.17 (3H, t, J = 7.6 Hz), 1.26 (1H, s), 1.34-1.40 (1H, m), 1.44 (3H, s), 1.54 (1H, d, J = 4.3 Hz), 1.61-1.67 (2H, m), 1.69 (3H, s), 1.72-2.42 (13H, m), 2.91 (1H, m), 3.23 (1H, quint., J = 8.1 Hz), 3.69 (1H, d, J = 11.9 Hz), 3.81 (1H, d, J = 11.9 Hz), 4.80 (1H, dd, J = 4.9, 11.3 Hz), 4.99-5.04 (2H, m), 6.40 (1H, s), 7.39 (1H, dd, J = 4.9, 8.1 Hz), 8.09 (1H, dt, J = 1.6, 8.1 Hz), 8.69 (1H, dd, J = 1.6, 4.6 Hz), 9.01 (1H, d, J = 1.6 Hz) |
| 215 | 0.90 (3H, s), 1.13 (3H, t, J = 7.6 Hz), 1.17 (3H, t, J = 7.6 Hz), 1.26 (1H, s), 1.41-1.46 (1H, m), 1.59 (3H, s), 1.65-1.68 (3H, m), 1.73 (3H, s), 1.84-1.90 (2H, m), 2.18 (1H, m), 2.31 (2H, q, J = 7.6 Hz), 2.38 (2H, q, J = 7.6 Hz), 2.93 (1H, m), 3.69 (1H, d, J = 11.9 Hz), 3.81 (1H, d, J = 11.9 Hz), 4.80 (1H, m), 5.01-5.09 (2H, m), 5.92 (1H, dd, J = 1.6, 10.5 Hz), 6.15-6.24 (1H, m), 6.45 (1H, s), 6.45-6.53 (1H, m), 7.40 (1H, dd, J = 4.6, 7.8 Hz), 8.07-8.11 (1H, m), 8.68 (1H, dd, J = 1.9, 4.9 Hz), 9.00 (1H, d, J = 2.2 Hz) |

TABLE 20

| 化合物番号 | ¹H-NMR δ (ppm) |
|---|---|
| 216 | 0.92 (3H, s), 1.14 (3H, t, J = 7.6 Hz), 1.20 (3H, t, J = 7.6 Hz), 1.26 (1H, s), 1.38-1.42 (1H, m), 1.50 (3H, s), 1.64-1.78 (3H, m), 1.85 (3H, s), 1.88-2.05 (2H, m), 2.17-2.23 (1H, m), 2.33 (2H, q, J = 7.6 Hz), 2.42 (2H, dq, J = 1.1, 7.6 Hz), 2.99 (1H, m), 3.72 (1H, d, J = 12.4 Hz), 3.81 (1H, d, J = 11.5 Hz), 4.83 (1H, dd, J = 4.9, 11.5 Hz), 5.03-5.05 (1H, m), 5.25 (1H, dd, J = 5.4, 11.5 Hz), 6.41 (1H, s), 7.37 (1H, dd, J = 5.2, 8.1 Hz), 7.91 (2H, dd, J = 1.6, 4.6 Hz), 8.07 (1H, dt, J = 1.6, 8.1 Hz), 8.67 (1H, dd, J = 1.9, 4.9 Hz), 8.83 (2H, dd, J = 1.6, 4.3 Hz), 8.97 (1H, d, J = 1.6 Hz) |
| 217 | 0.91 (3H, s), 1.13 (3H, t, J = 7.6 Hz), 1.20 (3H, t, J = 7.6 Hz), 1.26 (1H, s), 1.37-1.46 (1H, m), 1.50 (3H, s), 1.63-1.75 (3H, m), 1.87 (3H, s), 1.83-1.96 (2H, m), 2.13-2.23 (1H, m), 2.32 (2H, q, J = 7.6 Hz), 2.41 (2H, dq, J = 1.4, 7.6 Hz), 2.99 (1H, m), 3.67 (1H, d, J = 11.9 Hz), 3.83 (1H, d, J = 11.9 Hz), 4.83 (1H, dd, J = 5.4, 11.3 Hz), 4.98-5.06 (1H, m), 5.38 (1H, dd, J = 5.4, 10.8 Hz), 6.43 (1H, s), 7.35-7.44 (1H, m), 7.50-7.55 (1H, m), 7.89 (1H, dt, J = 1.6, 7.6 Hz), 8.07 (1H, dt, J = 1.6, 8.1 Hz), 8.18 (1H, d, J = 7.6 Hz), 8.67 (1H, dd, J = 1.6, 4.9 Hz), 8.82-8.84 (1H, m), 8.97 (1H, d, J = 2.4 Hz) |
| 218 | 0.83-1.12 (12H, m), 0.91 (3H, s), 1.26 (1H, s), 1.33-1.41 (1H, m), 1.45 (3H, s), 1.52-1.69 (6H, m), 1.71 (3H, s), 1.81-1.93 (2H, m), 2.14-2.18 (1H, m), 2.92 (1H, m), 3.72 (1H, d, J = 11.9 Hz), 3.82 (1H, d, J = 11.9 Hz), 4.80 (1H, dd, J = 4.9, 11.4 Hz), 4.99-5.04 (2H, m), 6.46 (1H, s), 7.41 (1H, dd, J = 4.9, 8.3 Hz), 8.10 (1H, dt, J = 1.7, 8.3 Hz), 8.69 (1H, dd, J = 1.5, 4.9 Hz), 9.01 (1H, d, J = 1.4 Hz) |
| 219 | 0.90 (3H, s), 1.26 (1H, s), 1.32-1.41 (1H, m), 1.44 (3H, s), 1.51-1.63 (3H, m), 1.69 (3H, s), 1.79-2.04 (8H, m), 2.17-2.40 (14H, m), 2.89 (1H, m), 3.08-3.26 (3H, m), 3.67 (1H, d, J = 11.9 Hz), 3.78 (1H, d, J = 11.9 Hz), 4.79 (1H, dd, J = 5.4, 11.1 Hz), 4.97-5.00 (2H, m), 6.41 (1H, s), 7.41 (1H, dd, J = 4.9, 8.1 Hz), 8.09 (1H, dt, J = 1.9, 8.4 Hz), 8.68 (1H, m), 9.00 (1H, m) |
| 220 | 1.17 (3H, s), 1.26 (1H, s), 1.57 (3H, s), 1.65 (1H, m), 1.77-1.82 (2H, m), 1.88 (3H, s), 1.94-2.05 (3H, m), 2.13-2.31 (1H, m), 2.95 (1H, m), 4.16 (2H, s), 5.06 (1H, dd, J = 2.4, 6.5 Hz), 5.17-5.32 (2H, m), 6.42 (1H, s), 7.34-7.64 (10H, m), 8.01-8.12 (7H, m), 8.66 (1H, dd, J = 1.6, 5.1 Hz), 8.97 (1H, d, J = 1.9 Hz) |
| 221 | 0.92 (3H, s), 1.14 (3H, t, J = 7.6 Hz), 1.21 (3H, t, J = 7.6 Hz), 1.26 (1H, s), 1.44 (1H, m), 1.50 (3H, s), 1.57-1.62 (1H, m), 1.67-1.80 (2H, m), 1.85 (3H, s), 1.91-1.95 (2H, m), 2.17-2.24 (1H, m), 2.33 (2H, q, J = 7.6 Hz), 2.42 (2H, q, J = 7.6 Hz), 2.92 (1H, m), 3.74 (1H, d, J = 11.9 Hz), 3.81 (1H, d, J = 11.9 Hz), 4.84 (1H, dd, J = 4.9, 11.1 Hz), 5.04 (1H, m), 5.27 (1H, dd, J = 4.9, 11.1 Hz), 6.40 (1H, s), 7.38 (1H, dd, J = 4.9, 8.1 Hz), 7.84 (1H, d, J = 8.4 Hz), 8.05-8.08 (1H, m), 8.54 (1H, d, J = 8.1 Hz), 8.67 (1H, d, J = 4.6 Hz), 8.96 (1H, d, J = 2.2 Hz), 9.38 (1H, s) |

TABLE 21

| 化合物番号 | ¹H-NMR δ (ppm) |
|---|---|
| 222 | 0.94 (3H, s), 1.14 (3H, t, J = 7.6 Hz), 1.19 (3H, t, J = 7.6 Hz), 1.26 (1H, s), 1.38-1.47 (1H, m), 1.48 (3H, s), 1.57-1.71 (3H, m), 1.75 (3H, s), 1.83-1.97 (2H, m), 2.10-2.22 (1H, m), 2.33 (2H, q, J = 7.6 Hz), 2.41 (2H, dq, J = 1.6, 7.6 Hz), 2.96 (1H, m), 3.74-3.80 (2H, m), 4.83 (1H, dd, J = 5.7, 11.6 Hz), 5.02-5.03 (1H, m), 5.28 (1H, dd, J = 5.4, 11.6 Hz), 6.41 (1H, s), 7.40 (1H, dd, J = 5.4, 7.6 Hz), 7.69 (1H, d, J = 5.4 Hz), 8.08 (1H, dt, J = 2.2, 8.1 Hz), 8.69 (1H, dd, J = 1.6, 4.9 Hz), 8.97 (1H, d, J = 4.6 Hz), 9.00 (1H, d, J = 2.4 Hz), 9.16 (1H, s) |
| 223 | 0.94 (3H, s), 1.26 (1H, s), 1.37 (1H, m), 1.47 (3H, s), 1.48-1.66 (3H, m), 1.71 (3H, s), 1.75-1.96 (2H, m), 2.17-2.24 (1H, m), 2.96 (1H, m), 3.14-3.35 (6H, m), 3.85 (1H, d, J = 12.2 Hz), 3.93 (1H, d, J = 12.2 Hz), 4.87 (1H, dd, J = 5.7, 10.8 Hz), 4.99-5.08 (2H, m), 6.41 (1H, s), 7.41 (1H, dd, J = 4.6, 8.1 Hz), 8.09 (1H, m), 8.69 (1H, m), 9.02 (1H, m) |
| 224 | 0.91 (3H, s), 1.13 (3H, t, J = 7.3 Hz), 1.17 (3H, t, J = 7.3 Hz), 1.26 (1H, s), 1.40 (1H, m), 1.45 (3H, s), 1.58-1.63 (3H, m), 1.70 (3H, s), 1.73-1.89 (2H, m), 2.10-2.18 (1H, m), 2.32 (2H, q, J = 7.6 Hz), 2.36 (2H, q, J = 7.6 Hz), 2.96 (1H, m), 3.25 (1H, d, J = 9.7 Hz), 3.32 (1H, d, J = 9.7 Hz), 3.69-3.81 (2H, m), 4.80 (1H, dd, J = 5.4, 11.3 Hz), 5.00-5.08 (2H, m), 6.40 (1H, s), 7.41 (1H, dd, J = 4.9, 8.1 Hz), 8.09 (1H, m), 8.69 (1H, dd, J = 1.4, 5.1 Hz), 9.01 (1H, d, J = 2.4 Hz) |
| 225 | 0.88 (3H, s), 1.13 (3H, t, J = 7.6 Hz), 1.19 (3H, t, J = 7.5 Hz), 1.22 (3H, t, J = 7.6 Hz), 1.24 (3H, s), 1.26 (1H, m), 1.50-1.55 (1H, m), 1.56 (3H, s), 1.55-1.64 (3H, m), 1.70-1.84 (2H, m), 2.31 (2H, dq, J = 1.2, 7.8 Hz), 2.42 (2H, dq, J = 3.4, 13.6 Hz), 52.44 (2H, dq, J = 2.0, 7.5 Hz), 2.79 (1H, dt, J = 1.4, .1 Hz), 3.69 (1H, d, J = 11.9 Hz), 3.79 (1H, d, J = 11.9 Hz), 4.79 (1H, dd, J = 4.9, 11.4 Hz), 5.24 (1H, d, J = 4.9, 11.4 Hz), 6.45 (1H, s), 7.47 (1H, d, J = 8.5 Hz), 8.12 (1H, dd, J = 2.7, 8.5 Hz), 8.83 (1H, d, J = 2.7 Hz) |
| 226 | 0.89 (3H, s), 1.13 (3H, t, J = 7.6 Hz), 1.19 (3H, t, J = 7.6 Hz), 1.10-1.24 (3H, m), 1.26 (1H, s), 1.31-1.39 (1H, m), 1.44 (3H, s), 1.53 (1H, d, J = 3.8 Hz), 1.61-1.67 (2H, m), 1.69 (3H, s), 1.72-1.92 (2H, m), 2.08-2.18 (1H, m), 2.31 (2H, q, J = 7.6 Hz), 2.44 (2H, dq, J = 1.6, 7.6 Hz), 2.26-2.64 (2H, m), 2.85 (3H, s), 3.69 (1H, d, J = 11.9 Hz), 3.80 (1H, d, J = 11.9 Hz), 4.80 (1H, dd, J = 5.4, 11.3 Hz), 4.92-5.10 (2H, m), 6.41 (1H, s), 7.44 (1H, d, J = 8.4 Hz), 8.05 (1H, dd, J = 2.4, 8.4 Hz), 8.78 (1H, d, J = 2.4 Hz) |
| 227 | 0.88 (3H, s), 1.14 (3H, t, J = 7.6 Hz), 1.20 (3H, t, J = 7.6 Hz), 1.23-1.33 (1H, m), 1.43 (1H, m), 1.49 (3H, s), 1.61-1.74 (3H, m), 1.82 (3H, s), 1.87-2.23 (3H, m), 2.33 (2H, q, J = 7.6 Hz), 2.42 (2H, q, J = 7.6 Hz), 2.96 (1H, m), 3.73 (1H, d, J = 12.4 Hz), 3.82 (1H, d, J = 12.4 Hz), 4.83 (1H, dd, J = 5.4, 11.3 Hz), 5.03 (1H, m), 5.26 (1H, dd, J = 5.4, 11.3 Hz), 6.43 (1H, s), 7.39 (1H, dd, J = 4.9, 8.1 Hz), 7.86 (1H, t, J = 5.4 Hz), 8.08 (1H, dt, J = 1.9, 7.8 Hz), 8.60 (1H, d, J = 2.2 Hz), 8.66-8.68 (2H, m), 8.98 (1H, d, J = 2.2 Hz) |

TABLE 22

| 化合物番号 | ¹H-NMR δ (ppm) |
|---|---|
| 228 | 0.93 (3H, s), 1.14 (3H, t, J = 7.6 Hz), 1.20 (3H, t, J = 7.6 Hz), 1.26 (1H, s), 1.32-1.44 (1H, m), 1.49 (3H, s), 1.61 (1H, d, J = 4.1 Hz), 1.67-1.75 (2H, m), 1.81 (3H, s), 1.79-2.05 (2H, m), 2.13-2.22 (1H, m), 2.33 (2H, q, J = 7.6 Hz), 2.42 (2H, dq, J = 1.4, 7.6 Hz), 2.92 (1H, m), 3.74 (1H, d, J = 11.9 Hz), 3.82 (1H, d, J = 11.9 Hz), 4.84 (1H, dd, J = 5.4, 10.8 Hz), 5.04 (1H, m), 5.27 (1H, dd, J = 5.4, 10.8 Hz), 6.43 (1H, s), 7.40 (1H, dd, J = 4.9, 8.1 Hz), 7.74 (1H, d, J = 5.1 Hz), 8.08 (1H, dt, J = 2.2, 8.1 Hz), 8.65 (1H, d, J = 4.9 Hz), 8.69 (1H, dd, J = 4.1, 7.6 Hz), 8.78 (1H, s), 8.99 (1H, d, J = 1.9 Hz) |
| 229 | 0.92 (3H, s), 1.14 (3H, t, J = 7.6 Hz), 1.19 (3H, t, J = 6.5 Hz), 1.26 (1H, s), 1.34-1.45 (1H, m), 1.49 (3H, s), 1.62 (1H, m), 1.71-1.77 (2H, m), 1.83 (3H, s), 1.88-2.01 (2H, m), 2.14-2.22 (1H, m), 2.33 (2H, q, J = 7.6 Hz), 2.42 (2H, dq, J = 2.2, 7.6 Hz), 2.64 (3H, s), 2.96 (1H, m), 3.72 (1H, d, J = 11.9 Hz), 3.84 (1H, d, J = 11.9 Hz), 4.84 (1H, dd, J = 5.4, 11.3 Hz), 5.04 (1H, m), 5.36 (1H, dd, J = 5.4, 10.8 Hz), 6.42 (1H, s), 7.35-7.42 (2H, m), 7.66 (1H, d, J = 7.8 Hz), 8.08 (1H, dt, J = 1.9, 7.8 Hz), 8.60 (1H, d, J = 4.1 Hz), 8.68 (1H, dd, J = 1.6, 4.9 Hz), 8.98 (1H, d, J = 2.4 Hz), |

TABLE 22-continued

| 化合物番号 | $^1$H-NMR δ (ppm) |
| --- | --- |
| 230 | 0.78 (3H, s), 1.09 (3H, t, J = 7.8 Hz), 1.12 (3H, t, J = 7.8 Hz), 1.26 (1H, s), 1.33 (3H, s), 1.36-1.38 (1H, m), 1.40-1.48 (2H, m), 1.55 (3H, s), 1.59-1.85 (2H, m), 2.09-2.18 (1H, m), 2.32 (4H, q, J = 7.6 Hz), 2.96 (1H, m), 3.40 (1H, d, J = 11.9 Hz), 3.75 (1H, d, J = 11.9 Hz), 4.72 (1H, dd, J = 4.9, 11.3 Hz), 4.95 (1H, m), 5.17 (1H, dd, J = 5.4, 11.9 Hz), 6.45 (1H, s), 7.40 (1H, dd, J = 4.9, 8.1 Hz), 7.49-7.67 (3H, m), 7.83-7.88 (4H, m), 8.02 (1H, s), 8.07 (1H, dt, J = 2.2, 8.1 Hz), 8.68 (1H, dd, J = 1.4, 4.6 Hz), 8.95 (1H, dd, J = 1.6, 4.6 Hz), 8.99 (1H, d, J = 1.9 Hz) |
| 231 | 0.91 (3H, s), 1.09 (3H, t, J = 7.6 Hz), 1.14 (3H, t, J = 7.6 Hz), 1.18 (3H, t, J = 7.6 Hz), 1.26 (1H, s), 1.34-1.43 (1H, m), 1.48 (3H, s), 1.63 (1H, m), 1.67-1.75 (2H, m), 1.80 (3H, s), 1.83-2.08 (4H, m), 2.17-2.25 (1H, m), 2.32 (2H, q, J = 7.6 Hz), 2.40 (2H, dq, J = 7.6, 1.9 Hz), 2.96 (1H, m), 3.64 (1H, d, J = 11.9 Hz), 3.87 (1H, d, J = 11.9 Hz), 4.05 (2H, t, J = 6.2 Hz), 4.82 (1H, dd, J = 5.4, 10.8 Hz), 5.04 (1H, m), 5.40 (1H, dd, J = 5.4, 10.8 Hz), 6.47 (1H, s), 7.19-7.44 (3H, m), 8.08 (1H, dt, J = 1.9, 8.1 Hz), 8.32 (1H, dd, J = 1.6, 4.3 Hz), 8.68 (1H, dd, J = 4.6, 1.6 Hz), 8.98 (1H, d, J = 1.6 Hz) |
| 232 | 0.92 (3H, s), 1.14 (3H, t, J = 7.6 Hz), 1.20 (3H, t, J = 7.6 Hz), 1.26 (1H, s), 1.34-1.43 (1H, m), 1.50 (3H, s), 1.61 (1H, m), 1.67-1.78 (2H, m), 1.84 (3H, s), 1.87-1.97 (2H, m), 2.13-2.23 (1H, m), 2.18 (1H, s), 2.32 (2H, q, J = 7.6 Hz), 2.42 (2H, dq, J = 1.4, 7.6 Hz), 3.73 (1H, d, J = 11.9 Hz), 3.80 (1H, d, J = 11.9 Hz), 4.83 (1H, dd, J = 5.4, 11.1 Hz), 5.04 (1H, m, J = 3.8 Hz), 5.25 (1H, dd, J = 5.1, 11.1 Hz), 6.41 (1H, s), 7.06 (1H, dd, J = 3.0, 8.6 Hz), 7.38 (1H, m, J = 4.9, 8.1 Hz), 8.08 (1H, dt, J = 1.9, 8.1 Hz), 8.43-8.50 (1H, m), 8.67 (1H, dd, J = 1.6, 4.6 Hz), 8.95-8.98 (2H, m) |

TABLE 23

| 化合物番号 | $^1$H-NMR δ (ppm) |
| --- | --- |
| 233 | 0.91 (3H, s), 1.26 (1H, s), 1.45 (3H, s), 1.70 (3H, s), 1.32-1.97 (29H, m), 2.14-2.19 (1H, m), 2.66-2.90 (3H, m), 3.06 (1H, s), 3.67 (1H, d, J = 11.9 Hz), 3.78 (1H, d, J = 11.9 Hz), 4.78 (1H, dd, J = 5.4, 10.8 Hz), 4.98-5.01 (2H, m), 6.40 (1H, s), 7.42 (1H, dd, J = 4.9, 8.1 Hz), 8.11 (1H, dt, J = 1.6, 8.1 Hz), 8.69 (1H, d, J = 4.6 Hz), 9.01 (1H, s) |
| 234 | 0.91 (3H, s), 1.45 (3H, s), 1.70 (3H, s), 1.10-2.05 (37H, m), 2.14-2.49 (3H, m), 3.04 (1H, s), 3.65 (1H, d, J = 11.3 Hz), 3.77 (1H, d, J = 11.9 Hz), 4.78 (1H, dd, J = 5.4, 10.8 Hz), 4.97-5.01 (2H, m), 6.41 (1H, s), 7.42 (1H, dd, J = 4.9, 8.1 Hz), 8.11 (1H, dd, J = 1.9, 8.1 Hz), 8.69 (1H, d, J = 4.3 Hz), 9.01 (1H, s) |
| 235 | 1.00 (3H, s), 1.25-1.33 (1H, s), 1.48 (3H, s), 1.55 (1H, m), 1.71 (1H, m), 1.75 (3H, s), 1.79-1.98 (2H, m), 2.11-2.21 (1H, m), 3.48 (2H, s), 3.54 (2H, s), 3.60 (2H, s), 3.90 (1H, d, J = 11.9 Hz), 3.99 (1H, d, J = 11.9 Hz), 4.86 (1H, m), 4.98 (1H, m), 5.07-5.12 (1H, m), 6.53 (1H, m), 7.53 (1H, dd, J = 4.9, 8.1 Hz), 8.23 (1H, m), 8.30 (1H, m), 8.70 (1H, m), 9.05 (1H, m) |
| 236 | 0.11-0.27 (8H, m), 0.52-0.65 (8H, m), 0.88 (3H, s), 0.99-1.14 (5H, m), 1.15 (3H, s), 1.25-1.43 (2H, m), 1.61-1.76 (4H, m), 1.72 (3H, s), 2.18-2.54 (9H, m), 3.74 (1H, d, J = 11.9 Hz), 3.83 (1H, d, J = 11.9 Hz), 4.86 (1H, dd, J = 4.6, 11.6 Hz), 5.01-5.12 (2H, m), 6.41 (1H, s), 7.45 (1H, dd, J = 4.9, 7.8 Hz), 8.16 (1H, m), 8.71 (1H, m), 9.02 (1H, s) |
| 237 | 0.14-0.26 (6H, m), 0.52-0.64 (6H, m), 0.92 (3H, s), 0.97-1.16 (4H, m), 1.26-1.38 (1H, m), 1.45 (3H, s), 1.52 (1H, m), 1.63-1.70 (2H, m), 1.70 (3H, s), 1.82-1.91 (2H, m), 2.12-2.41 (7H, m), 2.96 (1H, m), 3.74 (1H, d, J = 11.9 Hz), 3.86 (1H, d, J = 11.9 Hz), 4.84 (1H, dd, J = 4.9, 11.3 Hz), 5.00-5.03 (2H, m), 6.43 (1H, s), 7.42 (1H, dd, J = 4.6, 7.8 Hz), 8.11 (1H, m), 8.70 (1H, d, J = 4.3 Hz), 9.01 (1H, s) |
| 238 | 0.91 (3H, s), 1.26 (1H, s), 1.44 (3H, s), 1.45 (3H, s), 1.46 (3H, s), 1.34-1.53 (7H, m), 1.52 (1H, m), 1.70 (3H, s), 1.81-2.02 (2H, m), 2.15-2.31 (3H, m), 2.96 (1H, m), 3.67 (1H, m), 4.00 (1H, m), 4.85-5.00 (3H, m), 6.46 (1H, m), 7.45 (1H, dd, J = 4.9, 8.1 Hz), 8.13 (1H, m), 8.70 (1H, m), 9.02 (1H, s) |
| 239 | 0.93 (3H, s), 1.14 (3H, t, J = 7.6 Hz), 1.20 (3H, t, J = 7.6 Hz), 1.26 (1H, s), 1.33-1.44 (1H, m), 1.50 (3H, s), 1.61 (1H, m), 1.68-1.77 (2H, m), 1.84 (3H, s), 1.91-1.99 (2H, m), 2.17-2.23 (1H, m), 2.32 (2H, q, J = 7.6 Hz), 2.43 (2H, dq, J = 3.0, 7.6 Hz), 2.69 (3H, s), 2.96 (1H, m), 3.75 (1H, d, J = 12.2 Hz), 3.80 (1H, d, J = 12.2 Hz), 4.48 (1H, dd, J = 5.1, 11.1 Hz), 5.04 (1H, d, J = 4.1 Hz), 5.23 (1H, d, J = 5.4, 10.8 Hz), 6.42 (1H, s), 7.24 (1H, d, J = 5.9 Hz), 7.39 (1H, dd, J = 4.9, 8.1 Hz), 8.08 (1H, d, J = 8.4 Hz), 8.61 (1H, d, J = 5.1 Hz), 8.67 (1H, d, J = 3.5 Hz), 8.98 (1H, s), 9.17 (1H, s) |

TABLE 24

| 化合物番号 | $^1$H-NMR δ (ppm) |
| --- | --- |
| 240 | 0.93 (3H, s), 1.13 (3H, t, J = 7.9 Hz), 1.19 (3H, t, J = 7.9 Hz), 1.26 (1H, s), 1.39-1.43 (1H, m), 1.49 (3H, s), 1.61 (1H, m), 1.68-1.79 (2H, m), 1.82 (3H, s), 1.88-2.04 (2H, m), 2.17-2.23 (1H, m), 2.32 (2H, q, J = 7.6 Hz), 2.42 (2H, dq, J = 1.9, 7.6 Hz), 2.96 (1H, s), 3.74 (1H, d, J = 11.9 Hz), 3.83 (1H, d, J = 11.9 Hz), 4.83 (1H, dd, J = 1.6, 5.4 Hz), 5.04 (1H, d, J = 4.1 Hz), 5.27 (1H, dd, J = 5.4, 11.6 Hz), 6.43 (1H, s), 7.39 (1H, dd, J = 4.9, 8.1 Hz), 7.47 (1H, d, J = 5.1 Hz), 8.08 (1H, dt, J = 1.9, 8.1 Hz), 8.68 (1H, dd, J = 1.4, 4.6 Hz), 8.64 (1H, d, J = 5.1 Hz), 8.99 (1H, d, J = 1.9 Hz), 9.14 (1H, s) |
| 241 | 0.93 (3H, s), 1.14 (3H, t, J = 7.6 Hz), 1.19 (3H, t, J = 7.6 Hz), 1.26 (1H, s), 1.38-1.43 (1H, m), 1.49 (3H, s), 1.59 (1H, d, J = 4.4 Hz), 1.66-1.73 (2H, m), 1.78 (3H, s), 1.82-2.05 (2H, m), 2.18-2.23 (1H, m), 2.31 (2H, q, J = 7.6 Hz), 2.41 (2H, dq, J = 1.4, 7.6 Hz), 2.96 (1H, s), 3.72 (1H, d, J = 7.6 Hz), 3.81 (1H, d, J = 7.6 Hz), 3.98 (3H, s), 4.84 (1H, dd, J = 5.4, 11.3 Hz), 5.04 (1H, m), 5.24 (1H, dd, J = 4.9, 10.8 Hz), 6.54 (1H, s), 7.39 (1H, dd, J = 4.9, 8.1 Hz), 7.53 (1H, d, J = 4.9 Hz), 8.08 (1H, dt, J = 1.9, 8.1 Hz), 8.68 (1H, d, J = 4.1 Hz), 8.88 (1H, d, J = 4.9 Hz), 9.00 (1H, s), 9.17 (1H, s) |
| 242 | 0.95 (3H, s), 1.15 (3H, t, J = 7.6 Hz), 1.20 (3H, t, J = 7.6 Hz), 1.26 (1H, s), 1.38-1.44 (1H, m), 1.49 (3H, s), 1.61 (1H, d, J = 4.1 Hz), 1.68-1.72 (2H, m), 1.76 (3H, s), 1.82-2.06 (2H, m), 2.18-2.23 (1H, m), 2.34 (2H, q, J = 7.6 Hz), 2.43 (2H, dq, J = 2.2, 7.6 Hz), 2.96 (1H, s), 3.78 (1H, d, J = 12.2 Hz), 3.83 (1H, d, J = 12.2 Hz), 4.84 (1H, dd, J = 5.4, 11.3 Hz), 5.04 (1H, d, J = 4.1 Hz), 5.2-5.34 (1H, m), 6.40 (1H, s), 7.40 (1H, dd, J = 4.9, 8.1 Hz), 7.76 (1H, d, J = 5.4 Hz), 8.02-8.11 (2H, m), 8.69 (1H, d, J = 4.3 Hz), 8.74 (1H, s), 9.00 (1H, s) |
| 243 | 0.93 (3H, s), 1.14 (3H, t, J = 7.6 Hz), 1.20 (3H, t, J = 7.6 Hz), 1.26 (1H, s), 1.39-1.44 (1H, m), 1.50 (3H, s), 1.62 (1H, m), 1.68-1.75 (2H, m), 1.84 (3H, s), 1.93-1.96 (2H, m), 2.14-2.23 (1H, m), 2.33 (2H, q, J = 7.6 Hz), 2.42 (2H, dq, J = 2.4, 7.6 Hz), 2.96 (1H, s), 3.72 (1H, d, J = 11.9 Hz), 3.83 (1H, d, J = 11.9 Hz), 4.83 (1H, dd, J = 1.6, 5.4 Hz), 5.04 (1H, m), 5.36 (1H, dd, J = 4.9, 11.3 Hz), 6.46 (1H, s), 7.38 (1H, dd, J = 5.4, 7.6 Hz), 7.68-7.78 (2H, m), 7.83-7.88 (1H, m), 8.07 (1H, dt, J = 1.9, 8.1 Hz), 8.19-8.23 (1H, m), 8.67 (1H, dd, J = 1.6, 4.9 Hz), 8.98 (1H, d, J = 2.2 Hz) |
| 244 | 0.93 (3H, s), 1.14 (3H, t, J = 7.6 Hz), 1.19 (3H, t, J = 7.6 Hz), 1.26 (1H, s), 1.34-1.43 (1H, m), 1.48 (3H, s), 1.60 (1H, d, J = 4.1 Hz), 1.66-2.02 (4H, m), 1.73 (3H, s), 2.11-2.23 (1H, m), 2.33 (2H, q, J = 7.6 Hz), 2.41 (2H, dq, J = 2.2, 7.6 Hz), 2.90 (1H, s), 3.74 (1H, d, J = 11.9 Hz), 5.83 (1H, d, J = 11.9 Hz), 4.82 (1H, dd, J = 4.9, 11.1 Hz), 5.03 (1H, m), 5.27 (1H, dd, J = 5.1, 11.6 Hz), 6.43 (1H, s), 7.41 (1H, dd, J = 4.9, 8.1 Hz), 7.65-7.70 (2H, m), 7.78-7.86 (2H, m), 8.09 (1H, dt, J = 1.9, 8.1 Hz), 8.69 (1H, d, J = 3.8 Hz), 9.00 (1H, s) |

TABLE 25

| 化合物番号 | $^1$H-NMR δ (ppm) |
| --- | --- |
| 245 | 0.92 (3H, s), 1.14 (3H, t, J = 7.5 Hz), 1.20 (3H, t, J = 7.5 Hz), 1.26 (1H, s), 1.39-1.46 (1H, m), 1.49 (3H, s), 1.62 (1H, d, J = 4.1 Hz), 1.83 (3H, s), 1.66-2.02 (4H, m), 2.11-2.23 (1H, m), 2.33 (2H, dq, J = 1.2, 7.6 Hz), 2.42 (2H, dq, J = 3.2, 7.6 Hz), 2.96 (1H, m), 3.70 (1H, d, J = 12.0 Hz), 3.85 (1H, d, J = 12.0 Hz), 4.83 (1H, dd, J = 4.9, 11.7 Hz), 5.04 (1H, m), 5.27 (1H, dd, J = 5.1, 11.9 Hz), 6.45 (1H, s), 7.18 (1H, dd, J = 8.5, 10.9 Hz), 7.27 (1H, m), 7.38 (1H, dd, J = 4.8, 8.1 Hz), 7.55-7.61 (1H, m), 8.03 (1H, dt, J = 1.7, 7.3 Hz), 8.08 (1H, dt, J = 1.7, 8.3 Hz), 8.67 (1H, d, J = 3.9 Hz), 8.98 (1H, s) |

TABLE 25-continued

| 化合物番号 | ¹H-NMR δ (ppm) |
|---|---|
| 246 | 0.93 (3H, s), 1.14 (3H, t, J = 7.5 Hz), 1.19 (3H, t, J = 7.5 Hz), 1.26 (1H, s), 1.32-1.42 (1H, m), 1.45 (3H, s), 1.59 (1H, d, J = 3.0 Hz), 1.66 (3H, s), 1.69-1.92 (4H, m), 2.02-2.21 (1H, m), 2.33 (2H, dq, J = 1.1, 5.1 Hz), 2.42 (2H, dq, J = 2.2, 5.1 Hz), 2.96 (1H, m), 3.76 (1H, d, J = 11.9 Hz), 3.84 (1H, d, J = 12.0 Hz), 4.83 (1H, dd, J = 4.9, 11.7 Hz), 5.03 (1H, d, J = 4.2 Hz), 5.19 (1H, dd, J = 5.4, 11.7 Hz), 6.60 (1H, s), 7.42 (1H, dd, J = 4.6, 8.1 Hz), 7.66-7.76 (2H, m), 7.84 (1H, dd, J = 1.5, 7.5 Hz), 7.93 (1H, dd, J = 1.5, 7.8 Hz), 8.11 (1H, dt, J = 2.1, 8.1 Hz), 8.69 (1H, d, J = 4.6 Hz), 9.03 (1H, s) |
| 247 | 0.93 (3H, s), 1.14 (3H, t, J = 7.6 Hz), 1.20 (3H, t, J = 7.6 Hz), 1.26 (1H, s), 1.42-1.46 (1H, m), 1.49 (3H, s), 1.61 (1H, d, J = 3.0 Hz), 1.68-1.79 (2H, m), 1.82 (3H, s), 1.86-2.02 (2H, m), 2.16-2.22 (1H, m), 2.33 (2H, dq, J = 1.1, 5.1 Hz), 2.42 (2H, dq, J = 2.4, 5.1 Hz), 2.96 (1H, m), 3.74 (1H, d, J = 12.0 Hz), 3.82 (1H, d, J = 12.0 Hz), 4.83 (1H, dd, J = 4.9, 11.7 Hz), 5.04 (1H, m), 5.27 (1H, dd, J = 5.1, 11.7 Hz), 6.44 (1H, s), 7.40 (1H, dd, J = 4.6, 7.8 Hz), 7.72 (1H, dd, J = 1.7, 8.3 Hz), 8.08 (1H, dt, J = 2.2, 8.5 Hz), 8.26 (1H, dd, J = 1.9, 7.8 Hz), 8.58 (1H, dd, J = 91.9, 4.9 Hz), 8.68 (1H, d, J = 3.6 Hz), .03 (1H, d, J = 1.7 Hz) |
| 248 | 0.93 (3H, s), 1.16 (3H, t, J = 7.6 Hz), 1.22 (3H, t, J = 7.6 Hz), 1.26 (1H, s), 1.42-1.46 (1H, m), 1.49 (3H, s), 1.61 (1H, d, J = 3.0 Hz), 1.68-1.78 (2H, m), 1.82 (3H, s), 1.86-2.01 (2H, m), 2.17-2.22 (1H, m), 2.33 (2H, dq, J = 1.1, 5.1 Hz), 2.42 (2H, dq, J = 2.4, 5.1 Hz), 2.62 (3H, s), 2.98 (1H, m), 3.73 (1H, d, J = 12.0 Hz), 3.84 (1H, d, J = 11.9 Hz), 4.83 (1H, dd, J = 4.8, 11.5 Hz), 5.04 (1H, m), 5.25 (1H, dd, J = 5.1, 11.4 Hz), 6.44 (1H, s), 7.22 (1H, d, J = 7.8 Hz), 7.40 (1H, dd, J = 4.9, 8.0 Hz), 8.08 (1H, dt, J = 2.2, 8.0 Hz), 8.18 (1H, d, J = 7.8 Hz), 8.69 (1H, d, J = 3.7 Hz), 8.99 (1H, d, J = 1.7 Hz) |
| 249 | 0.91 (3H, s), 1.14 (3H, t, J = 7.8 Hz), 1.15 (3H, t, J = 7.7 Hz), 1.26 (1H, s), 1.29-1.39 (1H, m), 1.42 (3H, s), 1.45 (1H, m), 1.57-1.64 (2H, m), 1.66 (3H, s), 1.81-1.88 (2H, m), 2.14-2.18 (1H, m), 2.33 (2H, q, J = 7.8 Hz), 2.35 (2H, q, J = 7.8 Hz), 2.84 (1H, m), 3.46 (3H, s), 3.68 (1H, d, J = 11.7 Hz), 3.93 (1H, d, J = 11.9 Hz), 4.73-4.87 (4H, m), 4.95-5.00 (1H, m), 6.43 (1H, s), 7.42 (1H, dd, J = 4.8, 8.0 Hz), 8.12 (1H, m), 8.69 (1H, m), 9.01 (1H, d, J = 2.2 Hz) |
| 250 | 0.92 (3H, s), 1.26 (1H, s), 1.34-1.55 (3H, m), 1.46 (3H, s), 1.71 (3H, s), 1.66-1.92 (6H, m), 2.01-2.18 (4H, m), 2.38-2.57 (3H, m), 3.66-3.78 (1H, m), 3.95-4.13 (1H, m), 4.73-4.84 (1H, m), 4.89-4.95 (1H, m), 4.99-5.10 (1H, m), 6.45 (1H, s), 7.43 (1H, dd, J = 4.9, 8.3 Hz), 8.11 (1H, m), 8.70 (1H, d, J = 4.9 Hz), 9.02 (1H, s) |

TABLE 26

| 化合物番号 | ¹H-NMR δ (ppm) |
|---|---|
| 251 | 0.93 (3H, s), 1.14 (3H, t, J = 7.5 Hz), 1.17 (3H, t, J = 7.5 Hz), 1.26 (1H, s), 1.36 (9H, s), 1.42 (1H, m), 1.47 (3H, s), 1.62-1.70 (3H, m), 1.75 (3H, s), 1.80-1.95 (2H, m), 2.07-2.21 (1H, m), 2.32 (2H, dq, J = 1.5, 7.5 Hz), 2.40 (2H, dq, J = 3.9, 7.6 Hz), 2.96 (1H, m), 3.69 (1H, d, J = 11.9 Hz), 3.87 (1H, d, J = 11.9 Hz), 4.83 (1H, dd, J = 4.9, 11.7 Hz), 5.04 (1H, m), 5.36 (1H, dd, J = 5.1, 11.7 Hz), 6.53 (1H, s), 7.39-7.43 (1H, m), 7.98 (1H, dd, J = 1.7, 8.0 Hz), 8.02 (1H, s), 8.10 (1H, dt, J = 1.7, 8.0 Hz), 8.65 (1H, dd, J = 1.5, 4.7 Hz), 8.69 (1H, d, J = 3.7 Hz), 8.99 (1H, s) |
| 252 | 0.92 (3H, s), 1.14 (3H, t, J = 7.5 Hz), 1.19 (3H, t, J = 7.5 Hz), 1.26 (1H, s), 1.42-1.45 (1H, m), 1.49 (3H, s), 1.62-1.73 (3H, m), 1.82 (3H, s), 1.84-2.00 (2H, m), 2.18-2.22 (1H, m), 2.32 (2H, dq, J = 1.5, 7.5 Hz), 2.41 (2H, dq, J = 2.5, 7.5 Hz), 2.96 (1H, m), 3.68 (1H, d, J = 11.9 Hz), 3.85 (1H, d, J = 11.7 Hz), 4.82 (1H, dd, J = 4.9, 11.7 Hz), 5.04 (1H, m), 5.37 (1H, dd, J = 4.8, 11.7 Hz), 6.44 (1H, s), 7.36-7.41 (2H, m), 8.08 (1H, dt, J = 1.7, 8.0 Hz), 8.53 (1H, d, J = 2.0 Hz), 8.68 (1H, dd, J = 0.7, 4.9 Hz), 8.98 (1H, d, J = 2.6 Hz) |
| 253 | 0.92 (3H, s), 1.14 (3H, t, J = 7.5 Hz), 1.20 (3H, t, J = 7.5 Hz), 1.26 (1H, s), 1.40-1.47 (1H, m), 1.51 (3H, s), 1.64 (1H, d, J = 2.4 Hz), 1.73 (2H, m), 1.87 (3H, s), 1.85-2.00 (2H, m), 2.18-2.23 (1H, m), 2.32 (2H, q, J = 7.6 Hz), 2.42 (2H, dq, J = 1.5, 7.6 Hz), 2.96 (1H, m), 3.71 (1H, d, J = 12.0 Hz), 3.83 (1H, d, J = 11.9 Hz), 4.84 (1H, dd, J = 4.9, 11.7 Hz), 5.05 (1H, m), 5.39 (1H, dd, J = 5.2, 11.6 Hz), 6.42 (1H, s), 7.39 (1H, dd, J = 4.9, 8.1 Hz), 8.02 (1H, s), 8.07 (1H, dd, J = 4.4 Hz), 8.80-8.83 (1H, m), 8.97 (1H, m), 9.38 (1H, m) |

TABLE 26-continued

| 化合物番号 | ¹H-NMR δ (ppm) |
|---|---|
| 254 | 0.91 (3H, s), 1.14 (3H, t, J = 7.6 Hz), 1.19 (3H, t, J = 7.6 Hz), 1.26 (1H, s), 1.39-1.46 (1H, m), 1.49 (3H, s), 1.63 (1H, d, J = 2.7 Hz), 1.70-1.73 (2H, m), 1.85 (3H, s), 1.88-2.01 (2H, m), 2.18-2.22 (1H, m), 2.32 (2H, q, J = 7.5 Hz), 2.41 (2H, dq, J = 2.2, 7.6 Hz), 2.97 (1H, m), 3.68 (1H, d, J = 11.7 Hz), 3.83 (1H, d, J = 11.9 Hz), 4.83 (1H, dd, J = 4.9, 11.7 Hz), 5.04 (1H, m), 5.34 (1H, dd, J = 5.4, 11.5 Hz), 6.44 (1H, s), 7.39 (1H, dd, J = 4.9, 8.0 Hz), 8.07 (1H, dt, J = 1.9, 6.3 Hz), 8.32 (1H, d, J = 2.0 Hz), 8.67 (1H, d, J = 4.1 Hz), 8.92 (1H, d, J = 2.0 Hz), 8.98 (1H, s) |
| 255 | 0.92 (3H, s), 1.14 (3H, t, J = 7.5 Hz), 1.19 (3H, t, J = 7.5 Hz), 1.26 (1H, s), 1.38-1.45 (1H, m), 1.49 (3H, s), 1.60 (1H, d, J = 3.0 Hz), 1.68-1.70 (2H, m), 1.83 (3H, s), 1.75-1.98 (2H, m), 2.17-2.21 (1H, m), 2.33 (2H, dq, J = 1.7, 7.5 Hz), 2.41 (2H, dq, J = 2.2, 7.5 Hz), 2.97 (1H, m), 3.67 (1H, d, J = 12.0 Hz), 3.87 (1H, d, J = 11.9 Hz), 4.81 (1H, dd, J = 4.9, 11.7 Hz), 5.03 (1H, m), 5.23 (1H, dd, J = 5.1, 11.5 Hz), 6.46 (1H, s), 7.07 (1H, d, J = 5.2 Hz), 7.39 (1H, dd, J = 4.9, 8.1 Hz), 7.54 (1H, d, J = 5.3 Hz), 8.08 (1H, dt, J = 2.2, 8.1 Hz), 8.67 (1H, dd, J = 1.4, 4.9 Hz), 8.99 (1H, d, J = 2.2 Hz) |

TABLE 27

| 化合物番号 | ¹H-NMR δ (ppm) |
|---|---|
| 256 | 0.92 (3H, s), 1.12 (3H, t, J = 7.8 Hz), 1.15 (3H, t, J = 7.7 Hz), 1.26 (1H, s), 1.39-1.47 (1H, m), 1.50 (3H, s), 1.61 (1H, d, J = 2.4 Hz), 1.69-1.81 (2H, m), 1.85 (3H, s), 1.90-1.99 (2H, m), 2.18-2.21 (1H, m), 2.33 (2H, dq, J = 1.2, 7.7 Hz), 2.41 (2H, dq, J = 2.7, 7.6 Hz), 2.66 (3H, s), 2.96 (1H, m), 3.72 (1H, d, J = 11.7 Hz), 3.83 (1H, d, J = 12.0 Hz), 4.83 (1H, dd, J = 4.9, 11.4 Hz), 5.04 (1H, m), 5.25 (1H, dd, J = 5.3, 11.7 Hz), 6.41 (1H, s), 7.30 (1H, d, J = 8.0 Hz), 7.38 (1H, dd, J = 4.9, 8.1 Hz), 8.07 (1H, dt, J = 2.2, 8.1 Hz), 8.24 (1H, dd, J = 2.2, 8.0 Hz), 8.67 (1H, dd, J = 1.5, 4.9 Hz), 8.97 (1H, d, J = 2.2 Hz), 9.18 (1H, d, J = 2.2 Hz) |
| 257 | 0.91 (3H, s), 1.14 (3H, t, J = 7.5 Hz), 1.19 (3H, t, J = 7.5 Hz), 1.26 (1H, s), 1.38-1.46 (1H, m), 1.50 (3H, s), 1.63 (1H, d, J = 2.4 Hz), 1.70-1.73 (2H, m), 1.86 (3H, s), 1.83-1.98 (2H, m), 2.18-2.22 (1H, m), 2.32 (2H, dq, J = 1.5, 7.7 Hz), 2.41 (2H, dq, JJ = 2.2, 7.7 Hz), 2.96 (1H, d, J = 1.9 Hz), 3.68 (1H, d, J = 11.9 Hz), 3.84 (1H, d, J = 12.0 Hz), 4.83 (1H, dd, J = 4.9, 11.7 Hz), 5.05 (1H, m), 5.32 (1H, dd, J = 5.3, 11.7 Hz), 6.43 (1H, s), 7.39 (1H, dd, J = 4.9, 8.0 Hz), 7.56 (1H, d, J = 8.1 Hz), 7.85 (1H, t, J = 7.8 Hz), 8.07 (2H, m), 8.67 (1H, dd, J = 1.7, 4.9 Hz), 8.98 (1H, d, J = 2.0 Hz) |
| 258 | 0.91 (3H, s), 1.14 (3H, t, J = 7.5 Hz), 1.19 (3H, t, J = 7.5 Hz), 1.26 (1H, s), 1.38-1.46 (1H, m), 1.50 (3H, s), 1.62 (1H, d, J = 2.4 Hz), 1.69-1.72 (2H, m), 1.86 (3H, s), 1.80-1.96 (2H, m), 2.18-2.22 (1H, m), 2.32 (2H, q, J = 7.5 Hz), 2.41 (2H, dq, J = 2.2, 7.5 Hz), 2.93 (1H, d, J = 1.9 Hz), 3.68 (1H, d, J = 11.9 Hz), 3.83 (1H, d, J = 12.0 Hz), 4.83 (1H, dd, J = 4.9, 11.4 Hz), 5.04 (1H, m), 5.33 (1H, dd, J = 5.3, 11.5 Hz), 6.42 (1H, s), 7.20 (1H, dd, J = 2.9, 8.0 Hz), 7.38 (1H, dd, J = 4.9, 8.3 Hz), 8.00 (1H, q, J = 7.8 Hz), 8.08 (2H, m), 8.67 (1H, dd, J = 1.4, 4.6 Hz), 8.97 (1H, d, J = 2.2 Hz) |
| 259 | 0.93 (3H, s), 1.14 (3H, t, J = 7.5 Hz), 1.21 (3H, t, J = 7.5 Hz), 1.26 (1H, s), 1.40-1.47 (1H, m), 1.51 (3H, s), 1.61 (1H, d, J = 3.0 Hz), 1.70-1.83 (2H, m), 1.86 (3H, s), 1.92-1.98 (2H, m), 2.17-2.22 (1H, m), 2.32 (2H, q, J = 7.3 Hz), 2.43 (2H, dq, J = 1.4, 5.3 Hz), 2.97 (1H, d, J = 2.0 Hz), 3.74 (1H, d, J = 11.7 Hz), 3.83 (1H, d, J = 11.7 Hz), 4.13 (3H, s), 4.84 (1H, dd, J = 4.9, 11.4 Hz), 5.05 (1H, m), 5.24 (1H, dd, J = 5.3, 11.7 Hz), 6.43 (1H, s), 7.16-7.20 (1H, m), 7.35-7.44 (4H, m), 7.70 (1H, d, J = 8.1 Hz), 8.05 (1H, dt, J = 1.7, 8.3 Hz), 8.66 (1H, dd, J = 1.5, 4.9 Hz), 8.96 (1H, d, J = 2.2 Hz) |
| 260 | 0.93 (3H, s), 1.14 (3H, t, J = 7.5 Hz), 1.19 (3H, t, J = 7.5 Hz), 1.26 (1H, s), 1.40-1.46 (1H, m), 1.48 (3H, s), 1.63 (1H, d, J = 3.0 Hz), 1.71-1.74 (2H, m), 1.80 (3H, s), 1.83-1.95 (1H, m), 2.02-2.06 (1H, m), 2.18-2.22 (1H, m), 2.32 (2H, dq, J = 1.7, 7.6 Hz), 2.41 (2H, dq, J = 3.4, 7.5 Hz), 2.96 (1H, m), 3.70 (1H, d, J = 12.0 Hz), 3.87 (1H, d, J = 11.9 Hz), 4.83 (1H, dd, J = 4.8, 11.5 Hz), 5.05 (1H, m), 5.37 (1H, dd, J = 4.9, 11.7 Hz), 6.46 (1H, s), 7.39-7.45 (2H, m), 7.87 (1H, dd, J = 1.5, 8.3 Hz), 8.08 (1H, dt, J = 1.5, 8.3 Hz), 8.64 (1H, dd, J = 1.2, 4.6 Hz), 8.69 (1H, d, J = 4.9 Hz), 8.97 (1H, d, J = 2.2 Hz) |

TABLE 27-continued

| 化合物番号 | $^1$H-NMR δ (ppm) |
|---|---|
| 261 | 0.85-1.06 (8H, m), 0.92 (3H, s), 1.26 (1H, s), 1.30-1.40 (1H, m), 1.42 (3H, s), 1.45-1.63 (5H, m), 1.67 (3H, s), 1.81-1.92 (2H, m), 2.14-2.25 (2H, m), 2.88 (1H, d, J = 1.4 Hz), 3.75 (1H, d, J = 11.9 Hz), 3.86 (1H, d, J = 11.6 Hz), 3.78-3.82 (1H, m), 4.82 (1H, dd, J = 5.1, 11.4 Hz), 5.00 (1H, m), 6.52 (1H, s), 7.42 (1H, dd, J = 4.9, 8.0 Hz), 8.11 (1H, dt, J = 1.7, 8.0 Hz), 8.69 (1H, dd, J = 1.5, 4.9 Hz), 9.01 (1H, d, J = 1.9 Hz) |

TABLE 28

| 化合物番号 | $^1$H-NMR δ (ppm) |
|---|---|
| 262 | 0.92 (3H, s), 1.14 (3H, t, J = 7.5 Hz), 1.20 (3H, t, J = 7.5 Hz), 1.26 (1H, s), 1.39-1.47 (1H, m), 1.49 (3H, s), 1.61 (1H, d, J = 2.7 Hz), 1.66-1.71 (2H, m), 1.84 (3H, s), 1.76-1.99 (2H, m), 2.18-2.22 (1H, m), 2.32 (2H, dq, J = 1.0, 7.5 Hz), 2.42 (2H, dq, J = 2.7, 7.5 Hz), 2.96 (1H, m), 3.73 (1H, d, J = 11.9 Hz), 3.82 (1H, d, J = 11.9 Hz), 4.83 (1H, dd, J = 4.9, 11.7 Hz), 5.04 (1H, m), 5.26 (1H, dd, J = 5.1, 11.7 Hz), 6.44 (1H, s), 7.35-7.41 (2H, m), 8.07 (1H, dt, J = 1.7, 8.0 Hz), 8.44-8.50 (2H, m), 8.67 (1H, d, J = 4.9 Hz), 8.98 (1H, d, J = 1.7 Hz) |
| 263 | 0.92 (3H, s), 1.12 (3H, t, J = 7.5 Hz), 1.20 (3H, t, J = 7.5 Hz), 1.26 (1H, s), 1.30-1.47 (1H, m), 1.50 (3H, s), 1.62 (1H, d, J = 2.4 Hz), 1.69-1.71 (2H, m), 1.85 (3H, s), 1.75-1.97 (2H, m), 2.18-2.22 (1H, m), 2.33 (2H, dq, J = 0.9, 7.6 Hz), 2.42 (2H, dq, J = 2.4, 7.6 Hz), 2.98 (1H, m), 3.73 (1H, d, J = 11.6 Hz), 3.81 (1H, d, J = 11.9 Hz), 4.84 (1H, dd, J = 4.9, 11.7 Hz), 5.05 (1H, m), 5.26 (1H, dd, J = 5.1, 11.5 Hz), 6.40 (1H, s), 7.38 (1H, dd, J = 4.9, 8.0 Hz), 7.80 (2H, d, J = 8.8 Hz), 8.06 (1H, dt, J = 1.7, 8.0 Hz), 8.21 (2H, d, J = 8.8 Hz), 8.67 (1H, dd, J = 1.5, 4.9 Hz), 8.96 (1H, d, J = 1.7 Hz) |
| 264 | 0.92 (3H, s), 1.14 (3H, t, J = 7.5 Hz), 1.20 (3H, t, J = 7.5 Hz), 1.26 (1H, s), 1.39-1.47 (1H, m), 1.51 (3H, s), 1.62 (1H, d, J = 2.4 Hz), 1.68-1.82 (2H, m), 1.86 (3H, s), 1.93-2.01 (2H, m), 2.19-2.23 (1H, m), 2.32 (2H, dq, J = 1.0, 7.6 Hz), 2.42 (2H, dq, J = 2.4, 7.5 Hz), 2.97 (1H, m), 3.73 (1H, d, J = 11.9 Hz), 3.80 (1H, d, J = 11.9 Hz), 4.84 (1H, dd, J = 4.9, 11.7 Hz), 5.05 (1H, m), 5.26 (1H, dd, J = 5.1, 11.5 Hz), 6.41 (1H, s), 7.38 (1H, dd, J = 4.1, 8.0 Hz), 7.65 (1H, m), 7.90 (1H, dt, J = 1.5, 7.8 Hz), 8.07 (1H, dt, J = 2.2, 8.0 Hz), 8.34 (1H, dt, J = 1.5, 7.8 Hz), 8.38 (1H, t, J = 1.5 Hz), 8.67 (1H, dd, J = 1.5, 4.9 Hz), 8.96 (1H, d, J = 2.4 Hz) |
| 265 | 0.92 (3H, s), 1.14 (3H, t, J = 7.5 Hz), 1.21 (3H, t, J = 7.5 Hz), 1.26 (1H, s), 1.39-1.48 (1H, m), 1.51 (3H, s), 1.63 (1H, d, J = 2.7 Hz), 1.63-1.83 (2H, m), 1.86 (3H, s), 1.90-1.98 (2H, m), 2.18-2.23 (1H, m), 2.33 (2H, q, J = 7.5 Hz), 2.43 (2H, dq, J = 2.5, 7.6 Hz), 2.97 (1H, m), 3.72 (1H, d, J = 11.9 Hz), 3.82 (1H, d, J = 12.0 Hz), 4.84 (1H, dd, J = 4.9, 11.4 Hz), 5.05 (1H, dd, J = 4.1 Hz), 5.28 (1H, dd, J = 5.1, 11.5 Hz), 6.42 (1H, s), 7.38 (1H, dd, J = 4.9, 8.0 Hz), 7.65 (1H, t, J = 7.8 Hz), 7.88 (1H, d, J = 7.8 Hz), 8.06 (1H, dt, J = 1.8, 8.0 Hz), 8.30 (1H, d, J = 8.1 Hz), 8.36 (1H, s), 8.67 (1H, dd, J = 1.5, 4.9 Hz), 8.97 (1H, d, J = 2.2 Hz) |
| 266 | 0.89 (3H, s), 1.13 (3H, t, J = 7.6 Hz), 1.14 (3H, t, J = 7.6 Hz), 1.26 (1H, s), 1.33-1.37 (1H, m), 1.42 (3H, s), 1.46-1.55 (1H, m), 1.58 (3H, s), 1.60-1.70 (2H, m), 1.78-1.91 (2H, m), 2.13-2.17 (1H, m), 2.32 (2H, dq, J = 1.7, 7.3 Hz), 2.35 (2H, q, J = 7.3 Hz), 2.89 (1H, m), 3.66 (1H, d, J = 11.4 Hz), 3.81 (1H, d, J = 12.0 Hz), 3.96 (2H, s), 4.76-4.82 (1H, m), 4.98-5.06 (2H, m), 6.38 (1H, s), 7.17-7.25 (1H, m), 7.36-7.46 (2H, m), 7.69-7.73 (1H, m), 8.08-8.12 (1H, m), 8.60 (1H, dt, J = 1.0, 4.9 Hz), 8.70 (1H, dd, J = 1.7, 4.9 Hz), 9.00 (1H, d, J = 1.4 Hz) |

TABLE 29

| 化合物番号 | $^1$H-NMR δ (ppm) |
|---|---|
| 267 | 0.89 (3H, s), 1.13 (3H, t, J = 7.6 Hz), 1.15 (3H, t, J = 7.6 Hz), 1.26 (1H, s), 1.43 (3H, s), 1.50 (3H, d, J = 3.0 Hz), 1.61 (3H, s), 1.58-1.70 (2H, m), 1.75-1.93 (2H, m), 2.14-2.18 (1H, m), 2.32 (2H, q, J = 7.6 Hz), 2.36 (2H, q, J = 7.6 Hz), 2.90 (1H, d, J = 1.9 Hz), 3.70 (1H, d, J = 12.0 Hz), 3.74 (2H, s), 3.77 (1H, d, J = 11.9 Hz), 4.79 (1H, dd, J = 4.9, 11.4 Hz), 4.96-5.00 (2H, m), 6.37 (1H, s), 7.32 (1H, dd, J = 4.8, 7.6 Hz), 7.42 (1H, dd, J = 4.9, 8.1 Hz), 7.71 (1H, d, J = 7.8 Hz), 8.12 (1H, dt, J = 1.9, 8.1 Hz), 8.57 (1H, dd, J = 1.6, 4.8 Hz), 8.65 (1H, d, J = 1.9 Hz), 8.70 (1H, dd, J = 1.6, 4.7 Hz), 9.04 (1H, d, J = 4.2 Hz) |

TABLE 29-continued

| 化合物番号 | $^1$H-NMR δ (ppm) |
|---|---|
| 269 | 0.85-1.11 (8H, m), 0.93 (3H, s), 1.26 (1H, s), 1.39-1.47 (1H, m), 1.50 (3H, s), 1.55-1.68 (5H, m), 1.87 (3H, s), 1.83-2.02 (2H, m), 2.17-2.22 (1H, m), 2.96 (1H, s), 3.79 (1H, d, J = 12.2 Hz), 3.83 (1H, d, J = 12.1 Hz), 4.85 (1H, dd, J = 4.9, 11.5 Hz), 5.04 (1H, m), 5.38 (1H, dd, J = 5.12, 11.6 Hz), 6.46 (1H, s), 7.38 (1H, dd, J = 4.8, 8.2 Hz), 7.69-7.80 (2H, m), 7.87 (1H, m), 8.08 (1H, dt, J = 2.2, 8.0 Hz), 8.22 (1H, dd, J = 1.7, 7.5 Hz), 8.67 (1H, dd, J = 1.5, 4.9 Hz), 8.98 (1H, d, J = 2.4 Hz) |
| 270 | 0.86-1.10 (8H, m), 0.94 (3H, s), 1.26 (1H, s), 1.38-1.46 (1H, m), 1.49 (3H, s), 1.57-1.69 (5H, m), 1.75 (3H, s), 1.78-2.05 (2H, m), 2.18-2.21 (1H, m), 3.80 (1H, d, J = 11.9 Hz), 3.84 (1H, d, J = 11.9 Hz), 4.84 (1H, dd, J = 5.0, 11.6 Hz), 5.04 (1H, m), 5.31 (1H, dd, J = 5.0, 11.8 Hz), 6.42 (1H, s), 7.40 (1H, dd, J = 4.9, 8.3 Hz), 7.70 (1H, d, J = 5.3 Hz), 8.09 (1H, dt, J = 1.7, 8.1 Hz), 8.69 (1H, dd, J = 1.6, 4.7 Hz), 8.97 (1H, d, J = 5.1 Hz), 9.00 (1H, d, J = 2.2 Hz), 9.17 (1H, s) |
| 271 | 0.85-1.08 (8H, m), 0.92 (3H, s), 1.26 (1H, s), 1.38-1.46 (1H, m), 1.48 (3H, s), 1.56-1.68 (5H, m), 1.79 (3H, s), 1.83-2.08 (2H, m), 2.18-2.21 (1H, m), 2.95 (1H, m), 3.76 (1H, d, J = 11.9 Hz), 3.86 (1H, d, J = 11.9 Hz), 4.83 (1H, dd, J = 4.9, 11.5 Hz), 5.04 (1H, m), 5.39 (1H, dd, J = 5.1, 11.9 Hz), 646 (1H, s), 7.34-7.45 (2H, m), 7.86 (1H, dd, J = 1.3, 8.0 Hz), 8.08 (1H, dt, J = 2.0, 8.0 Hz), 8.64 (1H, dd, J = 1.2, 4.7 Hz), 8.68 (1H, dd, J = 1.5, 4.9 Hz), 9.00 (1H, d, J = 2.2 Hz) |

Example 11

Preparation Example 1

Wettable Powder

Compound According to the Present Invention

| | |
|---|---|
| (Compound No. 82) | 30 wt % |
| Clay | 30 wt % |
| Diatomaceous earth | 35 wt % |
| Calcium lignin sulfonate | 4 wt % |
| Sodium laurylsulfate | 1 wt % |

The above ingredients were homogeneously mixed together, and the mixture was ground to prepare wettable powder.

Preparation Example 2

Dust

Compound According to the Present Invention

| | |
|---|---|
| (Compound No. 82) | 2 wt % |
| Clay | 60 wt % |
| Talc | 37 wt % |
| Calcium stearate | 1 wt % |

The above ingredients were homogeneously mixed together to prepare dust.

Preparation Example 3

Emulsifiable Concentrate

Compound According to the Present Invention

| | |
|---|---|
| (Compound No. 82) | 20 wt % |
| N,N-Dimethylformamide | 20 wt % |
| Solvesso 150 (Exxon Mobil Corporation) | 50 wt % |
| Polyoxyethylene alkylaryl ether | 10 wt % |

The above ingredients were homogeneously mixed and dissolved to prepare emulsifiable concentrate.

Preparation Example 4

Granules

Compound According to the Present Invention

| (Compound No. 28) | 5 wt % |
|---|---|
| Bentonite | 40 wt % |
| Talc | 10 wt % |
| Clay | 43 wt % |
| Calcium lignin sulfonate | 2 wt % |

The above ingredients were homogeneously ground and homogeneously mixed together. Water was added to the mixture, followed by thorough kneading. Thereafter, the kneaded product was granulated and dried to prepare granules.

Preparation Example 5

Floables

Compound According to the Present Invention

| (Compound No. 28) | 25 wt % |
|---|---|
| POE polystyrylphenyl ether sulfate | 5 wt % |
| Propylene glycol | 6 wt % |
| Bentonite | 1 wt % |
| 1% aqueous xanthan gum solution | 3 wt % |
| PRONAL EX-300 (Toho Chemical Industry Co., Ltd.) | 0.05 wt % |
| ADDAC 827 (K.I. Chemical Industry Co., Ltd.) | 0.02 wt % |
| Water | To 100 wt % |

All the above ingredients except for the 1% aqueous xanthan gum solution and a suitable amount of water were premixed together, and the mixture was then ground by a wet grinding mill. Thereafter, the 1% aqueous xanthan gum solution and the remaining water were added to the ground product to prepare 100 wt % floables.

Test Example 1

Pesticidal Effect Against *Mvzus Persicae*

Among the compounds of formula (I) produced by the conventional method described above, the compounds shown in Tables 1 to 14 and pyripyropene A were tested for pesticidal effect.

A leaf disk having a diameter of 2.8 cmϕ was cut out from a cabbage grown in a pot and was placed in a 5.0 cm-Schale. Four adult aphids of *Myzus persicae* were released in the Schale. One day after the release of the adult aphids, the adult aphids were removed. The number of larvae at the first instar born in the leaf disk was adjusted to 10, and a test solution, which had been adjusted to a concentration of 20 ppm by the addition of a 50% aqueous acetone solution (0.05% Tween 20 added) was spread over the cabbage leaf disk. The cabbage leaf disk was then air dried. Thereafter, the Schale was lidded and was allowed to stand in a temperature-controlled room (light period 16 hr—dark period 8 hr) (25° C.). Three days after the initiation of standing of the Schale, the larvae were observed for survival or death, and the death rate of larvae was calculated by the following equation.

Death rate (%)={number of dead larvae/(number of survived larvae+number of dead larvae)}×100

As result, it was found that the death rate was not less than 80% for compounds of Nos. 1, 6, 8, 9, 10, 12, 14, 16, 18, 20, 23, 25, 28, 34, 35, 36, 37, 38, 39, 40, 44, 45, 49, 54, 56, 57, 61, 69, 76, 82, 85, 86, 88, 90, 91, 98, 103, 106, 107, 108, 109, 111, 125, 128, 133, 135, 137, 139, 142, 153, 160, 161, 162, 164, 167, 169, 170, 171, 172, 176, 180, 182, 183, 186, 187, 190, 196, 201, 205, 206, 207, 208, 209, 210, 211, 212, 213, 214, 215, 216, 217, 218, 219, 220, 221, 222, 223, 226, 227, 228, 229, 230, 231, 232, 233, 236, 237, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, and 274 and pyripyropene A.

Test Example 2

Pesticidal Effect Against *Mvzus Persicae*

Among the compounds of formula (I) produced by the conventional method described above, the compounds shown in Tables 1 to 14 and pyripyropene A were tested for pesticidal effect.

A leaf disk having a diameter of 2.8 cmϕ was cut out from a cabbage grown in a pot and was placed in a 5.0 cm-Schale. Four adult aphids of *Myzus persicae* were released in the Schale. One day after the release of the adult aphids, the adult aphids were removed. The number of larvae at the first instar born in the leaf disk was adjusted to 10, and a test solution, which had been adjusted to a concentration of 0.156 ppm by the addition of a 50% aqueous acetone solution (0.05% Tween 20 added) was spread over the cabbage leaf disk. The cabbage leaf disk was then air dried. Thereafter, the Schale was lidded and was allowed to stand in a temperature-controlled room (light period 16 hr-dark period 8 hr) (25° C.). Three days after the initiation of standing, the larvae were observed for survival or death, and the death rate of larvae was calculated in the same manner as in Test Example 1.

As result, it was found that the death rate was not less than 80% for compounds of Nos. 12, 23, 28, 45, 54, 56, 76, 82, 85, 86, 90, 164, 201, 205, 206, 207, 212, 213, 217, 218, 219, 222, 227, 228, 229, 231, 232, 233, 237, 239, 240, 242, 246, 247, 249, 250, 252, 253, 256, 258, 261, 262, 264, 265, 266, 267, 269, 270, and 271.

Test Example 3

Pesticidal Effect Against *Plutella Xylostella*

A cabbage leaf disk having a diameter of 5 cm was placed in a plastic cup. Test compounds, which had been diluted to a predetermined concentration by the addition of a 50% aqueous acetone solution (Tween 20, 0.05% added), were spreaded over the cabbage leaf disk by means of a spray gun, and the cabbage leaf disk was then air dried. Five larvae at the second instar of *Plutella xylostella* were released in the cup. The cup was then lidded, and the larvae were reared in the temperature-controlled room (25° C.). Three days after the treatment, the larvae were observed for survival or death, and the death rate of the larvae was calculated in the same manner as in Test Example 1.

As a results, it was found that the death rate was not less than 80% for compounds of Nos. 76, 213, 218, 237 and 250 at a concentration of 500 ppm.

Test Example 4

Pesticidal Effect Against *Helicoverpa Armigera*

A cabbage leaf disk having a diameter of 2.8 cm was placed is in a plastic cup. Test compounds, which had been diluted to a predetermined concentration by the addition of a 50% aqueous acetone solution (Tween 20, 0.05% added), were spreaded over the cabbage leaf disk by means of a spray gun, and the cabbage leaf disk was then air dried. A larva at the third instar of *Helicoverpa armigera* was released in the cup. The cup was then lidded, and the larva was reared in the temperature-controlled room (25° C.). Three days after the treatment, the larva was observed for survival or death. The test was repeated 5 times. Further, the death rate of the larvae were calculated in the same manner as in Test Example 1.

As a result, it was found that the death rate was not less than 80% for the compound of No. 219 at a concentration of 100 ppm.

Test Example 5

Pesticidal Effect Against *Trigonotylus Caelestialium*

A wheat seedling was immersed for 30 seconds in a solution, in which each test compound had been diluted to a predetermined concentration by the addition of a 50% aqueous acetone solution (Tween 20, 0.05% added). The wheat seedling was air dried, and then placed in a glass cylinder. Further, two larvae at the second instar of *Trigonotylus caelestialium* were released in the glass cylinder. The glass cylinder was then lidded, and the larvae were reared in the temperature-controlled room (25° C.). During the test, the wheat seedling was supplied with water from the bottom of the glass cylinder. Three days after the treatment, the larvae were observed for survival or death, and the death rate of the larvae were calculated in the same manner as in Test Example 1.

As a result, it was found that the death rate was not less than 80% for compound of Nos. 218 and 261 at a concentration of 100 ppm.

The invention claimed is:

1. A compound represented by formula (Ib) or an agriculturally and horticulturally acceptable salt thereof:

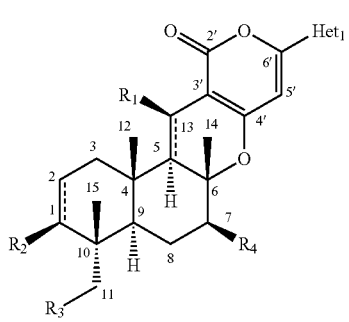

(Ib)

wherein $Het_1$ represents 3-pyridyl, $R_1$ represents hydroxyl, $R_2$ and $R_3$ represent propionyloxy or optionally substituted cyclic $C_{3-6}$ alkylcarbonyloxy, and $R_4$ represents hydroxyl, optionally substituted cyclic $C_{3-6}$ alkylcarbonyloxy, optionally substituted benzoyloxy, or optionally substituted saturated or unsaturated five- or six-membered heterocyclic carbonyloxy, provided that a compound wherein $Het_1$ represents 3-pyridyl, $R_1$ represents hydroxyl, $R_2$ and $R_3$ represent propionyloxy, and $R_4$ represents hydroxyl, is excluded.

2. The compound according to claim 1 or an agriculturally and horticulturally acceptable salt thereof, wherein $R_2$ and $R_3$ represent optionally substituted cyclic $C_{3-6}$ alkylcarbonyloxy, and $R_4$ represents hydroxyl, optionally substituted cyclic $C_{3-6}$ alkylcarbonyloxy, or optionally substituted benzoyloxy.

3. The compound according to claim 1 or an agriculturally and horticulturally acceptable salt thereof, wherein $R_2$ and $R_3$ represent propionyloxy, and $R_4$ represents optionally substituted cyclic $C_{3-6}$ alkylcarbonyloxy or optionally substituted saturated or unsaturated five- or six-membered heterocyclic carbonyloxy.

4. An agricultural and horticultural composition comprising the compound according to claim 1 or an agriculturally and horticulturally acceptable salt thereof as active ingredient and an agriculturally and horticulturally acceptable carrier.

* * * * *